US011085131B1

(12) United States Patent
Fox et al.

(10) Patent No.: US 11,085,131 B1
(45) Date of Patent: *Aug. 10, 2021

(54) NUCLEIC ACID-GUIDED EDITING OF EXOGENOUS POLYNUCLEOTIDES IN HETEROLOGOUS CELLS

(71) Applicant: Inscripta, Inc., Boulder, CO (US)

(72) Inventors: Richard Fox, Boulder, CO (US); Daniel Held, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/232,046

(22) Filed: Apr. 15, 2021

Related U.S. Application Data

(63) Continuation of application No. 16/950,878, filed on Nov. 17, 2020, now Pat. No. 10,995,424, which is a continuation of application No. 16/798,338, filed on Feb. 22, 2020, now Pat. No. 10,858,761, which is a continuation-in-part of application No. 16/670,340, filed on Oct. 31, 2019, now Pat. No. 10,676,842, which is a continuation of application No. 16/392,605, filed on Apr. 23, 2019, now Pat. No. 10,557,216.

(60) Provisional application No. 62/810,001, filed on Feb. 25, 2019, provisional application No. 62/671,266, filed on May 14, 2018, provisional application No. 62/662,126, filed on Apr. 24, 2018.

(51) Int. Cl.
| | |
|---|---|
| *C12N 9/22* | (2006.01) |
| *C40B 50/06* | (2006.01) |
| *C40B 30/04* | (2006.01) |
| *C40B 40/10* | (2006.01) |
| *C07K 16/28* | (2006.01) |
| *C07K 14/74* | (2006.01) |
| *C40B 70/00* | (2006.01) |
| *C12N 15/81* | (2006.01) |
| *C12N 15/85* | (2006.01) |
| *C12N 15/90* | (2006.01) |
| *C40B 20/04* | (2006.01) |
| *C40B 40/02* | (2006.01) |
| *C12N 15/10* | (2006.01) |

(52) U.S. Cl.
CPC ........ *C40B 50/06* (2013.01); *C07K 14/70539* (2013.01); *C07K 16/2809* (2013.01); *C12N 9/22* (2013.01); *C12N 15/1037* (2013.01); *C12N 15/81* (2013.01); *C12N 15/85* (2013.01); *C12N 15/907* (2013.01); *C40B 20/04* (2013.01); *C40B 30/04* (2013.01); *C40B 40/02* (2013.01); *C40B 40/10* (2013.01); *C40B 70/00* (2013.01)

(58) Field of Classification Search
None
See application file for complete search history.

(56) References Cited

U.S. PATENT DOCUMENTS

| | | | |
|---|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |
| 10,837,021 B1 | 11/2020 | Tian et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2010/0076057 A1 | 3/2010 | Sontheimer et al. |
| 2014/0068797 A1 | 3/2014 | Doudna et al. |
| 2014/0199767 A1 | 7/2014 | Barrangou et al. |
| 2014/0273226 A1 | 9/2014 | Wu et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

International Search Report and Written Opinion for International Application No. PCT/US20/19379, dated Jul. 22, 2020, p. 1-10.

(Continued)

*Primary Examiner* — Christopher M Gross

(74) *Attorney, Agent, or Firm* — Sarah Brashears; Dianna L. DeVore

(57) ABSTRACT

The present disclosure provides shuttle vectors for editing exogenous polynucleotides in heterologous live cells, as well as automated methods, modules, and multi-module cell editing instruments and systems for performing the editing methods.

30 Claims, 22 Drawing Sheets

(56) References Cited

U.S. PATENT DOCUMENTS

| | | |
|---|---|---|
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2019/0017072 A1 | 1/2019 | Ditommaso et al. |
| 2019/0136230 A1 | 5/2019 | Sather et al. |
| 2019/0169605 A1 | 6/2019 | Masquelier et al. |
| 2020/0263197 A1 | 8/2020 | Cheng et al. |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2014/144495 | 9/2014 |
| WO | WO 2016/110453 | 7/2016 |
| WO | WO2016/110453 | 7/2016 |
| WO | WO 2017/053902 | 3/2017 |
| WO | WO 2017/078631 | 5/2017 |
| WO | WO 2017/083722 | 5/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO2017/216392 | 12/2017 |
| WO | WO 2017/216392 | 12/2017 |
| WO | WO2017/223330 | 12/2017 |
| WO | WO 2017/223330 | 12/2017 |
| WO | WO 2018/031950 | 2/2018 |
| WO | WO 2018/071672 | 4/2018 |
| WO | WO 2018/083339 | 5/2018 |
| WO | WO 2018/191715 | 10/2018 |
| WO | WO2019/006436 | 1/2019 |
| WO | WO2019/209926 | 10/2019 |
| WO | WO2020/021045 | 1/2020 |

OTHER PUBLICATIONS

International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpfl enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018)
dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologics", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "Tales of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).

(56) References Cited

OTHER PUBLICATIONS

Durai et al., "Zinc finger nucleases: custom-designed molecular scissors for genome engineering of plant and mammalian cells", Nucleic Acids Res., 33(18):5978-90 (2005).
Kadonaga et al.; "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within Cag repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836 dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.

Cassette Error Category Breakdown

| Edit Category | Number wells |
|---|---|
| Clonal Complete Intended | 44 |
| Subclonal Complete Intended | 6 |
| Reference | 10 |
| Inconclusive | 28 |
| Unobserved | 8 |

Table: Edit category summary

FIG. 9

NUCLEIC ACID-GUIDED EDITING OF EXOGENOUS POLYNUCLEOTIDES IN HETEROLOGOUS CELLS

RELATED CASES

The present invention is a continuation of U.S. Ser. No. 16/950,878, filed 17 Nov. 2020, now allowed; which is a continuation of U.S. Ser. No. 16/798,338, filed 22 Feb. 2020, now U.S. Pat. No. 10,858,761 which claims priority to U.S. Ser. No. 62/810,001, filed 25 Feb. 2019; which is a continuation-in-part of U.S. Ser. No. 16/670,340, filed 31 Oct. 2019, now U.S. Pat. No. 10,676,842; which is a continuation of U.S. Ser. No. 16/392,605, filed 23 Apr. 2019, now U.S. Pat. No. 10,557,216; which claims priority to U.S. Ser. No. 62/671,266, filed 14 May 2018, and U.S. Ser. No. 62/662,126, filed 24 Apr. 2018, all of which are incorporated by reference for all purposes.

FIELD OF THE INVENTION

The present disclosure provides shuttle vectors and automated methods and multi-module cell editing instruments and systems for editing exogenous polynucleotides in heterologous cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genome editing with engineered nucleases is a method in which changes to nucleic acids are made in the genome of a living organism. Certain nucleases create site-specific double-strand breaks at target regions in the genome, which can be repaired by homologous recombination, resulting in targeted edits. These nucleases can be used to introduce one or more edits into multiple cells simultaneously, allowing for the production of libraries of cells with one or more edits in the genome. Moreover, in addition to the genome, nucleic acid guided nuclease editing can be used to edit exogenous nucleic acid sequences in a cell, such as nucleic acid sequences residing on a vector.

In some circumstances, it may be desirable to edit nucleic acid sequences of a cell type or genome that is difficult to manipulate, maintain in culture, or edit (e.g., a source cell or genome). In such circumstances a shuttle vector may be useful for cloning the target polynucleotide and editing the sequence in a cell type that is easy to manipulate, maintain in culture and edit due to, e.g., the cell type being well-studied and well-known in the art (e.g. an editing cell). Once edited, the shuttle vector with the edited target polynucleotide may be returned to the source cell type for further study.

There are various and diverse methods for delivering exogenous polynucleotides from the genome of one organism to another, in this case for automated editing by nucleic acid-guided nucleases, and a number of considerations must be taken into account when designing the methods and shuttle vectors to be used, including payload size of the exogenous polynucleotide locus; means for maintaining the shuttle vector at a suitable copy number during expansion and propagation of the source cells and editing cells; specific requirements of transformation, transfection, and nucleic acid isolation protocols depending on the species of the source cells and editing cells; and the ultimate destination of the edited target polynucleotide.

To date, however, editing of nucleic acids—much less shuttle vectors or larger artificial chromosomes carrying hundreds of kilobases of exogenous polynucleotides—in a cell has not been compatible with automation due to low efficiencies and challenges with cell selection. There is thus a need for shuttle vectors and automated methods and multi-module cell processing instruments capable of editing exogenous polynucleotides in heterologous cells. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides shuttle vectors carrying inserts of target polynucleotides and automated modules and multi-module cell editing instrumentation for nucleic-acid guided nuclease editing of target polynucleotides in heterologous editing cells. The shuttle vectors are used to transfer target polynucleotides from cells of one source organism to cells of a heterologous editing organism. Nucleic acids comprising editing "machinery" are introduced into the editing cells to enable nucleic acid-guided nuclease editing of the target polynucleotides. Edited target polynucleotides are subsequently characterized, isolated, and used for downstream applications, including re-introduction of the edited polynucleotides into cells of the source organism.

Nucleic-acid guided nuclease editing of target polynucleotides is a powerful tool for research, biochemical production, cell engineering and therapy, where automated methods and modules and multi-module cell editing instrumentation for nucleic-acid guided nuclease editing present distinct advantages over the state of the art. The present disclosure enables automated nucleic-acid guided nuclease editing of target polynucleotides from the genome of essentially any organism.

Thus, there is provided a method of automated nucleic acid-guided nuclease editing of exogenous polynucleotides from source cells within heterologous editing cells, comprising: inserting one or more target polynucleotides from the source cells into shuttle vector backbones to form a library of shuttle vectors; transferring the library of shuttle vectors into a first receptacle; providing heterologous editing cells in a second receptacle; growing the heterologous editing cells in a growth module; transferring the heterologous editing cells from the growth module to a cell concentration module; concentrating and rendering electrocompetent the heterologous editing cells in the cell concentration module; introducing the library of shuttle vectors into the heterologous editing cells in a transformation module; providing one or more editing vectors wherein the editing vectors comprise a coding sequence for a nuclease, a guide nucleic acid and a DNA donor sequence in a third receptacle; introducing the one or more editing vectors into the heterologous editing cells in the transformation module; transferring the heterologous editing cells from the transformation module to an editing module; allowing editing to take place in the editing module under conditions that allow the editing vectors to edit the one or more target polynucleotides in the shuttle vectors thereby forming edited shuttle vectors; identifying living editing cells containing the edited shuttle vectors; isolating the living editing cells containing the edited shuttle vectors; isolating the edited shuttle vectors; wherein all of the first receptacle, second receptacle, third receptacle, growth module, cell concentration module, transformation module and editing module are comprised within an automated multi-module cell processing instrument. In some aspects, a liquid handling system moves the heterologous editing cells from the first receptacle to the growth module, from the growth module to the cell concentration module, from the cell concentration module to the transformation module, and from the transformation module to the editing module; and moves the shuttle vector library from the second receptacle to the transformation module and moves the one or more editing vectors from the third receptacle to the transformation module.

In some aspects, the heterologous editing cells are bacterial cells; in some aspects, the heterologous editing cells are yeast cells; and in some aspects the heterologous editing cells are mammalian cells. In some aspects, the heterologous editing cells are iPSCs.

In some aspects, the shuttle vector backbone is a bacterial plasmid that comprises a DNA plasmid comprising a bacterial origin of replication and selectable marker, and in some aspects, the shuttle vector is a bacterial artificial chromosome.

In other aspects, the shuttle vector backbone is a yeast plasmid that comprises a DNA plasmid comprising a yeast origin of replication, an ARS, CEN sequence, and selectable marker, and in some aspects, the shuttle vector is a yeast artificial chromosome. In yet other aspects, the shuttle vector backbone is a synthetic chromosome.

In some aspects, at least one target polynucleotide is selected from a full-length gene; an open reading frame; or a genomic locus of size 1000-10,000 nucleotides, 50-500 nucleotides, 10-100 nucleotides, or 10,000-100,000 nucleotides.

In some aspects, the source cells are animal cells and in some aspects, the animal cells are mammalian cells. In some aspects, the mammalian cells are human cells. In other aspects, the source cells are bacterial cells. In yet other aspects, the source cells are yeast cells or plant cells.

In some aspects, the shuttle vector transfers nucleic acids from one species of bacteria to another species of bacteria, or from one species of yeast to another species of yeast, or from one species of eukaryote to another species of eukaryote, or from bacteria to yeast then to animal cells, or from yeast to plants, or from plants to yeast, or from yeast to animal cells, or from animal cells to yeast, or from one type of animal cell to another type of animal cell from the same animal, or from one species of animal to another species of animal.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 9 is a table showing the edit category and the number of wells that were in each edit category obtained for the experiment described in Example 4.

It should be understood that the drawings are not necessarily to scale, and that like reference numbers refer to like features.

DETAILED DESCRIPTION

Figure 1:
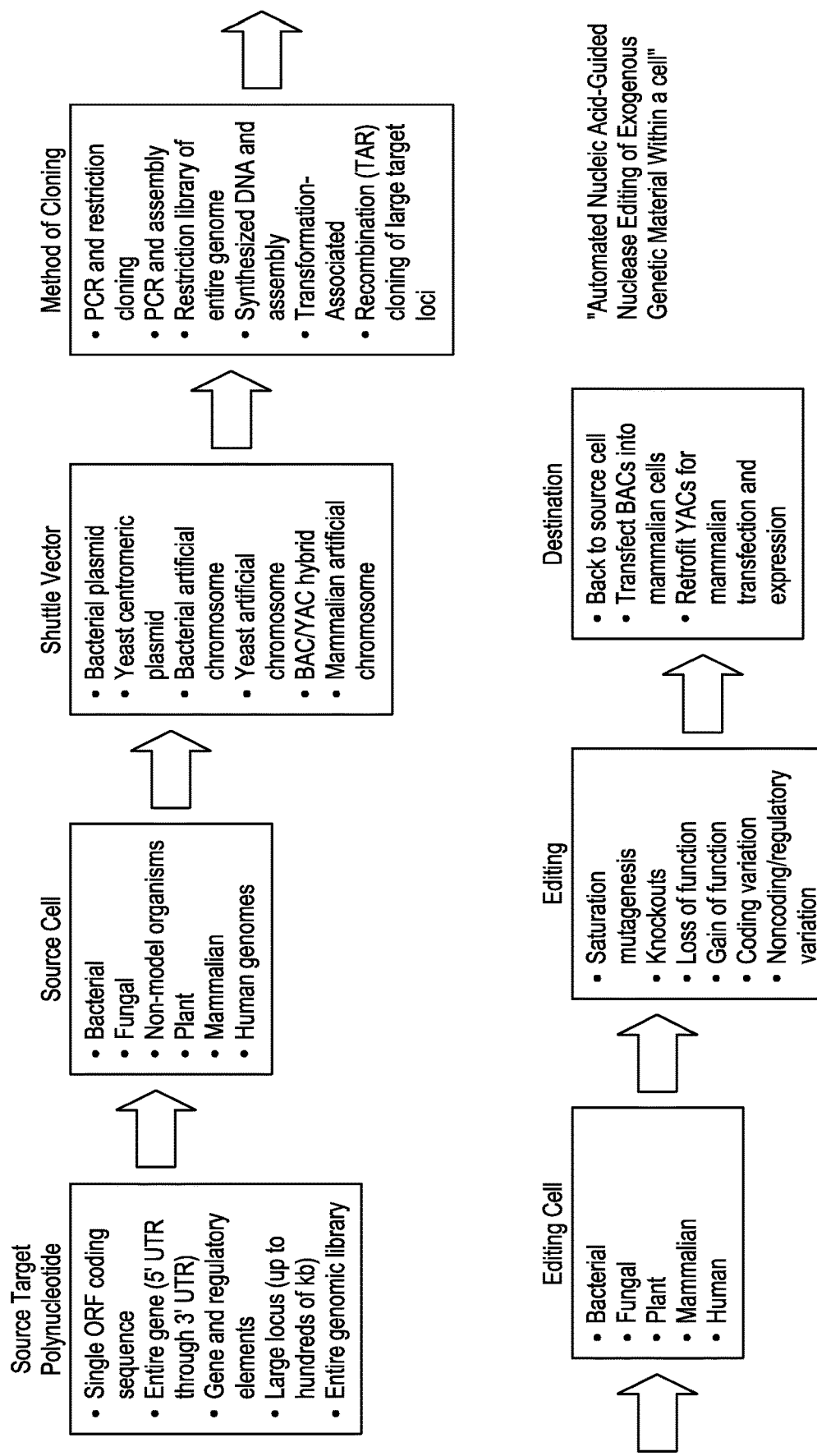
FIG. 1 is a process diagram showing the various pathways for building and editing shuttle vectors.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes. For techniques for creating synthetic chromosomes and cell transformation and growth, see *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011), both of which are herein incorporated by reference in their entirety for all purposes. Nucleic acid-guided nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

A "centromere" is any nucleic acid sequence that confers an ability of a chromosome to segregate to daughter cells through cell division. A centromere may confer stable segregation of a nucleic acid sequence, including a synthetic chromosome containing the centromere, through mitotic and meiotic divisions. A centromere does not necessarily need to be derived from the same species as the cells into which it is introduced, but preferably the centromere has the ability to promote DNA segregation in cells of that species. A "dicentric" chromosome is a chromosome that contains two centromeres. A "formerly dicentric chromosome" is a chromosome that is produced when a dicentric chromosome fragments. A "chromosome" is a nucleic acid molecule-and associated proteins-that is capable of replication and segregation in a cell upon division of the cell. Typically, a chromosome contains a centromeric region, replication origins, telomeric regions and a region of nucleic acid between the centromeric and telomeric regions. An "acrocentric chromosome" refers to a chromosome with arms of unequal length.

A "coding sequence" or a sequence that "encodes" a peptide is a nucleic acid molecule that is transcribed (in the case of DNA) and translated (in the case of mRNA) into a polypeptide in vivo when placed under the control of appropriate control sequences. The boundaries of the coding sequence typically are determined by a start codon at the 5' (amino) terminus and a translation stop codon at the 3' (carboxy) terminus.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components-translated in an appropriate host cell.

As used herein the term "donor DNA" or "donor nucleic acid" refers to nucleic acid that is designed to introduce a DNA sequence modification (insertion, deletion, substitution) into a locus (e.g., a target genomic DNA sequence or cellular target sequence) by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell-will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the genomic target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the genomic target sequence.

"Endogenous chromosomes" refer to chromosomes found in a cell prior to generation or introduction of exogenous genetic material.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein, the terms "protein" and "polypeptide" are used interchangeably. Proteins may or may not be made up entirely of amino acids.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione 5-transferase alpha (GSTA1; conjugates glutathione to the stem cell selective alkylator busulfan; chemoprotective selectable marker in CD34+ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); rhamnose, and Cytidine deaminase (CD; selectable by Ara-C). "Selective medium" as used herein refers to cell growth medium to which has been added a chemical compound or biological moiety that selects for or against selectable markers.

The term "specifically binds" as used herein includes an interaction between two molecules, e.g., an engineered peptide antigen and a binding target, with a binding affinity represented by a dissociation constant of about $10^{-7}$M, about $10^{-8}$M, about $10^{-9}$ M, about $10^{-10}$ M, about $10^{-11}$M, about $10^{-12}$M, about $10^{-13}$M, about $10^{-14}$M or about $10^{-15}$M.

"Synthetic chromosomes" (also referred to in the art as "artificial chromosomes") are nucleic acid molecules, typically DNA, that stably replicate and segregate alongside endogenous chromosomes in cells that have the capacity to accommodate and express heterologous genes. A "bacterial artificial chromosome (BAC)" is a DNA construct capable of extrachromosomal replication and segregation in bacterial cells. A "yeast artificial chromosome (YAC)" is a DNA construct capable of extrachromosomal replication and segregation in yeast cells. A "mammalian synthetic chromosome (MAC)" refers to chromosomes that have an active mammalian centromere(s). A "human synthetic chromosome (HAC)" refers to a chromosome that includes a centromere that functions in human cells and that preferably is produced in human cells. For exemplary artificial chromosomes, see, e.g., U.S. Pat. Nos. 8,389,802; 7,521,240; 6,025,155; 6,077,697; 5,891,691; 5,869,294; 5,721,118; 5,712,134; 5,695,967; and 5,288,625 and published International PCT application Nos. WO 97/40183 and WO 98/08964, all of which are herein incorporated by reference.

The terms "target genomic DNA sequence", "cellular target sequence", "target sequence", "target cellular locus" or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus. The term "edited target sequence" or "edited locus" refers to a target genomic sequence or target sequence after editing has been performed, where the edited target sequence comprises the desired edit.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, BACs, YACs, PACs, MACs, HACs, and the like. As used herein, the term "shuttle vector" refers to a vector that is meant to be used to transfer nucleic acids of interest between at least two different types of living cells, such as but not limited to a transfer of nucleic acids from one species of bacteria to another species of bacteria, from one species of yeast to another species of yeast, from one species of eukaryote to another species of eukaryote, from bacteria to yeast then to animal cells, from yeast to plants, from plants to yeast, from yeast to animal cells, from one type of animal cell to another type of animal cell from the same animal, from one species of animal to another species of animal, and any permutation or combination of these types of cells. In some embodiments of the present methods, two vectors—an engine vector, comprising the coding sequences for a nuclease, and an editing vector, comprising the gRNA sequence and the donor DNA sequence—are used. In alternative embodiments, all editing components, including the nuclease, gRNA sequence, and donor DNA sequence are all on the same vector (e.g., a combined editing/engine vector).

For the editing components, as used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto, as well as a selectable marker. As used herein the phrase "editing vector" comprises a donor nucleic acid, including an alteration to the target sequence which prevents nuclease binding at a PAM or spacer in the target sequence after editing has taken place, and a coding sequence for a gRNA under the control of a promoter. The editing vector may also comprise a selectable marker and/or a barcode. In some embodiments, the engine vector and editing vector may be combined; that is, the contents of the engine vector may be found on the editing vector such that all components of the exogenous "editing machinery" are on a single vector.

Nucleic Acid-Guided Nuclease Editing in Shuttle Vectors

Source Genomic Loci

The source polynucleotides for automated nucleic acid-guided nuclease editing within a heterologous editing cell may be of varying size. For interrogating the function of a single gene, it may be desirable to edit only the protein-coding sequence of said gene. To enable editing of the protein-coding sequence of a gene, in some implementations, the open reading frame (ORF) beginning with the initiation codon, ending with the termination codon, and lacking introns, is introduced on a shuttle vector to heterologous editing cells for automated nucleic acid-guided nuclease editing. This coding sequence is typically preceded by one of any number of desired promoters and followed by one of any number of terminator sequences. Varieties of edits to the coding sequence of a single gene may include saturation mutagenesis, premature termination codons, missense mutations, nonsense mutations, synonymous mutations, loss of function mutations, gain of function mutations, or insertions or deletions (indels) of size ranging from 1-10 nucleotides (nt), 5-50 nt, 25-100 nt, 50-500 nt, 100-1000 nt, 500-5000 nt, 1000-10,000 nt, 5000-50,000 nt, or greater. In addition, source polynucleotides may be a chemically-synthesized sequence derived from or inspired by (e.g., codon-optimized, gene-fusions, operon refactoring, sequence constructs of mixed heterologous organism sources, or cDNAs) a naturally-occurring sequence and delivered into the shuttle vector or editing host as "synthetic" DNA.

To interrogate the function of an entire gene including its introns and untranslated regions, in some implementations, the entire nucleotide sequence of a gene, coding and non-coding, is included in the shuttle vector for automated nucleic acid-guided nuclease editing within heterologous editing cells. Exons, introns, and the borders between exons and introns contain information to direct accurate splicing after transcription. These include exonic splicing enhancer sequences, intronic splicing enhancer sequences, and alternative splicing donor and acceptor sequences. Furthermore, noncoding regions of genes, including introns, may encode functional noncoding RNAs, which may be a desirable target polynucleotide for editing. These may include microRNAs, short interfering RNAs, piwi-interacting RNAs, or long noncoding RNAs. The 5' untranslated regions (UTRs) of genes include essential regulatory elements that direct processes related to transcription, translation, mRNA export, and mRNA structure. The 3' UTRs of genes have essential roles in regulation of transcription, translation, mRNA stability, polyadenylation, translation efficiency, post-transcriptional regulation of gene expression, and sometimes contain microRNA response elements. For all these reasons, noncoding regions of genes including the 5' UTR, introns, and 3' UTRs may be desirable target polynucleotides for automated nucleic acid-guided nuclease editing within heterologous editing cells.

Genes are often subjected to long-range regulation exceeding the boundaries of their 5' and 3' UTRs. Long-range acting regulatory elements may include enhancers, repressors, insulators, or mediators of long-range epigenetic activation or silencing. For the purposes of interrogating the function of a gene including its long-range regulatory elements, in some implementations, a relatively large segment of exogenous genetic material is subjected to automated nucleic acid-guided nuclease editing within living cells. Thus, capturing a locus exceeding the boundaries of a gene, of size 100-1000 nt, 500-5000 nt, 1000-10,000 nt, 5000-50,000 nt, 10,000-100,000 nt, 50,000-500,000 nt, 100-1,000,000 nt, 500,000-5,000,000 nt in a shuttle vector for automated nucleic acid-guided nuclease editing within heterologous cells may be desirable. Such a large locus will include coding regions, noncoding regions, and regulatory elements of one or many genes and may be subjected to any of the same sorts of mutagenesis experiments as described above.

Alternatively, in some implementations, an entire exogenous genome may be subjected to automated nucleic acid-guided nuclease editing within heterologous editing cells. An entire genome may be introduced to a shuttle vector in the form of a library. The choice of shuttle vector to be used may be determined based on the destination and application (discussed infra). Methods of introduction of the genomic library to the shuttle vector may be determined based on one or more of source cells and genome, destination, and application (discussed infra). Automated nucleic acid-guided nuclease editing of an entire exogenous genome allows for systematic genome-wide screens of gene function, gene-by-gene interactions, suppressor screens, user-directed evolution, genome-wide screens for genes affecting a particular phenotype, forward genetic screens, among many other experimental approaches.

Source Genomes

Exogenous polynucleotides for automated nucleic acid-guided nuclease editing within heterologous editing cells, in the various embodiments described herein, may be derived from the genomes of any number of source prokaryotic or eukaryotic organisms, including bacteria, fungi, protists, worms, insects, amphibians, fish, or mammals. The following paragraphs discuss examples of source genomes as well as some methods and considerations in preparing material from such genomes for introduction into an automated nucleic acid-guided nuclease editing system.

Many bacterial species are useful for commercial or biomedical applications, or as subjects of basic, translational, or clinical scientific inquiry. Thus, genes and genomic loci (described above) found in bacterial genomes and plasmids are attractive targets for automated nucleic acid-guided nuclease editing within living cells. As described above, target loci may range in size from single genes, to large multi-gene loci, to entire bacterial genomes. Commercial applications of bacterial genes and pathways include production of surfactants (Desai & Banat, Fuel Energy Abstr, 38(4):221 (1997)), production of biofuels (Peralta-Yahya, et al., Nature, 488(7411):320-328 (2012)), novel production methods for commodity and specialty compounds (Steen, et al., Nature, 463(7280):559-562 (2010)), biosynthesis of pharmaceutically-useful compounds (Yuzawa, et al., Biochemistry, 51(49):9779-9781 (2012)), or as bioremediation agents (U.S. Pat. No. 8,440,423).

Source bacterial species from which genetic material may be derived for automated nucleic acid-guided nuclease editing include, but are not limited to, *Escherichia coli, Shewanella oneidensis, Bacillus subtilis, Micrococcus luteus, Streptomyces aizunensis, Mycobacterium tuberculosis, Streptomyces coelicolor, Mycobacterium smegmatis, Pseudomonas putida, Desulfovibrio vulgaris, Lactobacillus acidophilus, Corynebacterium glutamicum, Bacillus thuringiensis, Acetobacter aceti, Klebsiella pneumoniae*, and *Methylococcus capsulatus*.

Most bacterial genomes include a single closed loop of nucleic acid sequence between approximately 500,000 nucleotides and 10,000,000 nucleotides in length. Genomic DNA may be prepared by standard techniques and target loci may be amplified or isolated and introduced to shuttle vectors according to techniques discussed supra. Alternatively, target loci may reside on bacterial plasmid DNA. Plasmid DNA may be prepared by standard techniques and target loci are amplified or isolated and introduced to shuttle vectors according to techniques discussed supra. For both genomic targets and plasmid targets, the choice of shuttle vector depends on target size, destination, and application.

Like bacteria, fungal organisms are useful for industrial applications, biomedical and biopharmaceutical applications, and as tools for basic, translational, and clinical research. Fungal genes and genomes have been utilized in the discovery and biosynthesis of natural products (Luo, et al., Curr Opin Biotechnol., 30:230-237 (2014)), biofuels (Runguphan & Keasling, Metab Eng., 21:103-113 (2014)), pharmaceutical compounds (Punt, et al., TRENDS Biotechnol., 20(5):200-206 (2002)), and as agents in bioremediation (U.S. Pat. No. 6,150,157). As described above, target loci may range in size from single genes, to large multi-gene loci, to entire fungal genomes. Genes, multi-gene loci, and genomes of many fungal organisms present attractive target polynucleotides for automated nucleic acid-guided nuclease editing in heterologous cells.

Source fungal species from which genetic material may be derived for automated nucleic acid-guided nuclease editing include, but are not limited to, *Saccharomyces cerevisiae, Schizosaccharomyces pombe, Aspergillus oryzae, Aspergillus terreus, Aspergillus niger, Aspergillus nidulans, Trichoderma reesei, Fusarium venenatum, Cephalosporium* sp., *Penicillium* sp., *Neurospora crassa, Yarrowia lipolytica, Pichia pastoris*, and *Phanerochaete chrysosporium*.

Protists are a diverse group of unicellular eukaryotic microorganisms including flagellates, ciliates, amoebae, sporozoae, some algae, and slime molds. One genus of slime molds in particular, *Dictyostelium* has been useful as a model laboratory organism, of which the species *D. discoideum* is the best-studied. *Dictyostelium* are commonly used to study biological processes including cell differentiation, chemotaxis, apoptosis, thermotaxis, and as a model for *Legionella* infection. *Dictyostelium* represents a laboratory model that is intermediate in complexity between eukaryotic unicellular fungi such as *S. cerevisiae*, and more complex multicellular eukaryotic genomes. The *Dictyostelium* genome contains orthologs of human disease genes which are useful for studying pathophysiological processes including cellular differentiation and cancer metastasis and invasion. The *Dictyostelium* genome also contains an abundance of genes encoding polyketide synthases (Eichinger, et al., Nature, 435(7038):43-57 (2005)), proteins essential to the biosynthesis and export of many natural products including some antibiotics and anticancer agents. As a useful model organism, *Dictyostelium* genes, multi-gene loci, and genomes are attractive target polynucleotides for automated nucleic acid-guided nuclease editing in heterologous cells. Genomic DNA may be isolated according to standard techniques (Pilcher, et al., Nat Protoc, 2(6):1325-1328 (2007)) and target loci may be amplified or isolated and introduced to shuttle vectors according to techniques described below. Choice of shuttle vector depends on target size, destination, and application.

Increasingly complex multicellular eukaryotes introduce distinct advantages as model organisms in the laboratory and the genes, multi-gene loci, and genomes of these organisms are thus target polynucleotides for automated nucleic acid-guided nuclease editing in heterologous cells. The roundworm *Caenorhabditis elegans* is a simple multicellular eukaryote that has been studied extensively as a model organism. The 959 cells of the adult worm have been comprehensively lineage-mapped and its simple nervous system has been a model for neuronal differentiation and innervation. The worms' advantages as a model organism include are low cost and ease of culturing and propagation, they are transparent, can be frozen and remain viable upon thawing, and are nonpathogenic. The genes, multi-gene loci, and genomes of *C. elegans* and other simple multicellular eukaryotes are possible target polynucleotides for automated nucleic acid-guided nuclease editing in heterologous cells.

The genome of *C. elegans* is 97 Mb in size and is predicted to contain approximately 19,000 genes, many of which find homologs in more complex eukaryotes including humans (The *C. elegans* Sequencing Consortium, Science, 282(5396):2012-2018 (1998)). Genomic DNA may be isolated according to standard techniques and target loci are amplified or isolated and introduced to shuttle vectors according to techniques described below. The choice of shuttle vector depends on target size, destination, and application.

Several insect species have been useful as model laboratory organisms and insects as a subphylum include more than one million described species and include more than half of all known living organisms. Insects have significant roles and uses in agriculture, industry, ecology, and as vectors for human disease, and thus insect genes, multi-gene loci, and genomes are possible target polynucleotides for automated nucleic acid-guided nuclease editing in heterologous cells.

In the laboratory, the fly species *Drosophila melanogaster* has played a critical role in the study of genetics, physiology, evolution, cellular differentiation and development, and microbial pathogenesis. *Drosophila*'s advantages as a model organism include short generation time, low cost propagation and colony maintenance, and prolific laying of macroscopically visible and manipulatable eggs. Laboratory derived mutant strains have easily traceable phenotypes that allow for robust study of Mendelian genetics.

The genome of *Drosophila melanogaster* is approximately 140 Mb in size and contains four pairs of chromosomes and approximately 14,000 protein-coding genes (Halligan and Keightley, Genome Res. 16(2001):875-884 (2006)). Genomic DNA may be isolated according to standard techniques and target polynucleotides may be amplified or isolated and introduced to shuttle vectors according to techniques described below. The choice of shuttle vector depends on target size, destination, and application.

In addition to *Drosophila melanogaster* the genes, multi-gene loci, and genomes of many other insects may be attractive target polynucleotides for automated nucleic acid-guided nuclease editing in heterologous cells. Many mosquito species are vectors for human disease and may be targets for editing, including, but not limited to genera *Aedes, Anopheles, Culex, Culiseta, Mansonia, Coquillettidia, Psorophora,* and *Toxorhynchites*. Agriculturally important insects include, but are not limited to, the Brown Marmorated Stinkbug (*Halyomorpha halys*), Agrican Fig Fly (*Zaprionus indianus*), Western Bean Cut Worm (*Richia albicosta*), Spotted Wing *Drosophila* (*Drosophila suzukii*), Elm Bark Beetles (genera *Hylurgopinus, Scolytus,* and *Pteleobius*), and other insects that are either advantages or disadvantages to agriculture.

Several mammalian species have been indispensable research tools as model organisms for studying human disease. As higher order eukaryotes with increasingly complex genomes, mammalian species share homologous genes and are far better tools for interrogating the immune, endocrine, nervous, cardiovascular, skeletal and other complex physiological systems that mammals share, than are simpler model organisms. Mice, dogs, and other species naturally develop disease phenotypes affecting humans, including cancer, atherosclerosis, hypertension, diabetes, osteoporosis, glaucoma, among others. Model organisms can also be manipulated genetically to induce models of human disease. Several mammalian species are also of commercial and agricultural interest. Thus, mammalian genes, multi-gene loci, and genomes are possible target polynucleotides for automated nucleic acid-guided nuclease editing in heterologous cells.

The mouse (*Mus musculus*) genome is approximately 2,700 Mb is size, contains twenty pairs of chromosomes, and approximately 20,000-25,000 protein-coding genes (Mouse Genome Sequencing Consortium, et al., Nature, 420(6915): 520-562 (2002)). The chimpanzee (*Pan troglodytes*) genome is approximately 2,900 Mb in size, contains, 24 pairs of chromosomes, and approximately 20,000-25,000 protein-coding genes (The Chimpanzee Sequencing and Analysis Consortium, et al., Nature, 437(7055):69-87 (2005)). The domestic dog (*Canus lupus familiaris*) genome is approximately 2,500 Mb in size, contains 39 pairs of chromosomes, and approximately 20,000-25,000 protein-coding genes (Lindblad-Toh et al., Nature, 438(7069):803-819 (2005). The domestic pig (*Sus scrofa*) genome is approximately 2,600 Mb in size, contains 19 pairs of chromosomes, and approximately 20,000-25,000 protein-coding genes (Groenen et al., Nature, 491(7424):393-398 (2012)). The domestic cow (*Bos Taurus*) genome is approximately 2,900 Mb in size, contains 30 pairs of chromosomes, and approximately 22,000 protein-coding genes (Liu et al., BMC Genomics, 10:1-11 (2009)).

Mammalian genomic DNA may be isolated according to standard techniques and target polynucleotides may be amplified or isolated and introduced to shuttle vectors according to techniques described below. Choice of shuttle vector depends on target size, destination, and application.

Isolating and characterizing the structure or function of human genes and the human genome are useful research tools for elucidating the cause of human disease and as a guide for developing therapies. Thus, human genes, multi-gene loci, and the human genome are possible target polynucleotides for automated nucleic acid-guided nuclease editing in heterologous cells. The human genome is approximately 3,200 Mb in size, contains 23 pairs of chromosomes, and approximately 20,000-25,000 protein-coding genes (International Human Genome Sequencing Consortium, et al., Nature, 431(7011):931-945 (2004)).

Human genomic DNA may be isolated according to standard techniques and target polynucleotides may be amplified or isolated and introduced to shuttle vectors according to techniques described below. Choice of shuttle vector depends on target size, destination, and application.

For all the organisms described herein of which genes, multi-gene loci, and genomes are possible target polynucleotides of automated nucleic acid-guided nuclease editing in heterologous cells, the mitochondrial genome, when applicable, is also a possible target polynucleotide.

Shuttle Vectors

It may be necessary to use various shuttle vectors in order to introduce exogenous polynucleotides from a source cell or genome into heterologous editing cells for automated nucleic acid-guided nuclease editing. Selection of an appropriate shuttle vector depends on the size of the payload, the source genome, the source locus, the heterologous cells in which automated editing takes place, and the eventual destination of edited sequences. The following paragraphs discuss example shuttle vectors as well as some methods and considerations for use thereof in shuttling exogenous polynucleotides from the source to the heterologous editing cells in which automated editing occurs.

In some implementations, a bacterial plasmid may be used as a shuttle vector to introduce exogenous polynucleotides from a source locus (or loci) into heterologous editing cells for automated nucleic acid-guided nuclease editing. Plasmids are closed circular DNA molecules that are comparatively small relative to bacterial genomes and are genetic elements that may exist outside of the genomic chromosome and can replicate autonomously. Bacterial plasmids typically comprise certain features—natural or engineered—that make them useful for introducing exogenous nucleic acids into cells (Casali & Preston, *Plasmid Vectors* (Humana Press) (2003)). For example, useful bacterial plasmids comprise an origin of replication to propagate and maintain plasmid copy number throughout host cell division, such as the pMB1, pBR322, ColE1, R6K, p 15A, pSC101 ColE1, F1, or pUC origin of replication, among others.

Useful bacterial plasmid shuttle vectors also typically comprise an antibiotic resistance gene for use as a selectable marker, allowing for detection of plasmid-containing cells when grown in or on a selective growth medium. For example, a bacterial plasmid may contain a gene conferring resistance to kanamycin, spectinomycin, streptomycin, ampicillin, carbenicillin, bleomycin, erythromycin, polymyxin B, tetracycline, or chloramphenicol, among others.

Useful bacterial plasmid shuttle vectors may also comprise a multiple cloning site or "polylinker" region. A polylinker is a segment of nucleotide sequence within the plasmid which contains many—e.g., up to ~20—restriction sites for recognition by restriction endonucleases. The restrictions sites within the polylinker may be unique, i.e. only occur once within the sequence of the circular plasmid. Inserts may be conveniently introduced to the shuttle vector by means of the unique restriction site and conventional "sticky end" cloning, discussed supra.

Bacterial plasmid shuttle vectors may accommodate an inserted target polynucleotide of size 1-100 nucleotides (nt), 50-500 nt, 100-1000 nt, 500-5000 nt, 1000-10,000 nt, or 5000-50,000 nt.

In other implementations, yeast plasmids may be used as shuttle vectors to introduce exogenous polynucleotides from a source cell into heterologous editing cells for automated nucleic acid-guided nuclease editing. Similar to bacterial plasmids, yeast plasmids are closed circular DNA molecules that are comparatively small relative to the linear chromosomes of the yeast genome. As with bacterial plasmids, there are certain features that are included in yeast plasmids (naturally-occurring or engineered) that make yeast plasmids useful for introducing exogenous polynucleotides into heterologous editing cells.

In some implementations a yeast centromeric plasmid may be used as a shuttle vector. Yeast centromeric plasmids contain two requisite features: autonomously replicating sequences (ARS) and centromeric (CEN) sequences. Yeast centromeric plasmids exploit the host cell's endogenous replication and chromosome segregation machinery to persist in yeast cells like mini-chromosomes. The ARS feature functions similarly to the bacterial origin of replication described above and allows for independent propagation of the plasmid in cells. The CEN sequence is the attachment point for kinetochore complexes and allows for faithful segregation of copies of the plasmid to daughter cells during mitosis. Both the ARS and CEN sequences are required for stable maintenance and correct distribution of a yeast centromeric plasmid during cell division. Yeast CEN plasmids are maintained at about 1 copy per cell per haploid genome, when averaged across the cell populations, although plasmid copy number within individual cells may vary (Gnugge and Rudolf, Yeast, 34(4):205-221 (2017)).

In addition to the ARS and CEN sequences, a yeast centromeric plasmid may contain a polylinker region (discussed supra) and may contain one or more selectable markers. Yeast shuttle vectors may be maintained in culture by auxotrophic selection, markers for which may include, but are not limited to, URA3, LEU2, HISS, TRP1, ADE2, LYS2, or MET15. Autoselection systems may include, but are not limited to, URA3, FBAI, POT/TPI, or CDCx. Dominant selectable marker genes may include, but are not limited to, kan, hph, nat, pat, ble, amdSYM, or tk.

Yeast plasmid shuttle vectors may accommodate an inserted target polynucleotide of size 1-100 nucleotides (nt), 50-500 nt, 100-1000 nt, 500-5000 nt, 1000-10,000 nt, or 5000-50,000 nt.

In some implementations, a plasmid shuttle vector may be suited for use in both *E. coli* cells and yeast cells, having properties of both bacterial and yeast plasmids. In some implementations target sequences may be constructed, manipulated, analyzed, cloned, expanded, propagated, edited, transformed into, and isolated out of both bacterial cells and yeast cells. Such a shuttle vector may require a combination of the following (all of which are discussed infra): bacterial origin of replication; marker for selection in bacterial cells; yeast ARS; yeast CEN sequence; marker for selection in yeast cells; and a polylinker sequence.

In some implementations—in particular for isolating and delivering larger genomic loci or entire genomes to heterologous editing cells for automated nucleic acid-guided nuclease editing—non-plasmid shuttle vectors may be more appropriate. The paragraphs below discuss various classes of artificial chromosomes as well as some methods and considerations for use in shuttling exogenous polynucleotides from a source cell or genome to the heterologous editing cells in which automated editing occurs.

Bacterial artificial chromosomes (BACs) are DNA constructs capable of accommodating larger inserts than plasmids. Similar circular cloning shuttle vectors called PACs are derived from the DNA of P1 bacteriophage. BACs and PACs have the advantage of being able to capture large genomic segments up to approximately 350 kilobases, thereby facilitating the cloning of entire genes including noncoding regions and regulatory elements. Hallmark features of BACs and PACs include, but are not limited to, a P1 or F origin of replication; an antibiotic resistance gene which may be one of several genes conferring resistance to kanamycin, spectinomycin, streptomycin, ampicillin, carbenicillin, bleomycin, erythromycin, polymyxin B, tetracycline, or chloramphenicol, among others; a parA and/or parB sequence for partitioning F plasmid DNA to daughter cells during cell division; and a polylinker region. A suitable BAC or PAC vector backbone may accommodate an entire gene or other large locus, or a library of inserts generated from a fractionated genome. Methods and considerations for introducing large inserts into BAC and PAC shuttle vectors are discussed supra.

BAC and PAC shuttle vectors may accommodate an inserted target polynucleotide of size 10,000-50,000 nucleotides (nt), 30,000-100,000 nt, 50,000-300,000 nt, or 100,000-500,000 nt.

Similar to BACs, yeast artificial chromosomes (YACs) may be used as shuttle vectors to accommodate relatively large payloads of polynucleotides. In some implementations YACs may be preferable to BACs for the cloning and shuttling of exogenous polynucleotides into heterologous editing cells for automated nucleic acid-guided nuclease editing. Hallmark features of YACs may include, but are not limited to, an ARS sequence (discussed supra) to allow the YAC to replicate autonomously and extrachromosomally; CEN sequences (discussed supra) to confer mitotic stability and allow for faithful segregation and maintenance of copy number during cell division; a selectable marker which may include, but is not limited to, URA3, LEU2, HISS, TRP1, ADE2, LYS2, or MET15, an autoselection system URA3, FBAI, POT/TPI, or CDCx, or a dominant selectable marker gene may including, kan, hph, nat, pat, ble, amdSYM, or tk. YACs may accommodate relatively large polynucleotide insert sizes up to 3000 kb in length (Dunnen, et al., Hum Mol Genet, 1(1):19-28 (1992)).

YAC shuttle vectors may accommodate an inserted target polynucleotide of size 10,000-50,000 nucleotides (nt), 30,000-100,000 nt, 50,000-300,000 nt, 100,000-1,000,000 nt, or 300,000-3,000,000 nt.

In some implementations, it may be desirable to use an artificial chromosome shuttle vector that shares features of both bacterial and yeast artificial chromosomes; for example, when a genomic locus is introduced into a YAC by transformation-associated recombinational (TAR) cloning in yeast (discussed infra) but propagation and rapid large-scale DNA preparation in bacteria is desired. Such an artificial chromosome may contain a yeast CEN sequence, yeast ARS sequence, marker for selection in yeast, marker for selection in bacteria, and bacterial origin of replication, along with the insert of an exogenous polynucleotide that is the target of automated nucleic acid-guided nuclease editing (Bhargava, et al., Genomics, 62(2):285-288 (1999)). In some implementations, it may be desirable to retrofit a target polynucleotide-carrying YAC into a BAC, e.g. for the purposes of simplified preparation of large quantities of shuttle vector DNA, for downstream transfection into mammalian cells, or for performing automated nucleic acid-guided nuclease editing of target polynucleotides cloned in YACs in bacterial editing cells rather than yeast editing cells. Retrofitting may be accomplished by transforming the YAC-containing yeast strain with a restriction-digestion linearized retrofitting plasmid. The retrofitting plasmid may contain a yeast selectable marker, a mammalian selectable marker, the F-factor origin of replication, and an antibiotic resistance gene. Recombination between the retrofitting vector and the YAC is mediated by two short targeting sequences with homology to the YAC. After recombination the resulting BAC contains the target polynucleotide previously carried on the YAC (see US Pub. No. 2004/0245317).

The ability to generate fully-functional mammalian artificial chromosomes represents a powerful system for cell-based correction of genetic disorders, production of recombinant proteins in transgenic animals, analysis of regulation and expression of large human genes in a variety of cell types as well as in animal models of human disease, studies of meiosis and chromosome structure, directing cell differentiation and dedifferentiation, formation of induced pluripotent stem cells, and manipulation of large DNA elements such as but not limited to chromosome arm exchange onto the synthetic chromosome or incorporation of multiple large DNA elements onto the artificial chromosome. Fully-functional mammalian artificial chromosomes offer several advantages over viral-based delivery systems including increased payload size, the fact that extrachromosomal maintenance avoids potential host-cell disruption, avoidance of transcriptional silencing of introduced genes and possible immunological complications, and mammalian artificial chromosomes can be derived from and tailored to the species into which the artificial chromosome is to be inserted, e.g. mouse, human.

The synthetic chromosome shuttle vectors and the methods and automated multi-module cell editing instruments are applicable to all currently-employed methods of artificial chromosome production, including the "top down", "bottom up", engineering of minichromosomes, and induced de novo chromosome generation methods used in the art. The "bottom up" approach of artificial chromosome formation relies on cell-mediated de novo chromosome formation following transfection of a permissive cell line with cloned α-satellite sequences, which comprise typical host cell-appropriate centromeres and selectable marker gene(s), with or without telomeric and genomic DNA. (For protocols and a detailed description of these methods see, e.g., Harrington, et al., Nat. Genet., 15:345-55 (1997); Ikeno, et al., Nat. Biotechnol., 16:431-39 (1998); Masumoto, et al., Chromosoma, 107:406-16 (1998), Ebersole, et al., Hum. Mol. Gene., 9:1623-31 (2000); Henning, et al., PNAS USA, 96:592-97 (1999); Grimes, et al., EMBO Rep. 2:910-14 (2001); Mejia, et al., Genomics, 79:297-304 (2002); and Grimes, et al., Mol. Ther., 5:798-805 (2002).) Both synthetic and naturally-occurring α-satellite arrays, cloned into yeast artificial chromosomes, bacterial artificial chromosomes or P1-derived artificial chromosome shuttle vectors have been used in the art for de novo mammalian artificial chromosome formation. The products of bottom up assembly can be linear or circular, comprise simplified and/or concatemerized input DNA with an α-satellite DNA based centromere, and typically range between 1 and 10 Mb in size. Bottom up-derived artificial chromosomes also are engineered to incorporate nucleic acid sequences that permit site-specific integration of target DNA sequence onto the artificial chromosome.

The "top down" approach of producing mammalian artificial chromosomes involves sequential rounds of random and/or targeted truncation of pre-existing chromosome arms to result in a pared down artificial chromosome comprising a centromere, telomeres, and DNA replication origins. (For protocols and a detailed description of these methods see, e.g., Heller, et al., PNAS USA, 93:7125-30 (1996); Saffery, et al., PNAS USA, 98:5705-10 (2001); Choo, Trends Mol. Med., 7:235-37 (2001); Barnett, et al., Nuc. Ac. Res., 21:27-36 (1993); Fan, et al., PNAS USA, 88:7006-10 (1991); and Katoh, et al., Biochem. Biophys. Res. Commun., 321:280-90 (2004).) "Top down" artificial chromosomes are constructed optimally to be devoid of naturally-occurring expressed genes and are engineered to contain DNA sequences that permit site-specific integration of target DNA sequences onto the truncated chromosome, mediated, e.g., by site-specific DNA integrases.

A third method for producing artificial chromosomes known in the art is engineering of naturally occurring minichromosomes. This production method typically involves irradiation-induced fragmentation of a chromosome containing a functional, e.g., human neocentromere possessing centromere function yet lacking α-satellite DNA sequences and engineered to be devoid of non-essential DNA. (For protocols and a detailed description of these methods see, e.g., Auriche, et al., EMBO Rep. 2:102-07 (2001); Moralli, et al., Cytogenet. Cell Genet., 94:113-20 (2001); and Carine, et a., Somat. Cell Mol. Genet., 15:445-460 (1989).) As with other methods for generating artificial chromosomes, engineered minichromosomes can be engineered to contain DNA sequences that permit site-specific integration of target DNA sequences.

The fourth approach for production of artificial chromosomes involves induced de novo chromosome generation by targeted amplification of specific chromosomal segments. This approach involves large-scale amplification of pericentromeric/ribosomal DNA regions situated on acrocentric chromosomes. The amplification is triggered by co-transfection of excess DNA specific to the pericentric region of chromosomes, such as ribosomal RNA, along with DNA sequences that allow for site-specific integration of target DNA sequences and also a drug selectable marker which integrates into the pericentric regions of the chromosomes. (For protocols and a detailed description of these methods see, e.g., Csonka, et al., J. Cell Sci 113:3207-16 (2002); Hadlaczky, et al., Curr. Opini. Mol. Ther., 3:125-32 (2001); and Lindenbaum and Perkins, et al., Nuc. Ac. Res., 32(21): e172 (2004).) During this process, targeting to the pericentric regions of acrocentric chromosomes with co-transfected DNA induces large-scale chromosomal DNA amplification, duplication/activation of centromere sequences, and subsequent breakage and resolution of dicentric chromosomes resulting in a "break-off" satellite DNA-based synthetic chromosome containing multiple site-specific integration sites.

In some embodiments, the cells used to produce the artificial chromosome may be the heterologous editing cell; that is, the heterologous editing cell can be used—and preferably is used—for both synthetic chromosome construction and editing. Alternatively, the cells to produce the artificial chromosome (and, in some embodiments, to edit the artificial chromosomes) can be cells that naturally occur in a subject (human patient, animal or plant) in which the genes or regulatory sequences from the artificial chromosome will ultimately be expressed. Such cells can be primary-culture cell lines established for the purpose of artificial chromosome production specific for an individual. In other embodiments, the cells to produce the artificial chromosome and, in some embodiments, to edit the artificial chromosomes) are from an established cell line. A wide variety of cell lines for tissue culture are known in the art. Examples of cell lines include but are not limited to human cells lines such as 293-T (embryonic kidney), 721 (melanoma), A2780 (ovary), A172 (glioblastoma), A253 (carcinoma), A431 (epithelium), A549 (carcinoma), BCP-1 (lymphoma), BEAS-2B (lung), BR 293 (breast), BxPC3 (pancreatic cancinoma), Cal-27 (tongue), COR-L23 (lung), COV-434 (ovary), CML T1 (leukemia), DUI45 (prostate), DuCaP (prostate), FM3 (lymph node), H1299 (lung), H69 (lung), HCA2 (fibroblast), HEK0293 (embryonic kidney), HeLa (cervix), HL-60 (myeloblast), HMEC (epithelium), HT-29 (colon), HUVEC (umbilical vein epithelium), Jurkat (T cell leukemia), JY (lymphoblastoid), K562 (lymphoblastoid), KBM-7 (lymphoblastoid), Ku812 (lymphoblastoid), KCL22 (lymphoblastoid), KGI (lymphoblastoid), KYO1 (lymphoblastoid), LNCap (prostate), Ma-Mel (melanoma), MCF-7 (mammary gland), MDF-10A (mammary gland), MDA-MB-231, -468 and -435 (breast), MG63 (osteosarcoma), MOR/0.2R (lung), MONO-MAC6 (white blood cells), MRCS (lung), MSU1.1 (fibroblast), NCI-H69 (lung), NALM-1 (peripheral blood), NW-145 (melanoma), OPCN/OPCT (prostate), Peer (leukemia), Raji (B lymphoma), Saos-2 (osteosarcoma), Sf21 (ovary), Sf9 (ovary), SiHa (cervical cancer), SKBR3 (breast carcinoma), SKOV-2 (ovary carcinoma), T-47D (mammary gland), T84 (lung), U373 (glioblastoma), U87 (glioblastoma), U937 (lymphoma), VCaP (prostate), WM39 (skin), WT-49 (lymphoblastoid), and YAR (B cell). Rodent cell lines of interest include but are not limited to 3T3 (mouse fibroblast), 4T1 (mouse mammary), 9L (rat glioblastoma), A20 (mouse lymphoma), ALC (mouse bone marrow), B16 (mouse melanoma), B35 (rat neuroblastoma), bEnd.3 (mouse brain), C2C12 (mouse myoblast), C6 (rat glioma), CGR8 (mouse embryonic), CT26 (mouse carcinoma), E14Tg2a (mouse embryo), EL4 mouse leukemia), EMT6/AR1 (mouse mammary), Hepa1c1c7 (mouse hepatoma), J558L (mouse myeloma), MC-38 (mouse adenocarcinoma), MTD-1A (mouse epithelium), RBL (rat leukemia), RenCa (mouse carcinoma), X63 (mouse lymphoma), YAC-1 (mouse Be cell), BHK-1 (hamster kidney), and CHO (hamster ovary). Plant cell lines of use include but are not limited to BY-2, Xan-1, GV7, GF11, GT16, TBY-AtRER1B, 3n-3, and G89 (tobacco); VR, VW, and YU-1 (grape); PAR, PAP, and PAW (pokeweed); Spi-WT, Spi-1-1, and Spi12F (spinach); PSB, PSW and PSG (sesame); A.per, A.pas, A.plo (asparagus); Pn and Pb (bamboo); and DG330 (soybean); embryonic cell lines; pluripotent cell lines; adult derived stem cells; reprogrammed cell lines; generic animal cell lines of any species or broadly embryonic or reprogrammed cells; zebra fish cell lines; primary dog cells; primary horse cells; chicken DT40 cells; dog cell lines; cat cell lines; patient cell lines; and, in some preferred embodiments, the HT1080 human cell line is utilized. Potential cells of use include any living cell, but those from eukaryotes are specifically contemplated. These cell lines and others are available from a variety of sources known to those with skill in the art (see, e.g., the American Type Culture Collection (ATCC) (Manassas, Va.)).

In some implementations, it may be desirable to insert the edited target polynucleotide carried by a YAC or BAC shuttle vector into a mammalian artificial chromosome. For example, the target nucleotide may be a mammalian gene cloned into a BAC or YAC shuttle vector, subjected to automated nucleic acid-guided editing in heterologous editing cells, with a downstream application including expression in a human cell line. The BAC or YAC shuttle vector may be designed to include a loxP recombination site, and the mammalian artificial chromosome may be designed to include a loxP recombination site. The edited polynucleotide is loaded onto the mammalian artificial chromosome by Cre-loxP mediated recombination. The YAC or BAC may be co-transfected with a Cre-recombinase expression vector into mammalian cells carrying the mammalian artificial chromosome. The product of this recombination may be a mammalian artificial chromosome containing the edited target polynucleotide.

FIG. 1 is a process diagram showing the various options or pathways for selecting, building and editing shuttle vectors. The source target polynucleotides may be, as described above, e.g., an open reading frame coding sequence, several to many genes in a biochemical pathway, one or more noncoding regions, a large genomic locus, or an entire genome. The source cell may be bacterial cells, fungal cells, non-model organism cells, plant cells, and mammalian cells, including human cells. Also as described above, the shuttle vector itself can be, e.g., a bacterial plasmid, a viral vector, a yeast plasmid, a YAC, a BAC, hybrids of these, or artificial chromosomes, including mammalian artificial chromosomes. The construction of the vector and artificial chromosomes and the cloning of the source target polynucleotide can be accomplished by various methods known in the art, such as PCR amplification and restriction cloning, restriction fragmenting of an entire genome and cloning into a vector backbone to produce a library, Transformation-Associated Recombination (TAR) cloning, and other cloning, construction, and synthesis methods. As with the source cell, the heterologous editing cells may be of bacterial, fungal, plant, mammalian, or human origin. The edits of the source target polynucleotide can be virtually any type of edit, including saturation mutagenesis, knockouts, loss of function mutations, gain of function changes, coding variations (including codon changes, and the addition or removal of stop or start codons), as well as changes to regulatory and other noncoding regions. Finally, the ultimate destination of the edited shuttle vector may be back to the source cell, to another, different, vector, or to yet another bacterial, fungal, plant, mammalian, or human cell.

Cloning Strategies for Introducing Exogenous Genetic Material to Shuttle Vectors The means by which target polynucleotides are introduced to a shuttle vector depend on the choice of shuttle vector, source locus of the polynucleotide, size of the insert, and for the embodiments disclosed herein, the desired edits of the target polynucleotide and eventual destination of the edited target polynucleotide. The following paragraphs discuss strategies for cloning target polynucleotides from the source cells, introducing the target polynucleotides to shuttle vectors, as well as some exemplary methods and considerations for the cloning step of shuttling exogenous polynucleotides from the source cells to the heterologous editing cells in which automated editing occurs.

In some implementations, target polynucleotides may be amplified by polymerase chain reaction (PCR) using oligonucleotide primers complementary to sequences flanking the target polynucleotide. PCR primers may be designed in such a way that the resulting amplicons contain restriction sites for recognition by restriction endonucleases. Amplicons may then be digested by restriction endonucleases and ligated into a, e.g., plasmid shuttle vector at the polylinker region by conventional "sticky end" cloning. The resulting shuttle vector may be introduced to heterologous editing cells for automated nucleic acid-guided nuclease editing.

Alternatively, in some implementations, target polynucleotides may be amplified by PCR as described above, but with PCR primers designed such that the resulting amplicons contain homology arms of size 10-500 nucleotides at their 5' and 3' ends. These arms may be homologous to a sequence in the shuttle vector such that after linearizing the shuttle vector by restriction enzyme digestion the arms may mediate in vitro isothermic assembly (see, e.g., U.S. Pat. No. 7,776,532). This method has the advantages of 1) not requiring restriction sites in either the target polynucleotide amplicon or in the shuttle vector backbone, and 2) scarless incorporation of the target polynucleotide insert into the shuttle vector.

In yet other implementations, target polynucleotides may be commercially synthesized. The target polynucleotide may be synthesized in a commercially-available vector and subcloned into the desired shuttle vector by conventional methods, including but not limited to restriction enzyme "sticky end" cloning and in vitro isothermic assembly. Alternatively, the shuttle vector may be commercially synthesized in circular plasmid form already containing the target polynucleotide.

For implementations when the target "polynucleotide" is an entire genome, a genomic library of shuttle vectors may be constructed. Total genomic DNA may be fractionated by restriction enzyme digest, e.g. BamHI or EcoRI, size selected by one of various standard methods, e.g. sucrose gradient or gel electrophoresis, and ligated into a linearized BAC or YAC vector backbone (Burke & Olson, Methods Enzymol. 194(c):251-270 (1991); and Foote & Denny, Curr Protoc Hum Genet. (2002)), yielding a heterogenous mix of shuttle vectors containing target polynucleotide inserts representing the entire source genome. The library of shuttle vectors may then be introduced to heterologous editing cells for automated nucleic acid-guided nuclease editing.

In some implementations a target polynucleotide may already be cloned from a source and exist in a vector or library. In this case the target polynucleotide may be subcloned by restriction enzyme digest, amplified by PCR, or other standard techniques, and introduced to a desired shuttle vector by one of several techniques e.g. restriction enzyme "sticky end" cloning, in vitro isothermal assembly, or in vivo recombination in yeast. The resulting shuttle vector may then be introduced to heterologous editing cells for automated nucleic acid-guided nuclease editing.

In some implementations, when the target polynucleotide is an entire gene or large multi-gene locus, the target polynucleotide may be introduced to the shuttle vector by transformation-associated recombinational (TAR) cloning in yeast. TAR cloning is a useful method for capturing relatively large genomic loci in YACs and allows entire genes and large chromosomal regions to be selectively and accurately isolated from total genomic DNA by in vivo recombination in yeast (Kouprina, et al., Nat Rev Genet., 7:805-812 (2006); Kouprina, et al., Curr Protoc Hum Genet., Chapter 5 Unit 5.17 (2006)). Advantages of TAR cloning include 1) specificity in targeting genomic loci (as opposed to random library generation), 2) accuracy, and 3) the capacity to clone large inserts. TAR cloning vectors may comprise a CEN sequence, yeast selectable marker, yeast telomeric sequences, and at both ends two gene-specific "hooks," which are two regions of homology that flank the source genomic target polynucleotide (see U.S. Pat. No. 6,391,642). These hooks mediate recombination between the TAR cloning vector and target genomic DNA—which are co-transformed into the heterologous editing cells—resulting in a circular YAC containing the genomic target polynucleotide insert. TAR cloning is particularly useful for cloning mammalian target loci, as the method depends on the presence of an ARS-like sequence in the cloned insert for the resulting YAC to replicate faithfully in yeast. ARS-like elements are abundant in mammalian genomes, occurring at a frequency of approximately 20-40 kb. TAR cloning vectors may also have properties of BACs or may be retrofitted after cloning to have properties of BACs and may be shuttled between bacteria and yeast, for example, when a genomic locus is introduced into a YAC by TAR cloning in yeast but propagation and rapid large-scale DNA preparation in bacteria is desired. Such shuttle vectors produced by TAR cloning may be edited in either yeast or bacteria cells.

Nucleic Acid-Guided Cell Editing Generally

Various shuttle vectors comprising the desired target polynucleotides described herein (e.g., gene(s), coding sequences, multi-gene loci, regulatory elements, genomes) are edited by nucleic acid-guided editing methods, modules, instruments and systems in which nucleic acid-guided nucleases (e.g., RNA-guided nucleases) are used to edit specific target regions in the shuttle vector(s). A nucleic acid-guided nuclease complexed with an appropriate synthetic guide nucleic acid in a cell can cut the shuttle vector at a desired location. The guide nucleic acid helps the nucleic acid-guided nuclease recognize and cut a specific target sequence in the shuttle vector. By manipulating the nucleotide sequence of the guide nucleic acid, the nucleic acid-guided nuclease may be programmed to target any DNA sequence for cleavage as long as an appropriate protospacer adjacent motif (PAM) is nearby.

The components for nucleic acid-guided editing may be delivered to heterologous editing cells in various ways and in various combinations. For example, the nuclease itself may be delivered to a cell comprising a shuttle vector as a polypeptide; alternatively, a polynucleotide sequence encoding the nuclease(s) is transformed or transfected into the cells comprising the shuttle vector to be edited. The polynucleotide sequence encoding the nuclease may be codon optimized for expression in particular cells, such as eukaryotic cells, including mammalian cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the nuclease to be employed depends on many factors, such as what type of edit is to be made in the target sequence and whether an appropriate PAM is located close to the desired target sequence. The nuclease may be encoded by a DNA sequence on a vector (e.g., an engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter. In yet another example, the coding sequence for the nuclease may be under the control of an inducible promoter and the transcription sequence for the guide nucleic acid may be under the control of a constitutive promoter.

In general, a guide nucleic acid (e.g., gRNA) complexes with a compatible nucleic acid-guided nuclease and can then hybridize with a target sequence in the shuttle vector, thereby directing the nuclease to the target sequence. In certain aspects, a CRISPR editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and instruments, the guide nucleic acid typically is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence in a shuttle vector by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif (PAM) sequence adjacent to the target sequence. Herein, the target sequence is contained within a shuttle vector that is exogenous to a destination cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a shuttle vector. In yet other embodiments, the sequence encoding the guide nucleic acid and the sequence encoding the donor nucleic acid are both included in the editing cassette. Methods and compositions for designing and synthesizing editing cassettes are described in U.S. Pat. Nos. 10,240,167; 10,266,849; 9,982,278; 10,351,877; 10,364,442; and 10,435,715; and U.S. Ser. No. 16/275,465, filed 14 Feb. 2019, all of which are incorporated by reference herein.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, reduce cutting efficiency, decrease target site recognition fidelity, or increase the versatility of a nucleic acid-guided nuclease. In certain embodiments, the editing of a target sequence both introduces a desired DNA change to a target sequence, e.g., the desired sequences contained on the shuttle vector within a cell, and removes, mutates, or renders inactive a protospacer mutation (PAM) region in the target sequence. Rendering the PAM at the target sequence inactive precludes additional editing of the shuttle vector at that target sequence, e.g., upon subsequent exposure to a nucleic acid-guided nuclease complexed with a synthetic guide nucleic acid in later rounds of editing.

The range of target sequences that nucleic acid-guided nucleases can recognize is constrained by the need for a specific PAM to be located near the desired target sequence. As a result, it often can be difficult to target edits with the precision that is necessary for editing. It has been found that nucleases can recognize some PAMs very well (e.g., canonical PAMs), and other PAMs less well or poorly (e.g., non-canonical PAMs).

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments—such as embodiments where cell selection is employed—the promoter driving transcription of the gRNA and the donor nucleic acid (or driving more than one gRNA/donor nucleic acid pair) is an inducible promoter. Inducible editing is advantageous in that singulated or substantially singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Pat. No. 10,550,363, issued 4 Feb. 2020. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

Also, as described above, the donor nucleic acid may comprise—in addition to the at least one mutation relative to a target sequence—one or more PAM sequence alterations that mutate, delete or render inactive the PAM site in the target sequence. The PAM sequence alteration in the target sequence in the shuttle vector renders the PAM site "immune" to the nucleic acid-guided nuclease and protects the target sequence from further editing in subsequent rounds of editing if the same nuclease is used.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or shuttle vector-wide libraries of donor nucleic acids. The library of editing cassettes are cloned into vector backbones where, e.g., each different donor nucleic acid is associated with a different barcode.

Additionally, in some embodiments, an expression vector or cassette encoding components of the nucleic acid-guided nuclease system further comprises one or more nuclear localization sequences (NLSs), such as about or more than about 1, 2, 3, 4, 5, 6, 7, 8, 9, 10, or more NLSs. In some embodiments, the vectors encoding the editing components comprise NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the nuclease editing system may be inducible, and an inducible system is likely employed if selection is to be performed. A number of gene regulation control systems have been developed for the controlled expression of genes in plant, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12): 5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Performing genome editing in live cells entails transforming cells with the components necessary to perform nucleic acid-guided nuclease editing. For example, the cells may be transformed simultaneously with separate engine and editing vectors; the cells may already be expressing a nuclease (e.g., the cells may have already been transformed with an engine vector or the coding sequence for the nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a heterologous editing cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., USPNs 10,435,713, issued 8 Oct. 2019; U.S. Pat. No. 10,443,074, issued 15 Oct. 2019; U.S. Pat. No. 10,323,258, issued 18 Jun. 2019; U.S. Pat. No. 10,568,288, issued 17 Dec. 2019; and U.S. Pat. No. 10,415,058, issued 17 Sep. 2019.

After the cells are transformed with the components necessary to perform nucleic acid-guided nuclease editing, the cells are cultured under conditions that promote editing. For example, if constitutive promoters are used to drive transcription of the nuclease and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, and nuclease—the cells are subjected to inducing conditions.

Production of Cell Libraries comprising Shuttle Vectors using Automated Editing Methods and Instruments In one aspect, the present disclosure provides automated editing methods and multi-module cell editing instruments for creating a library of cells that vary the expression, levels and/or activity of RNAs and/or proteins of interest in cells using various editing strategies, as described herein in more detail. Accordingly, the disclosure is intended to cover edited cell libraries comprising the shuttle vectors created by the automated editing methods and multi-module cell editing instruments of the disclosure. These cell libraries may have different targeted edits, including but not limited to gene knockouts, gene knock-ins, insertions, deletions, single nucleotide edits, short tandem repeat edits, frameshifts, and triplet codon expansion. These edits can be directed to coding or non-coding regions of the genome and are preferably rationally designed.

In specific aspects, the cell libraries are created using multiplexed editing of individual cells comprising one or more shuttle vectors within a cell population, where multiple cells within a cell population are edited in a single round of editing, i.e., multiple changes within the shuttle vectors of the cells of the cell library are edited in a single automated operation. The libraries that can be created in a single multiplexed automated operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more, and the number of different types of edits that can be created in a single multiplexed automated operation can comprise 500, 1,000, 5,000, 10,000, 20,000, 25,000, 30,000, 40,000, 50,000, 60,000, 70,000, 80,000, 90,000 or up to 100,000 edits or more.

In other specific aspects, the cell libraries are created using recursive editing of shuttle vectors of individual cells within a cell population, with edits being added to the individual cells in two or more rounds of editing. The use of recursive editing results in the amalgamation of two or more edits targeting two or more sites in a shuttle vector in individual cells of the library. The libraries that can be created in an automated recursive operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more, and the number of different types of edits that can be created in recursive multiplexed automated operations can comprise 500, 1,000, 5,000, 10,000, 20,000, 25,000, 30,000, 40,000, 50,000, 60,000, 70,000, 80,000, 90,000 or up to 100,000 edits or more per round of editing.

In specific aspects, recursive editing can be used to first create a cell phenotype, and then later rounds of editing used to reverse the phenotype and/or accelerate other cell properties.

In some aspects, the cell library comprises edits for the creation of unnatural amino acids in a cell.

In specific aspects, there are provided cell libraries having edits in one or more regulatory elements in the shuttle vectors created using the automated editing methods and multi-module cell editing instruments of the disclosure. The term "regulatory element" refers to nucleic acid molecules that can influence the transcription and/or translation of an operably linked coding sequence in a particular environment and/or context. This term is intended to include all elements that promote or regulate transcription, and RNA stability including promoters, core elements required for basic interaction of RNA polymerase and transcription factors, upstream elements, enhancers, transcription factor binding sites, and response elements. Exemplary regulatory elements used in eukaryotic cells may include, but are not limited to, promoters, enhancers, insulators, splicing signals and polyadenylation signals.

Preferably, the edited cell library includes rationally-designed edits that are designed based on predictions of protein structure, expression and/or activity in a particular cell type. For example, rational design may be based on a system-wide biophysical model of genome editing with a particular nuclease and gene regulation to predict how different editing parameters including nuclease expression and/or binding, growth conditions, and other experimental conditions collectively control the dynamics of nuclease editing. See, e.g., Farasat and Salis, PLoS Comput Biol., 29:12(1):e1004724 (2016).

In one aspect, there is provided creation of a library of edited cells with various rationally-designed regulatory sequences created using automated editing modules, instrumentation, systems and methods. In one example, the edited cell library includes eukaryotic sequences created using a set of constitutive and/or inducible promoters, enhancer sequences, operator sequences, and/or different Kozak sequences for expression of proteins of interest.

In some aspects, there are provided cell libraries including cells with rationally-designed edits comprising one or more classes of edits in sequences of interest across the shuttle vectors.

Importantly, in certain aspects the cell libraries may comprise edits using randomized sequences, e.g., randomized promoter sequences, to reduce similarity between expression of one or more proteins in individual cells within the library. Additionally, the promoters in the cell library can be constitutive, inducible or both to enable strong and/or titratable expression.

In other aspects, the present disclosure provides automated editing methods and multi-module cell editing instruments for creating a library of cells comprising edits to identify optimum expression of a selected gene target. For example, production of biochemicals through metabolic engineering often requires the expression of pathway enzymes, and the best production yields are not always achieved by the highest amount of the target pathway enzymes in the cell, but rather by fine-tuning of the expression levels of the individual enzymes and related regulatory proteins and/or pathways. Similarly, expression levels of heterologous proteins sometimes can be experimentally adjusted for optimal yields.

One way that transcription impacts gene expression levels is through the rate of Pol II initiation, which can be modulated by combinations of promoter or enhancer strength and trans-activating factors (see, e.g., Kadonaga, et al., Cell, 116(2):247-57 (2004)). In eukaryotes, elongation rate may also determine gene expression patterns by influencing alternative splicing (Cramer, et al., PNAS USA, 94(21): 11456-60 (1997)). Failed termination on a gene can impair the expression of downstream genes by reducing the accessibility of the promoter to Pol II (Greger, et al., PNAS USA, 97(15):8415-20 (2000)). This process, known as transcriptional interference, is particularly relevant in lower eukaryotes, as they often have closely spaced genes.

In some embodiments there are provided methods for optimizing cellular gene transcription. Gene transcription is the result of several distinct biological phenomena, including transcriptional initiation (RNAp recruitment and transcriptional complex formation), elongation (strand synthesis/extension), and transcriptional termination (RNAp detachment and termination).

Site Directed Mutagenesis

Cell libraries can be created via site-directed mutagenesis using the automated editing methods, modules, instruments, and systems, i.e., when the amino acid sequence of a protein or other genomic feature preferably is to be altered by deliberately and precisely by mutating the protein or genomic feature. These cell libraries can be useful for various purposes, e.g., for determining protein function within cells, for identifying of enzymatic active sites within cells, and for designing novel proteins. For example, site-directed mutagenesis can be used in a multiplexed fashion to exchange a single amino acid in the sequence of a protein for another amino acid with different chemical properties. This allows one to determine the effect of a rationally-designed or randomly-generated mutation in individual cells within a cell population. See, e.g., Berg, et al. Biochemistry, Sixth Ed. (New York: W.H. Freeman and Company) (2007).

In another example, edits can be made to individual cells within a cell library to substitute amino acids in binding sites, such as substitution of one or more amino acids in a protein binding site for interaction within a protein complex or substitution of one or more amino acids in enzymatic pockets that can accommodate a cofactor or ligand. This class of edits allows the creation of specific manipulations to measure certain properties of one or more proteins, including interaction with other cofactors, ligands, etc. within a protein complex.

In yet another examples, various edit types can be made to individual cells within a cell library using site specific mutagenesis for studying expression quantitative trait loci (eQTLs). An eQTL is a locus that explains a fraction of the genetic variance of a gene expression phenotype. The libraries are useful to evaluate and link eQTLs to actual diseased states.

In specific aspects, the edits introduced into the shuttle vectors to create the cell libraries may be created using rational design based on known or predicted structures of proteins. See, e.g., Chronopoulou and Labrou, Curr Protoc Protein Sci.; Chapter 26:Unit 26.6 (2011). Such site-directed mutagenesis can provide individual cells within a library with one or more site-directed edits, and preferably two or more site-directed edits (e.g., combinatorial edits) within a cell population.

In other aspects, cell libraries of the disclosure are created using site-directed codon mutation "scanning" of all or substantially all of the codons in the coding region of a gene. In this fashion, individual edits of specific codons can be examined for loss-of-function or gain-of-function based on specific polymorphisms in one or more codons of the gene. These libraries can be a powerful tool for determining which genetic changes are silent or causal of a specific phenotype in a cell or cell population. The edits of the codons may be randomly-generated or may be rationally-designed based on known polymorphisms and/or mutations that have been identified in the gene to be analyzed. Moreover, using these techniques on two or more genes in a single in a pathway in a cell may determine potential protein:protein interactions or redundancies in cell functions or pathways.

For example, alanine scanning can be used to determine the contribution of a specific residue to the stability or function of given protein. See, e.g., Lefèvre, et al., Nucleic Acids Research, 25(2):447-448 (1997). Alanine is often used in this codon scanning technique because of its non-bulky, chemically inert, methyl functional group that can mimic the secondary structure preferences that many of the other amino acids possess. Codon scanning can also be used to determine whether the side chain of a specific residue plays a significant role in cell function and/or activity. Sometimes other amino acids such as valine or leucine can be used in the creation of codon scanning cell libraries if conservation of the size of mutated residues is needed.

In other specific aspects, cell libraries can be created using the automated editing methods and multi-module cell editing instruments to determine the active site of a protein such as an enzyme or hormone, and to elucidate the mechanism of action of one or more of these proteins in a cell library. Site-directed mutagenesis associated with molecular modeling studies can be used to discover the active site structure of an enzyme and consequently its mechanism of action. Analysis of these cell libraries can provide an understanding of the role exerted by specific amino acid residues at the active sites of proteins, in the contacts between subunits of protein complexes on intracellular trafficking and protein stability/half-life in various genetic backgrounds.

Saturation Mutagenesis

In some aspects, the cell libraries created using the automated editing methods and multi-module cell editing instruments of the disclosure may be saturation mutagenesis libraries, in which a single codon or set of codons is randomized to produce all possible amino acids at the position of a particular gene or genes of interest. These cell libraries can be particularly useful to generate variants, e.g., for directed evolution. See, e.g., Chica, et al., Current Opinion in Biotechnology, 16(4): 378-384 (2005); and Shivange, Current Opinion in Chemical Biology, 13(1): 19-25 (2009).

In some aspects, edits comprising different degenerate codons can be used to encode sets of amino acids in the individual cells in the libraries. Because some amino acids are encoded by more codons than others, the exact ratio of amino acids cannot be equal. In certain aspects, more restricted degenerate codons are used. 'NNK' and 'NNS' have the benefit of encoding all 20 amino acids, but still encode a stop codon 3% of the time. Alternative codons such as 'NDT', 'DBK' avoid stop codons entirely, and encode a minimal set of amino acids that still encompass all the main biophysical types (anionic, cationic, aliphatic hydrophobic, aromatic hydrophobic, hydrophilic, small).

Promoter Swaps and Ladders

One mechanism for analyzing and/or optimizing expression of one or more genes of interest is through the creation of a "promoter swap" cell library, in which the cells comprise genetic edits that have specific promoters linked to one or more genes of interest. Accordingly, cell libraries created using the automated methods and multi-module cell editing instruments may be promoter swap cell libraries, which is used, e.g., to increase or decrease expression of a gene of interest to optimize a metabolic or genetic pathway. In some aspects, the promoter swap cell library is used to identify an increase or reduction in the expression of a gene that affects cell vitality or viability, e.g., a gene encoding a protein that impacts on the growth rate or overall health of the cells. In some aspects, the promoter swap cell library can be used to create cells having dependencies and logic between the promoters to create synthetic gene networks. In some aspects, the promoter swaps can be used to control cell to cell communication between cells of both homogeneous and heterogeneous (complex tissues) populations in nature.

The cell libraries may utilize any given number of promoters that have been grouped together based upon exhibition of a range of expression strengths and any given number of target genes. The ladder of promoter sequences vary expression of at least one locus under at least one condition. This ladder is then systematically applied to a group of genes on the shuttle vector using the automated editing methods and multi-module cell editing instruments of the disclosure.

In specific aspects, the cell library formed using the automated editing processes, modules and multi-module instruments of the disclosure include individual cells that are representative of a given promoter operably linked to one or more target genes of interest in an otherwise identical genetic background.

In specific aspects, the promoter swap cell library is produced by editing a set of target genes on a shuttle vector to be operably linked to a pre-selected set of promoters that act as a "promoter ladder" for expression of the genes of interest. For example, the shuttle vectors are edited so that one or more individual genes of interest are edited to be operably linked with the different promoters in the promoter ladder. When an endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in a shuttle vector in an otherwise identical genetic context. The promoters are generally selected to result in variable expression across different loci, and may include inducible promoters, constitutive promoters, or both.

The set of target genes edited using the promoter ladder can include all or most open reading frames (ORFs) in a shuttle vector, or a selected subset of the shuttle vector. In some aspects, the target genes can include coding regions for various isoforms of the genes, and the cell libraries can be designed to express one or more specific isoforms, e.g., for transcriptome analysis using various promoters.

The set of target genes can also be genes known or suspected to be involved in a particular cellular pathway, e.g. a regulatory pathway or signaling pathway. The set of target genes can be ORFs related to function, by relation to previously-demonstrated beneficial edits (previous promoter swaps or previous SNP swaps), by algorithmic selection based on epistatic interactions between previously generated edits, other selection criteria based on hypotheses regarding beneficial ORF to target. In specific embodiments, the target genes can comprise non-protein coding genes, including non-coding RNAs.

Editing of other functional genetic elements, including insulator elements and other genomic organization elements, can also be used to systematically vary the expression level of a set of target genes, and can be introduced using the automated methods and automated multi-module cell editing instruments of the disclosure. In one aspect, a population of cells comprising shuttle vectors is edited using a ladder of enhancer sequences, either alone or in combination with selected promoters or a promoter ladder, to create a cell library having various edits in these enhancer elements. In another aspect, a population of cells is edited using a ladder of ribosome binding sequences, either alone or in combination with selected promoters or a promoter ladder, to create a cell library having various edits in these ribosome binding sequences.

In another aspect, a population of cells is edited to allow the attachment of various mRNA and/or protein stabilizing or destabilizing sequences to the 5' or 3' end, or at any other location, of a transcript or protein.

When recursive editing is used, the editing in the individual cells in the edited cell library can incorporate the inclusion of "landing pads" in an ectopic site in the shuttle vector to optimize expression, stability and/or control.

In some embodiments, each library produced having shuttle vectors comprising one or more edits (either introducing or removing) is cultured and analyzed under one or more criteria (e.g., production of a chemical or product of interest). The cells possessing the specific criteria are then associated, or correlated, with one or more particular edits in the cell. In this manner, the effect of a given edit on any number of genetic or phenotypic traits of interest can be determined. The identification of multiple edits associated with particular criteria or enhanced functionality/robustness may lead to cells with highly desirable characteristics.

Knock-Out or Knock-in Libraries

In certain aspects, the present disclosure provides automated editing methods, and automated modules, instruments and systems for creating a library of cells comprising shuttle vectors having "knock-out" (KO) or "knock-in" (KI) edits of various genes of interest. Thus, the disclosure is intended to cover edited cell libraries created by the automated editing methods and automated multi-module cell editing instruments of the disclosure that have one or more mutations that remove or reduce the expression of selected genes of interest to interrogate the effect of these edits on gene function in individual cells within the cell library.

The cell libraries comprising the shuttle vectors can be created using targeted gene KO (e.g., via insertion/deletion) or KOs (e.g., via homologous directed repair). For example, double strand breaks are often repaired via the non-homologous end joining DNA repair pathway. The repair is known to be error prone, and thus insertions and deletions may be introduced that can disrupt gene function. Preferably the edits are rationally designed to specifically affect the genes of interest, and individual cells can be created having a KI or KI of one or more locus of interest. Cells having a KO or KI of two or more loci of interest can be created using automated recursive editing of the disclosure.

In specific aspects, the KO or KI cell libraries are created using simultaneous multiplexed editing of shuttle vectors within a cell population, and multiple shuttle vectors within a cell population are edited in a single round of editing, i.e., multiple changes within the shuttle vectors of the cells of the cell library are in a single automated operation. In other specific aspects, the cell libraries are created using recursive editing of shuttle vectors within a cell population, and results in the amalgamation of multiple edits of two or more sites in the shuttle vectors into single cells.

SNP or Short Tandem Repeat Swaps

In one aspect, cell libraries are created using the automated editing methods and automated multi-module cell editing instruments of the disclosure by systematically introducing or substituting single nucleotide polymorphisms ("SNPs") into the shuttle vectors of the individual cells to create a "SNP swap" cell library. In some embodiments, the SNP swapping methods include both the addition of beneficial SNPs and removing detrimental and/or neutral SNPs. The SNP swaps may target coding sequences, non-coding sequences, or both.

In another aspect, a cell library is created using the automated editing methods and modules, instruments, and systems by systematically introducing or substituting short tandem repeats ("STR") into the shuttle vectors of the individual cells to create an "STR swap" cell library. In some embodiments, the STR swapping methods of the present disclosure include both the addition of beneficial STRs and removing detrimental and/or neutral STRs. The STR swaps may target coding sequences, non-coding sequences, or both.

In some embodiments, the SNP and/or STR swapping used to create the cell library is multiplexed, and multiple shuttle vectors in the cells within a cell population are edited in a single round of editing, i.e., multiple changes within the shuttle vectors in the cells of the cell library are introduced in a single automated operation. In other embodiments, the SNP and/or STR swapping used to create the cell library is recursive, and results in the amalgamation of multiple beneficial sequences and/or the removal of detrimental sequences into the shuttle vectors. Multiple changes can be either a specific set of defined changes or a partly-randomized, combinatorial library of mutations. Removal of detrimental mutations and consolidation of beneficial mutations can provide immediate improvements in various cellular processes. Removal of genetic burden or consolidation of beneficial changes into a cell with no genetic burden also provides a new, robust starting point for additional random mutagenesis that may enable further improvements.

SNP swapping overcomes fundamental limitations of random mutagenesis approaches as it is not a random approach, but rather the systematic introduction or removal of individual mutations across cells.

Splice Site Editing

RNA splicing is the process during which introns are excised and exons are spliced together to create the mRNA that is translated into a protein. The precise recognition of splicing signals by cellular machinery is critical to this process. Accordingly, in some aspects, a population of cells comprising one or more shuttle vectors is edited using systematic editing of known and/or predicted splice donor and/or acceptor sites in various loci to create a library of splice site variants of various genes. Such editing can help to elucidate the biological relevance of various isoforms of genes in a cellular context. Sequences for rational design of splicing sites of various coding regions, including actual or predicted mutations associated with various mammalian disorders, can be predicted using analysis techniques such as those found in Nalla and Rogan, Hum. Mutat., 25:334-342 (2005); Divina, et al., Eur. J. Hum. Genet., 17:759-765 (2009); Desmet, et el., Nucleic Acids Res, 37:e67 (2009); Faber, et al., BMC Bioinformatics, 12(suppl 4):S2 (2011).

Start/Stop Codon Exchanges and Incorporation of Nucleic Acid Analogs

In some aspects, there is provided creation of cell libraries comprising shuttle vectors using the automated editing methods and modules, instruments and systems of the disclosure, where the libraries are created by swapping start and stop codon variants. For example, typical start codons used by eukaryotes are ATG (AUG) most frequently, followed by GTG (GUG) and TTG (UUG). The cell library may include individual cells having substitutions for the native start codons for one or more genes of interest expressed from the shuttle vector. In some aspects, there is provided automated creation of a cell library by replacing ATG start codons with TTG in front of selected genes of interest. In other aspects, there is provided automated creation of a cell library by replacing ATG start codons with GTG. In other aspects, there is provided automated creation of a cell library by replacing GTG start codons with ATG. In other aspects, there is provided automated creation of a cell library by replacing GTG start codons with TTG. In other aspects, there is provided automated creation of a cell library by replacing TTG start codons with ATG. In other aspects, there is provided automated creation of a cell library by replacing TTG start codons with GTG.

In other examples, typical stop codons for S. cerevisiae and mammals are TAA (UAA) and TGA (UGA), respectively. The typical stop codon for monocotyledonous plants is TGA (UGA), whereas insects commonly use TAA (UAA) as the stop codon (Dalphin, et al., Nucl. Acids Res., 24: 216-218 (1996)). The cell library may include individual cells having substitutions for the native stop codons for one or more genes of interest. In some aspects, there is provided automated creation of a cell library by replacing TAA stop codons with TAG. In other aspects, there is provided a cell library by replacing TAA stop codons with TGA. In other aspects, there is provided a cell library by replacing TGA stop codons with TAA. In other aspects, there is provided a cell library by replacing TGA stop codons with TAG. In other aspects, there is provided a cell library by replacing TAG stop codons with TAA. In other aspects, there is provided automated creation of a cell library by replacing TAG stop codons with TGA.

Terminator Swaps and Ladders

One mechanism for identifying optimum termination of a pre-spliced mRNA of one or more genes of interest is through the creation of a "terminator swap" cell library, in which the cells comprise shuttle vectors that comprise genetic edits that have specific terminator sequences linked to one or more genes of interest. Accordingly, the cell libraries created using the automated methods, modules, instruments and systems of the disclosure may be terminator swap cell libraries, which can be used, e.g., to affect mRNA stability by releasing transcripts from sites of synthesis. In other embodiments, the terminator swap cell library can be used to identify an increase or reduction in the efficiency of transcriptional termination and thus accumulation of unspliced pre-mRNA (e.g., West and Proudfoot, Mol Cell., 33(3-9); 354-364 (2009)) and/or 3' end processing (e.g., West, et al., Mol Cell. 29(5):600-10 (2008)). In the case where a gene is linked to multiple termination sites, the edits may edit a combination of edits to multiple terminators that are associated with a gene. Additional amino acids may also be added to the ends of proteins to determine the effect on the protein length on terminators.

The cell libraries comprising shuttle vectors utilize any given number of edits of terminators that have been selected for the terminator ladder based upon exhibition of a range of activity and any given number of target genes. The ladder of terminator sequences vary expression of at least one locus under at least one condition. This ladder is then systematically applied to a group of genes in the organism using the automated editing methods, modules, instruments and systems of the disclosure.

In some aspects, there is provided creation of cell libraries using the automated editing methods, modules, instruments and systems of disclosure, where the libraries are created to edit terminator signals in one or more regions in the shuttle vector(s) in the individual cells of the library. Transcriptional termination in eukaryotes operates through terminator signals that are recognized by protein factors associated with the RNA polymerase II. For example, the cell library may contain individual eukaryotic cells with edits in genes encoding polyadenylation specificity factor (CPSF) and cleavage stimulation factor (CstF) and/or genes encoding proteins recruited by CPSF and CstF factors to termination sites.

In certain aspects, the present disclosure provides methods of selecting termination sequences ("terminators") with optimal properties. For example, in some embodiments, provided are methods for introducing and/or editing one or more terminators and/or generating variants of one or more terminators within a heterologous editing cell, which exhibit a range of activity.

In specific aspects, the terminator swap cell library is produced by editing a set of target genes in a shuttle vector to be operably linked to a pre-selected set of terminators that act as a "terminator ladder" for expression of the genes of interest. For example, the cells are edited so that the endogenous promoter is operably linked to the individual genes of interest, which are then edited with the different promoters in the promoter ladder. When the endogenous promoter does not exist, its sequence is unknown, or it has been previously changed in some manner, the individual promoters of the promoter ladder can be inserted in front of the genes of interest. These cell libraries have individual cells with one or more shuttle vectors comprising with an individual promoter of the ladder operably linked to one or more target genes in an otherwise identical genetic context. The terminator ladder in question is then associated with a given gene of interest. The terminator ladder can be used to more generally affect termination of all or most ORFs in a shuttle vector, or a selected subset of the shuttle vector. The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

Figure 2A:
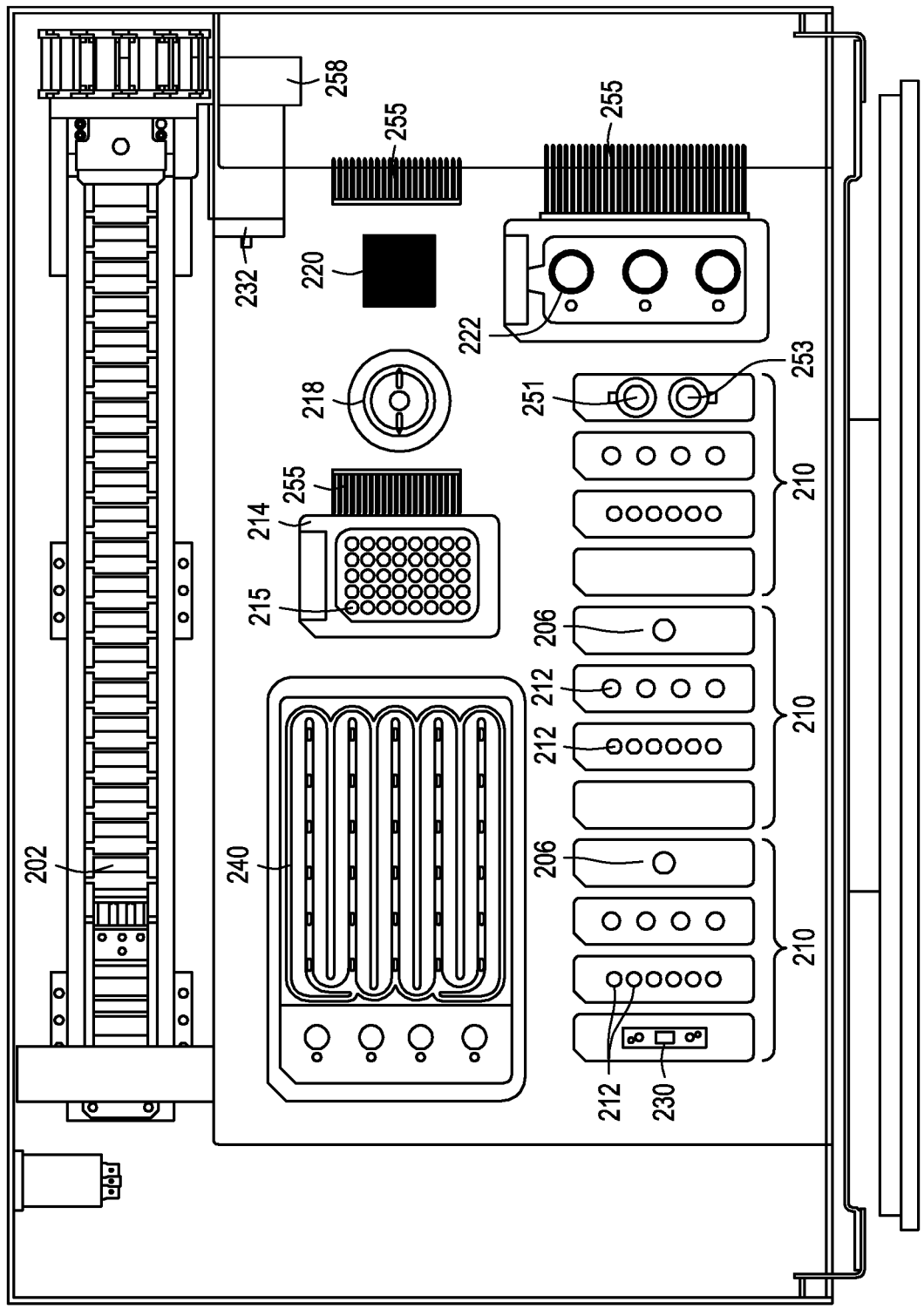
FIGS. 2A-2C depict three different views of an exemplary automated multi-module cell processing instrument for performing nucleic acid-guided nuclease editing.

Automated Cell Editing Instruments and Modules to Perform Nucleic Acid-Guided Nuclease Editing in Cells Automated Cell Editing Instruments FIG. 2A depicts an exemplary automated multi-module cell processing instrument 200 to, e.g., perform one of the exemplary workflows for targeted gene editing of live cells. The instrument 200, for example, may be and preferably is designed as a stand-alone desktop instrument for use within a laboratory environment. The instrument 200 may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic) liquid handling system 258 including, e.g., an air displacement pipettor 232 which allows for cell processing among multiple modules without human intervention. In some automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved. Also included in the automated multi-module cell processing instrument 200 are reagent cartridges 210 comprising reservoirs 212 and transformation module 230 (e.g., a flow-through electroporation device as described in detail in relation to FIGS. 5B-5F), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge 210 and wash cartridge 204 may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. In some examples, the robotic handling system 258 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips may be provided in a pipette transfer tip supply (not shown) for use with the air displacement pipettor 232.

Inserts or components of the reagent cartridges 210, in some implementations, are marked with machine-readable indicia (not shown), such as bar codes, for recognition by the robotic handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises a cell growth vial 218 (described in greater detail below in relation to FIGS. 3A-3D). Additionally seen is the TFF module 222 (described above in detail in relation to FIGS. 4A-4E). Also illustrated as part of the automated multi-module cell processing instrument 200 of FIG. 2A is a singulation module 240 (e.g., a solid wall isolation, incubation and normalization device (SWIIN device) is shown here) described herein in relation to FIGS. 6C-6F, served by, e.g., robotic liquid handling system 258 and air displacement pipettor 232. Additionally seen is a selection module 220. Also note the placement of three heatsinks 255.

Figure 2B:
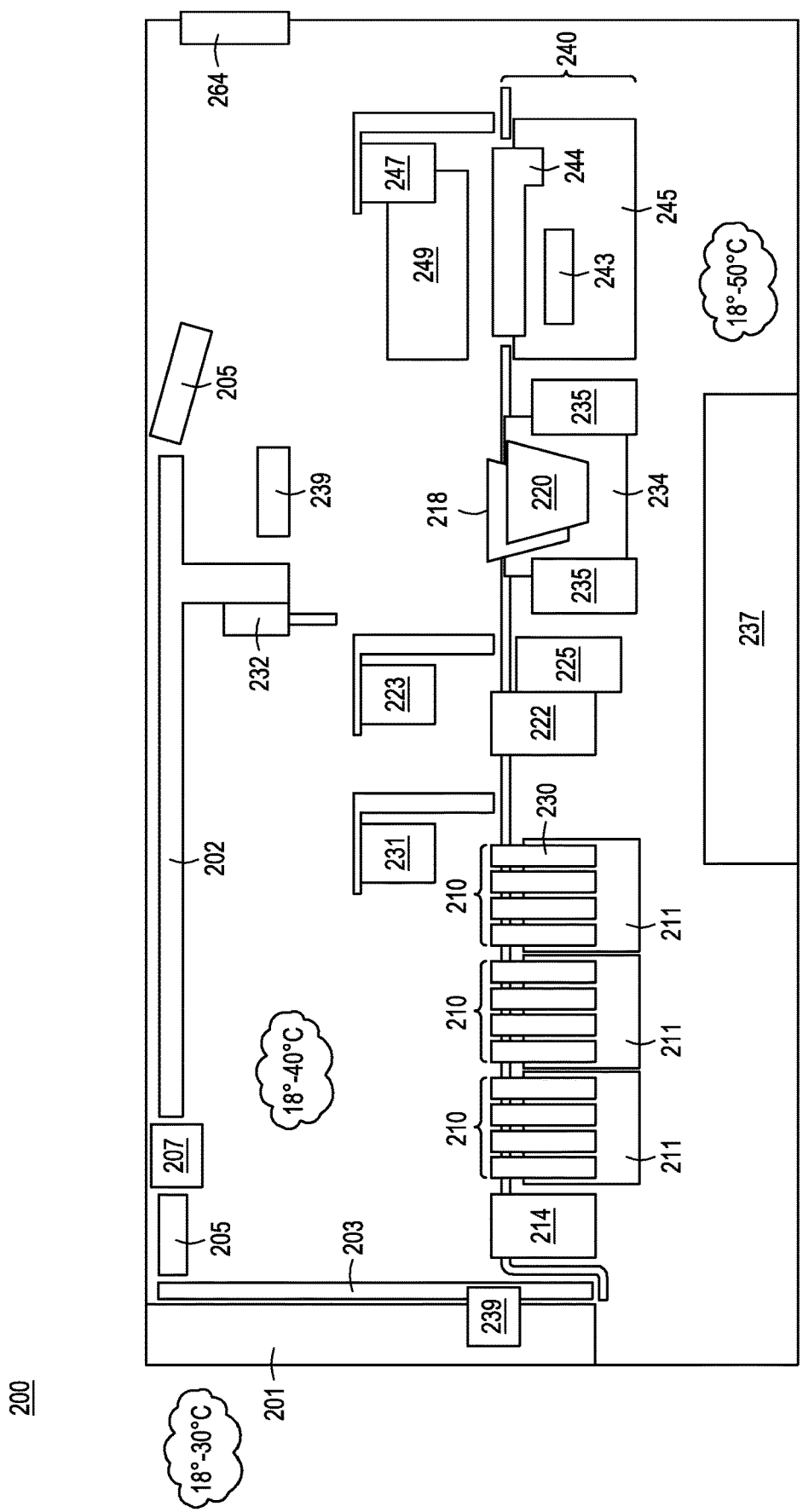

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232. The deck of the multi-module cell processing instrument 200 may include a protection sink such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different regions. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 233. Thermal assemblies 225, 235, and 245 encompass thermal electric devices such as Peltier devices, as well as heatsinks, fans and coolers. The rotating growth vial 218 is within a growth module 234, where the growth module is served by two thermal assemblies 235. Selection module is seen at 220. Also seen is the SWIIN module 240, comprising a SWIIN cartridge 241, where the SWIIN module also comprises a thermal assembly 245, illumination 243 (in this embodiment, backlighting), evaporation and condensation control 249, and where the SWIIN module is served by SWIIN interface (e.g., manifold arm) and actuator 247. Also seen in this view is touch screen display 201, display actuator 203, illumination 205 (one on either side of multi-module cell processing instrument 200), and cameras 239 (one illumination device on either side of multi-module cell processing instrument 200). Finally, element 237 comprises electronics, such as circuit control boards, high-voltage amplifiers, power supplies, and power entry; as well as pneumatics, such as pumps, valves and sensors.

Figure 2C:
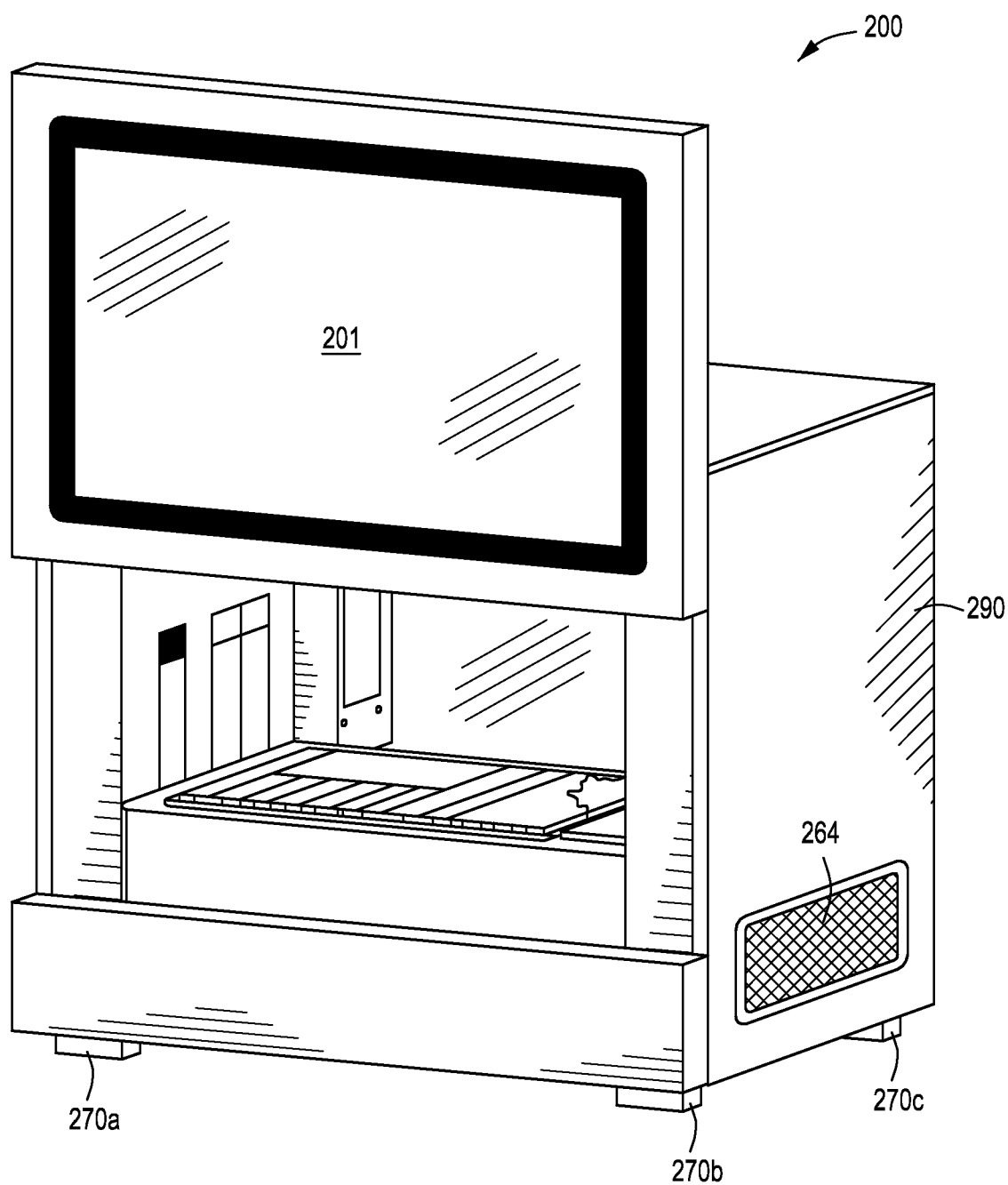

FIG. 2C illustrates a front perspective view of multi-module cell processing instrument 200 for use in as a desktop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270a, 270b, 270c and 270d (feet 270a-270c are shown in this FIG. 2C). Adjustable feet 270a-270d, for example, allow for additional air flow beneath the chassis 290.

Inside the chassis 290, in some implementations, will be most or all of the components described in relation to FIGS. 2A and 2B, including the robotic liquid handling system disposed along a gantry, reagent cartridges 210 including a flow-through electroporation device, a rotating growth vial 218 in a cell growth module 234, a tangential flow filtration module 222, a SWIIN module 240 as well as interfaces and actuators for the various modules. In addition, chassis 290 houses control circuitry, liquid handling tubes, air pump controls, valves, sensors, thermal assemblies (e.g., heating and cooling units) and other control mechanisms. For examples of multi-module cell editing instruments, see U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; U.S. Pat. No. 10,519,437, issued 31 Dec. 2019 and U.S. Ser. No. 16/412,195, filed 14 May 2019; Ser. No. 16/680,643, filed 12 Nov. 2019; and Ser. No. 16/750,369, filed 23 Jan. 2020, all of which are herein incorporated by reference in their entirety.

The Rotating Cell Growth Module

Figure 3A:
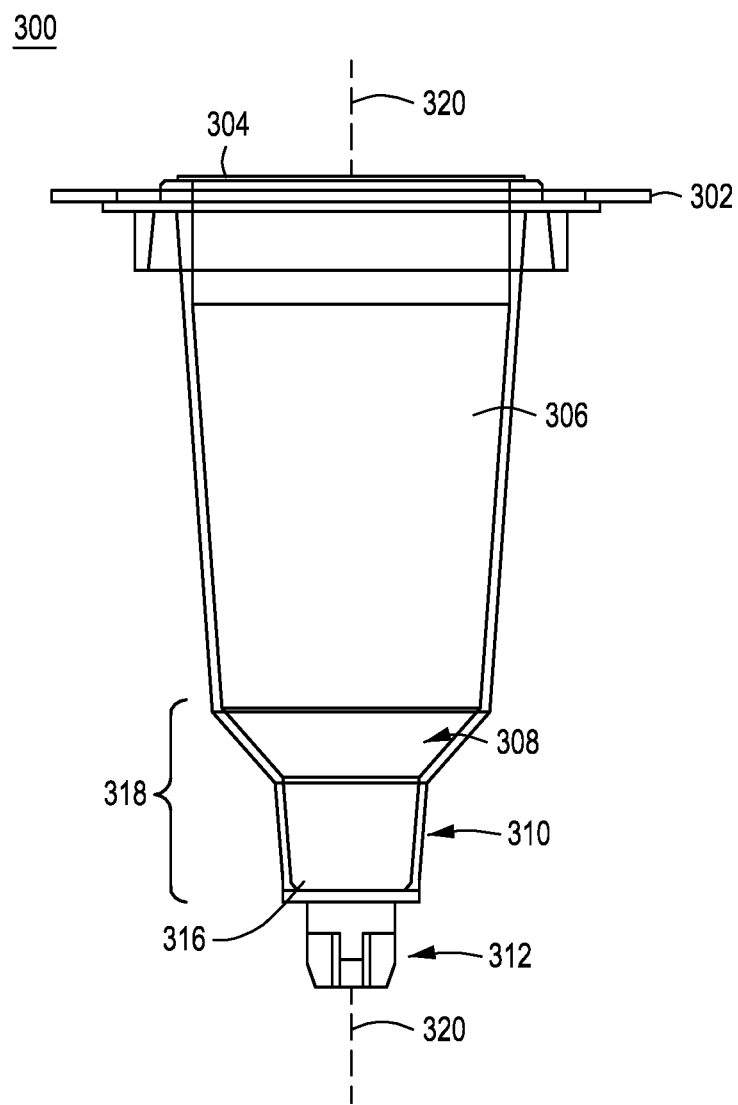
FIG. 3A depicts one embodiment of a rotating growth vial for use with the cell growth module described herein and in relation to FIGS. 3B-3D.

FIG. 3A shows one embodiment of a rotating growth vial 300 for use with the cell growth device and in the automated multi-module cell processing instruments described herein. The rotating growth vial 300 is an optically-transparent container having an open end 304 for receiving liquid media and cells, a central vial region 306 that defines the primary container for growing cells, a tapered-to-constricted region 318 defining at least one light path 310, a closed end 316, and a drive engagement mechanism 312. The rotating growth vial 300 has a central longitudinal axis 320 around which the vial rotates, and the light path 310 is generally perpendicular to the longitudinal axis of the vial. The first light path 310 is positioned in the lower constricted portion of the tapered-to-constricted region 318. Optionally, some embodiments of the rotating growth vial 300 have a second light path 308 in the tapered region of the tapered-to-constricted region 318. Both light paths in this embodiment are positioned in a region of the rotating growth vial that is constantly filled with the cell culture (cells+growth media) and are not affected by the rotational speed of the growth vial. The first light path 310 is shorter than the second light path 308 allowing for sensitive measurement of OD values when the OD values of the cell culture in the vial are at a high level (e.g., later in the cell growth process), whereas the second light path 308 allows for sensitive measurement of OD values when the OD values of the cell culture in the vial are at a lower level (e.g., earlier in the cell growth process).

The drive engagement mechanism 312 engages with a motor (not shown) to rotate the vial. In some embodiments, the motor drives the drive engagement mechanism 312 such that the rotating growth vial 300 is rotated in one direction only, and in other embodiments, the rotating growth vial 300 is rotated in a first direction for a first amount of time or periodicity, rotated in a second direction (i.e., the opposite direction) for a second amount of time or periodicity, and this process may be repeated so that the rotating growth vial 300 (and the cell culture contents) are subjected to an oscillating motion. Further, the choice of whether the culture is subjected to oscillation and the periodicity therefor may be selected by the user. The first amount of time and the second amount of time may be the same or may be different. The amount of time may be 1, 2, 3, 4, 5, or more seconds, or may be 1, 2, 3, 4 or more minutes. In another embodiment, in an early stage of cell growth the rotating growth vial 400 may be oscillated at a first periodicity (e.g., every 60 seconds), and then a later stage of cell growth the rotating growth vial 300 may be oscillated at a second periodicity (e.g., every one second) different from the first periodicity.

The rotating growth vial 300 may be reusable or, preferably, the rotating growth vial is consumable. In some embodiments, the rotating growth vial is consumable and is presented to the user pre-filled with growth medium, where the vial is hermetically sealed at the open end 304 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial. Open end 304 may optionally include an extended lip 402 to overlap and engage with the cell growth device. In automated systems, the rotating growth vial 400 may be tagged with a barcode or other identifying means that can be read by a scanner or camera (not shown) that is part of the automated system.

The volume of the rotating growth vial 300 and the volume of the cell culture (including growth medium) may vary greatly, but the volume of the rotating growth vial 300 must be large enough to generate a specified total number of cells. In practice, the volume of the rotating growth vial 300 may range from 1-250 mL, 2-100 mL, from 5-80 mL, 10-50 mL, or from 12-35 mL. Likewise, the volume of the cell culture (cells+growth media) should be appropriate to allow proper aeration and mixing in the rotating growth vial 300. Proper aeration promotes uniform cellular respiration within the growth media. Thus, the volume of the cell culture should be approximately 5-85% of the volume of the growth vial or from 20-60% of the volume of the growth vial. For example, for a 30 mL growth vial, the volume of the cell culture would be from about 1.5 mL to about 26 mL, or from 6 mL to about 18 mL.

The rotating growth vial 300 preferably is fabricated from a bio-compatible optically transparent material—or at least the portion of the vial comprising the light path(s) is transparent. Additionally, material from which the rotating growth vial is fabricated should be able to be cooled to about 4° C. or lower and heated to about 55° C. or higher to accommodate both temperature-based cell assays and long-term storage at low temperatures. Further, the material that is used to fabricate the vial must be able to withstand temperatures up to 55° C. without deformation while spinning. Suitable materials include cyclic olefin copolymer (COC), glass, polyvinyl chloride, polyethylene, polyamide, polypropylene, polycarbonate, poly(methyl methacrylate (PMMA), polysulfone, polyurethane, and co-polymers of these and other polymers. Preferred materials include polypropylene, polycarbonate, or polystyrene. In some embodiments, the rotating growth vial is inexpensively fabricated by, e.g., injection molding or extrusion.

Figure 3B:
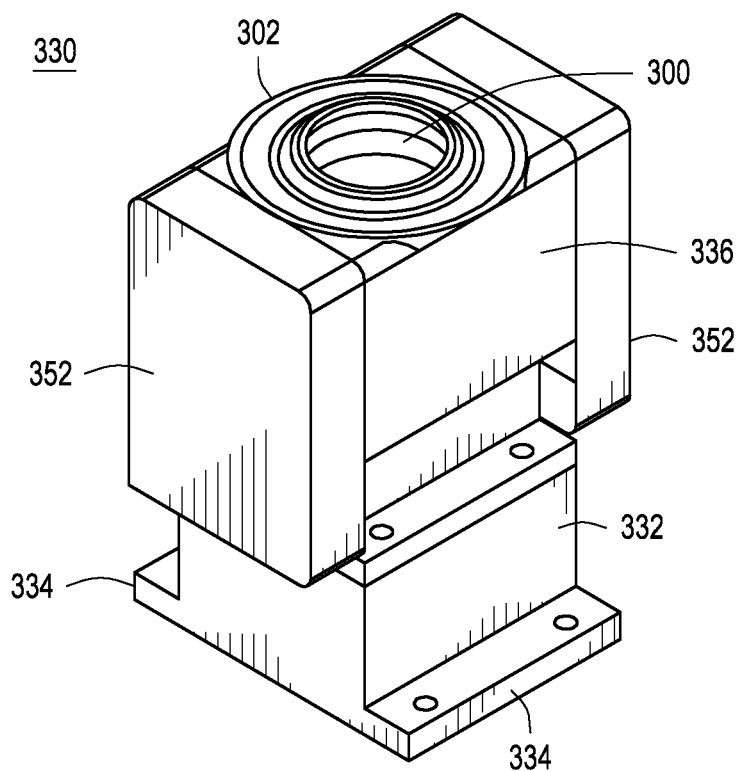
FIG. 3B illustrates a perspective view of one embodiment of a rotating growth vial in a cell growth module housing.
Figure 3C:
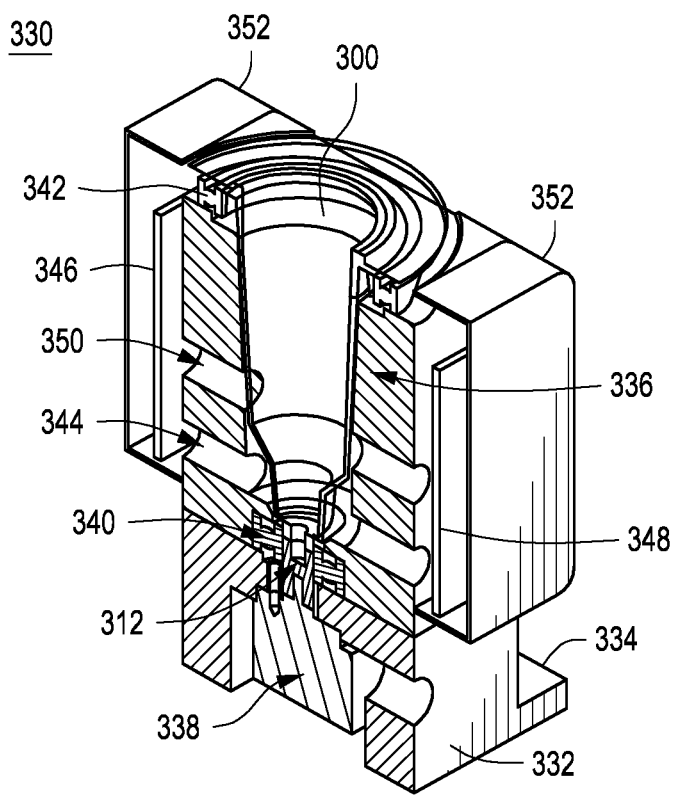
FIG. 3C depicts a cut-away view of the cell growth module from FIG. 3B.

FIG. 3B is a perspective view of one embodiment of a cell growth device 330. FIG. 3C depicts a cut-away view of the cell growth device 330 from FIG. 3B. In both figures, the rotating growth vial 300 is seen positioned inside a main housing 336 with the extended lip 302 of the rotating growth vial 300 extending above the main housing 336. Additionally, end housings 352, a lower housing 332 and flanges 334 are indicated in both figures. Flanges 334 are used to attach the cell growth device 330 to heating/cooling means or other structure (not shown). FIG. 3C depicts additional detail. In FIG. 3C, upper bearing 342 and lower bearing 340 are shown positioned within main housing 336. Upper bearing 342 and lower bearing 340 support the vertical load of rotating growth vial 300. Lower housing 332 contains the drive motor 338. The cell growth device 330 of FIG. 3C comprises two light paths: a primary light path 344, and a secondary light path 350. Light path 344 corresponds to light path 310 positioned in the constricted portion of the tapered-to-constricted portion of the rotating growth vial 300, and light path 350 corresponds to light path 308 in the tapered portion of the tapered-to-constricted portion of the rotating growth via 316. Light paths 310 and 308 are not shown in FIG. 3C but may be seen in FIG. 3A. In addition to light paths 344 and 340, there is an emission board 348 to illuminate the light path(s), and detector board 346 to detect the light after the light travels through the cell culture liquid in the rotating growth vial 300.

The motor 338 engages with drive mechanism 312 and is used to rotate the rotating growth vial 300. In some embodiments, motor 338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 336, end housings 352 and lower housing 332 of the cell growth device 330 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 300 is envisioned in some embodiments to be reusable, but preferably is consumable, the other components of the cell growth device 330 are preferably reusable and function as a stand-alone benchtop device or as a module in a multi-module cell processing system.

The processor (not shown) of the cell growth device 330 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 330—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 330, where the second spectrophotometer is used to read a blank at designated intervals.

Figure 3D:
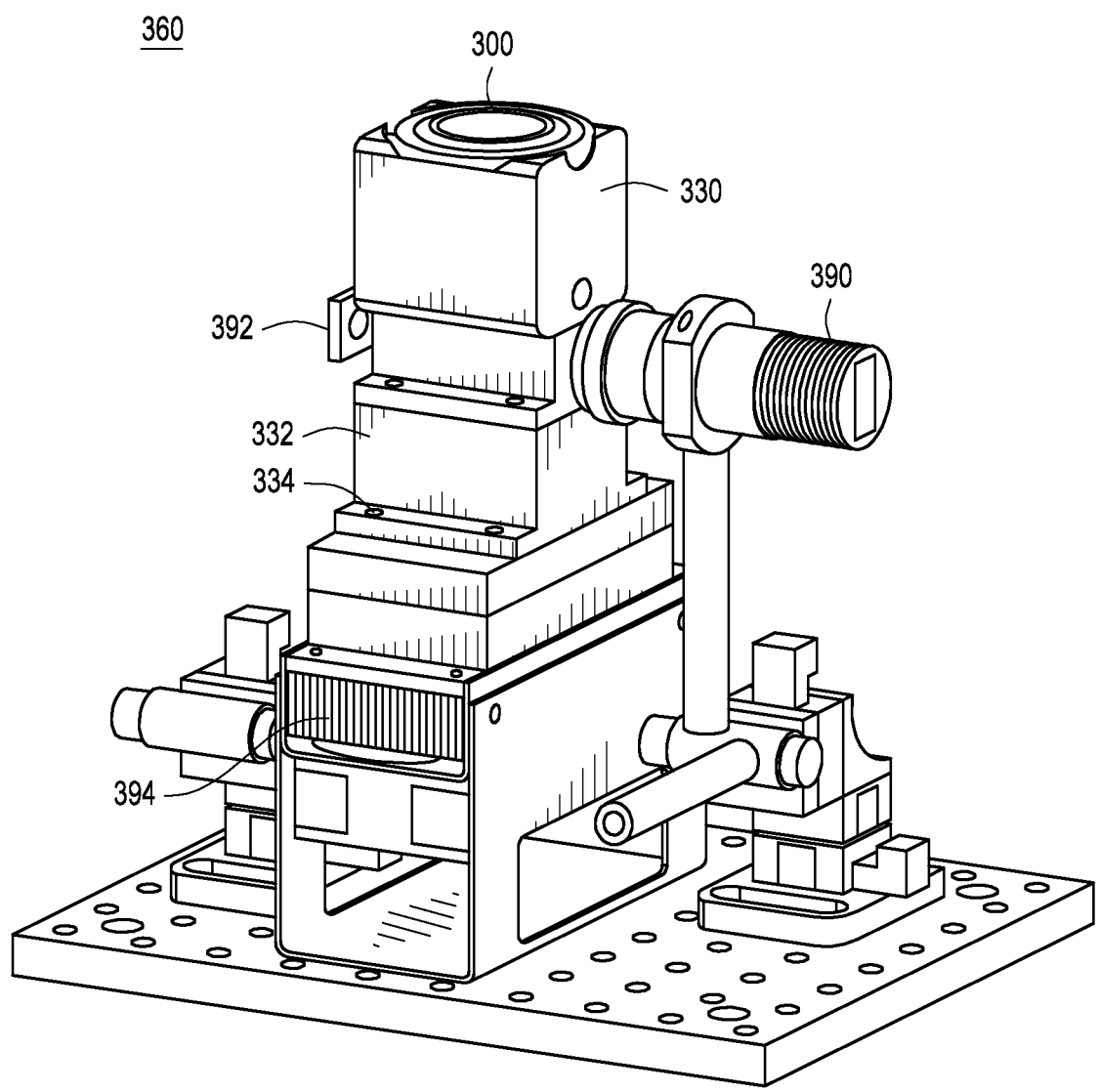
FIG. 3D illustrates the cell growth module of FIG. 3B coupled to LED, detector, and temperature regulating components.

FIG. 3D illustrates a cell growth device 330 as part of an assembly comprising the cell growth device 330 of FIG. 3B coupled to light source 390, detector 392, and thermal components 394. The rotating growth vial 300 is inserted into the cell growth device. Components of the light source 390 and detector 392 (e.g., such as a photodiode with gain control to cover 5-log) are coupled to the main housing of the cell growth device. The lower housing 332 that houses the motor that rotates the rotating growth vial 300 is illustrated, as is one of the flanges 334 that secures the cell growth device 330 to the assembly. Also, the thermal components 394 illustrated are a Peltier device or thermoelectric cooler. In this embodiment, thermal control is accomplished by attachment and electrical integration of the cell growth device 330 to the thermal components 394 via the flange 334 on the base of the lower housing 332. Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 300 is controlled to approximately +/−0.5° C.

In use, cells are inoculated (cells can be pipetted, e.g., from an automated liquid handling system or by a user) into pre-filled growth media of a rotating growth vial 300 by piercing though the foil seal or film. The programmed software of the cell growth device 330 sets the control temperature for growth, typically 30° C., then slowly starts the rotation of the rotating growth vial 300. The cell/growth media mixture slowly moves vertically up the wall due to centrifugal force allowing the rotating growth vial 300 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 330 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 330 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 430 may include additional sensors for measuring, e.g., dissolved oxygen, carbon dioxide, pH, conductivity, and the like. For additional details regarding rotating growth vials and cell growth devices see U.S. Pat. No. 10,435,662, issued 8 Oct. 2019; U.S. Pat. No. 10,443, 031, issued 15 Oct. 2019; and U.S. Ser. No. 16/552,981, filed 7 Aug. 2019.

The Cell Concentration Module

As described above in relation to the rotating growth vial and cell growth module, in order to obtain an adequate number of cells for transformation or transfection, cells typically are grown to a specific optical density in medium appropriate for the growth of the cells of interest; however, for effective transformation or transfection, it is desirable to decrease the volume of the cells as well as render the cells competent via buffer or medium exchange. Thus, one subcomponent or module that is desired in cell processing systems for the processes listed above is a module or component that can grow, perform buffer exchange, and/or concentrate cells and render them competent so that they may be transformed or transfected with the nucleic acids needed for engineering or editing the cell's genome.

Figure 4A:
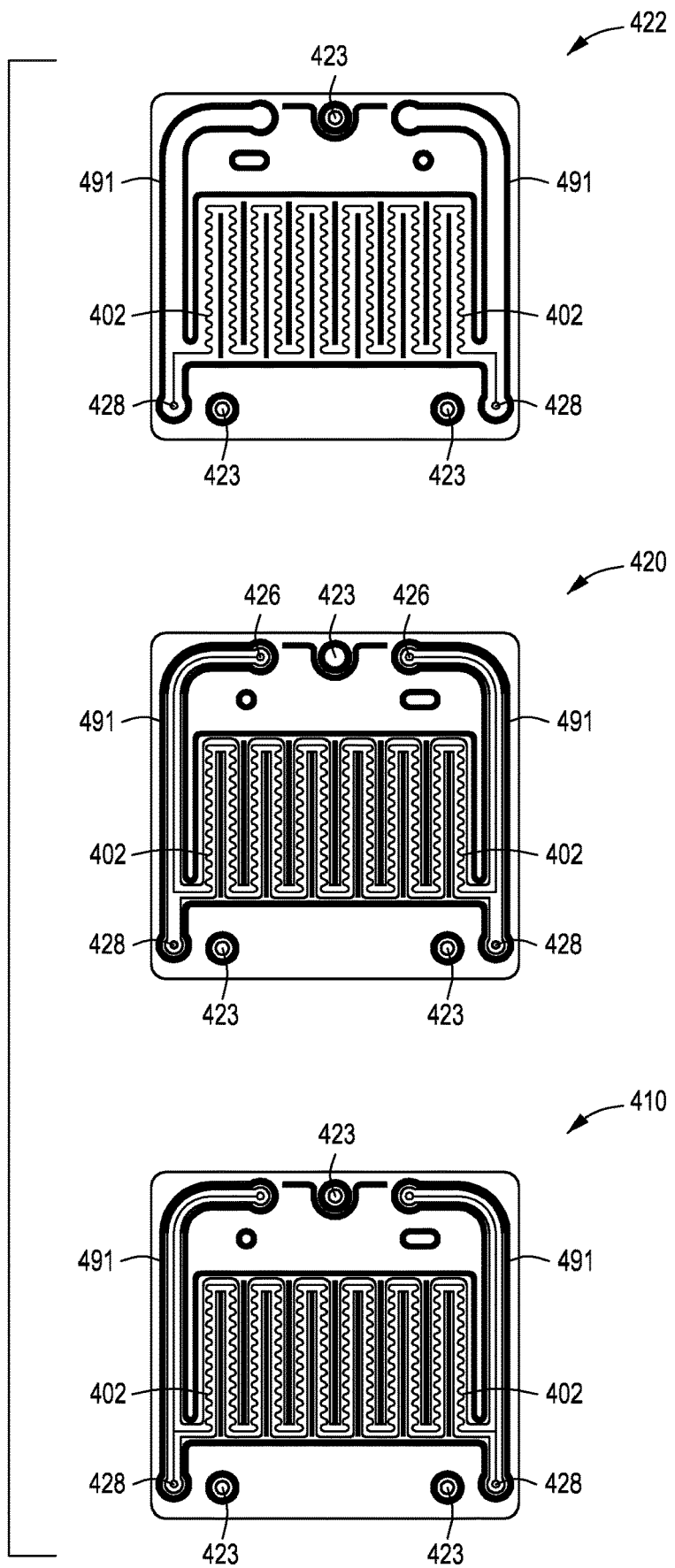
FIG. 4A depicts retentate (top) and permeate (bottom) members for use in a tangential flow filtration module (e.g., cell growth and/or concentration module), as well as the retentate and permeate members assembled into a tangential flow assembly (bottom).

FIG. 4A shows a retentate member 422 (top), permeate member 420 (middle) and a tangential flow assembly 410 (bottom) comprising the retentate member 422, membrane 424 (not seen in FIG. 4A), and permeate member 420 (also not seen). In FIG. 4A, retentate member 422 comprises a tangential flow channel 402, which has a serpentine configuration that initiates at one lower corner of retentate member 422—specifically at retentate port 428—traverses across and up then down and across retentate member 422, ending in the other lower corner of retentate member 422 at a second retentate port 428. Also seen on retentate member 422 are energy directors 491, which circumscribe the region where a membrane or filter (not seen in this FIG. 4A) is seated, as well as interdigitate between areas of channel 402. Energy directors 491 in this embodiment mate with and serve to facilitate ultrasonic welding or bonding of retentate member 422 with permeate/filtrate member 420 via the energy director component 491 on permeate/filtrate member 420 (at right). Additionally, countersinks 423 can be seen, two on the bottom one at the top middle of retentate member 422. Countersinks 423 are used to couple and tangential flow assembly 410 to a reservoir assembly (not seen in this FIG. 4A but see FIG. 4B).

Permeate/filtrate member 420 is seen in the middle of FIG. 4A and comprises, in addition to energy director 491, through-holes for retentate ports 428 at each bottom corner (which mate with the through-holes for retentate ports 428 at the bottom corners of retentate member 422), as well as a tangential flow channel 402 and two permeate/filtrate ports 426 positioned at the top and center of permeate member 420. The tangential flow channel 402 structure in this embodiment has a serpentine configuration and an undulating geometry, although other geometries may be used. Permeate member 420 also comprises countersinks 423, coincident with the countersinks 423 on retentate member 420.

On the left of FIG. 4A is a tangential flow assembly 410 comprising the retentate member 422 and permeate member 420 seen in this FIG. 4A. In this view, retentate member 422 is "on top" of the view, a membrane (not seen in this view of the assembly) would be adjacent and under retentate member 422 and permeate member 420 (also not seen in this view of the assembly) is adjacent to and beneath the membrane. Again countersinks 423 are seen, where the countersinks in the retentate member 422 and the permeate member 420 are coincident and configured to mate with threads or mating elements for the countersinks disposed on a reservoir assembly (not seen in FIG. 4A but see FIG. 4B).

A membrane or filter is disposed between the retentate and permeate members, where fluids can flow through the membrane but cells cannot and are thus retained in the flow channel disposed in the retentate member. Filters or membranes appropriate for use in the TFF device/module are those that are solvent resistant, are contamination free during filtration, and are able to retain the types and sizes of cells of interest. For example, in order to retain small cell types such as bacterial cells, pore sizes can be as low as 0.2 µm, however for other cell types, the pore sizes can be as high as 20 µm. Indeed, the pore sizes useful in the TFF device/module include filters with sizes from 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable non-reactive material including cellulose mixed ester (cellulose nitrate and acetate) (CME), polycarbonate (PC), polyvinylidene fluoride (PVDF), polyethersulfone (PES), polytetrafluoroethylene (PTFE), nylon, glass fiber, or metal substrates as in the case of laser or electrochemical etching.

The length of the channel structure 402 may vary depending on the volume of the cell culture to be grown and the optical density of the cell culture to be concentrated. The length of the channel structure typically is from 60 mm to 300 mm, or from 70 mm to 200 mm, or from 80 mm to 100 mm. The cross-section configuration of the flow channel 402 may be round, elliptical, oval, square, rectangular, trapezoidal, or irregular. If square, rectangular, or another shape with generally straight sides, the cross section may be from about 10 µm to 1000 µm wide, or from 200 µm to 800 µm wide, or from 300 µm to 700 µm wide, or from 400 µm to 600 µm wide; and from about 10 µm to 1000 µm high, or from 200 µm to 800 µm high, or from 300 µm to 700 µm high, or from 400 µm to 600 µm high. If the cross section of the flow channel 102 is generally round, oval or elliptical, the radius of the channel may be from about 50 µm to 1000 µm in hydraulic radius, or from 5 µm to 800 µm in hydraulic radius, or from 200 µm to 700 µm in hydraulic radius, or from 300 µm to 600 µm wide in hydraulic radius, or from about 200 to 500 µm in hydraulic radius. Moreover, the volume of the channel in the retentate 422 and permeate 420 members may be different depending on the depth of the channel in each member.

Figure 4B:
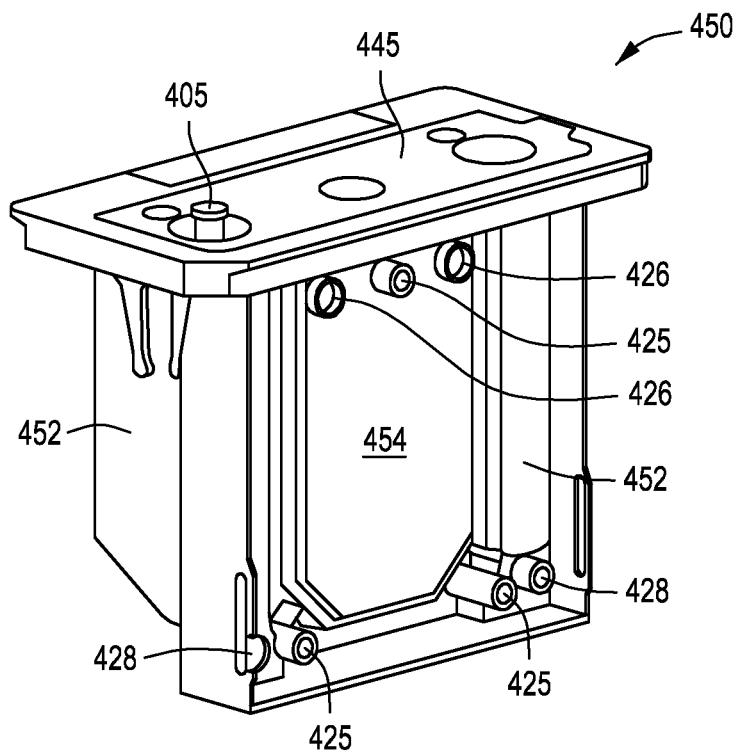
FIG. 4B depicts two side perspective views of a reservoir assembly of a tangential flow filtration module.
Figure 4B:
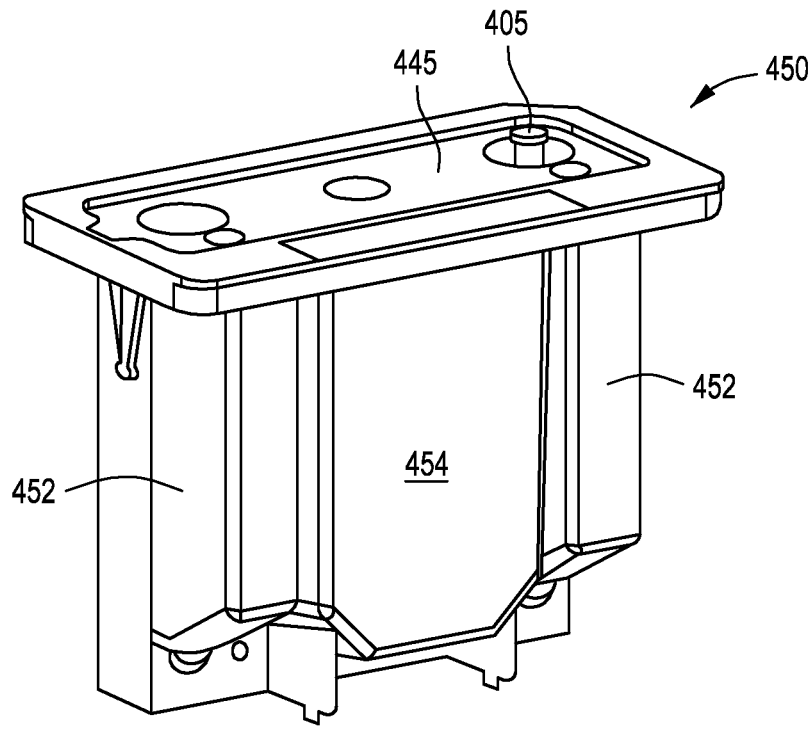

FIG. 4B shows front perspective (right) and rear perspective (left) views of a reservoir assembly 450 configured to be used with the tangential flow assembly 410 seen in FIG. 4A. Seen in the front perspective view (e.g., "front" being the side of reservoir assembly 450 that is coupled to the tangential flow assembly 410 seen in FIG. 4A) are retentate reservoirs 452 on either side of permeate reservoir 454. Also seen are permeate ports 426, retentate ports 428, and three threads or mating elements 425 for countersinks 423 (countersinks 423 not seen in this FIG. 4B). Threads or mating elements 425 for countersinks 423 are configured to mate or couple the tangential flow assembly 410 (seen in FIG. 4A) to reservoir assembly 450. Alternatively or in addition, fasteners, sonic welding or heat stakes may be used to mate or couple the tangential flow assembly 410 to reservoir assembly 450. In addition is seen gasket 445 covering the top of reservoir assembly 450. Gasket 445 is described in detail in relation to FIG. 4E. At left in FIG. 4B is a rear perspective view of reservoir assembly 1250, where "rear" is the side of reservoir assembly 450 that is not coupled to the tangential flow assembly. Seen are retentate reservoirs 452, permeate reservoir 454, and gasket 445.

The TFF device may be fabricated from any robust material in which channels (and channel branches) may be milled including stainless steel, silicon, glass, aluminum, or plastics including cyclic-olefin copolymer (COC), cyclo-olefin polymer (COP), polystyrene, polyvinyl chloride, polyethylene, polyamide, polyethylene, polypropylene, acrylonitrile butadiene, polycarbonate, polyetheretheketone (PEEK), poly(methyl methylacrylate) (PMMA), polysulfone, and polyurethane, and co-polymers of these and other polymers. If the TFF device/module is disposable, preferably it is made of plastic. In some embodiments, the material used to fabricate the TFF device/module is thermally-conductive so that the cell culture may be heated or cooled to a desired temperature. In certain embodiments, the TFF device is formed by precision mechanical machining, laser machining, electro discharge machining (for metal devices); wet or dry etching (for silicon devices); dry or wet etching, powder or sandblasting, photostructuring (for glass devices); or thermoforming, injection molding, hot embossing, or laser machining (for plastic devices) using the materials mentioned above that are amenable to this mass production techniques.

Figure 4C:
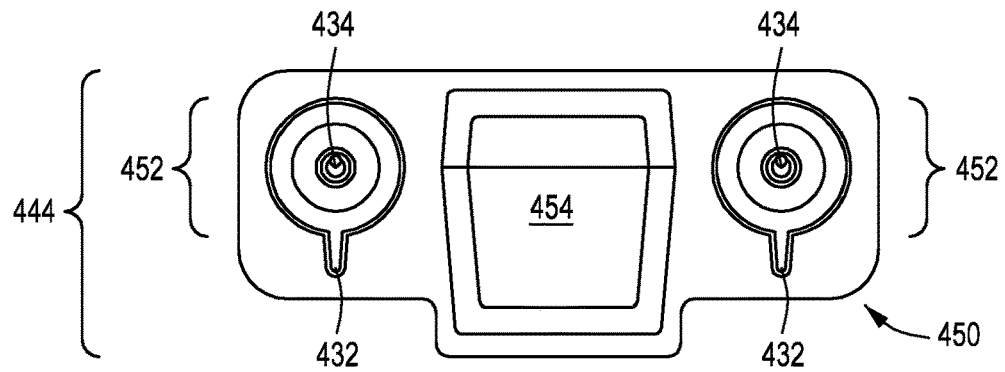
FIGS. 4C-4E depict an exemplary top, with fluidic and pneumatic ports and gasket suitable for the reservoir assemblies shown in FIG. 4B.
Figure 4D:
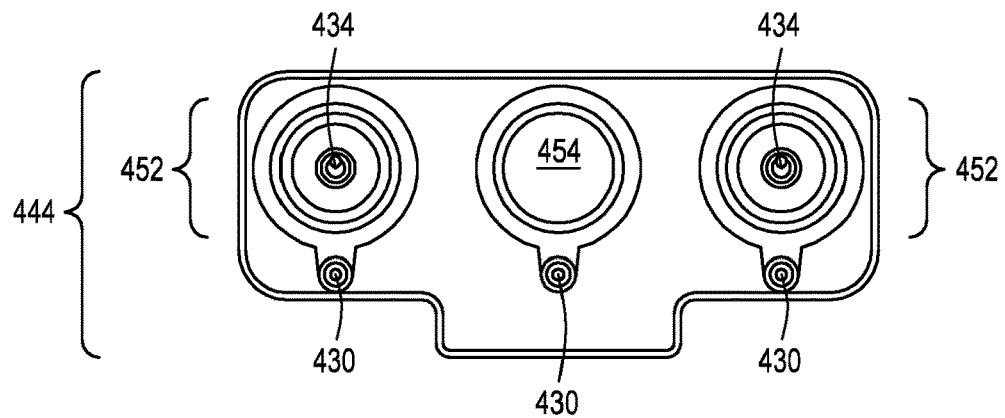
Figure 4E:
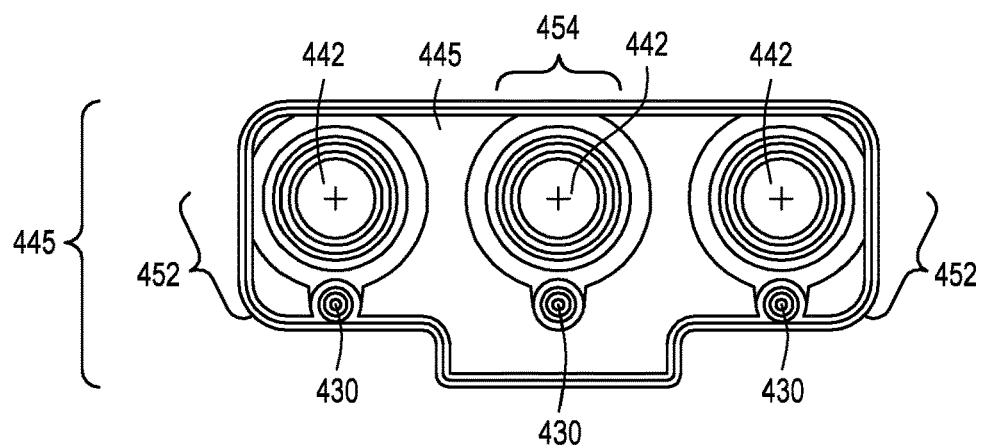

FIG. 4C depicts a top-down view of the reservoir assemblies 450 shown in FIG. 4B. FIG. 4D depicts a cover 444 for reservoir assembly 450 shown in FIGS. 4B and 4E depicts a gasket 445 that in operation is disposed on cover 444 of reservoir assemblies 450 shown in FIG. 4B. FIG. 4C is a top-down view of reservoir assembly 450, showing the tops of the two retentate reservoirs 452, one on either side of permeate reservoir 454. Also seen are grooves 432 that will mate with a pneumatic port (not shown), and fluid channels 434 that reside at the bottom of retentate reservoirs 452, which fluidically couple the retentate reservoirs 452 with the retentate ports 428 (not shown), via the through-holes for the retentate ports in permeate member 420 and membrane 424 (also not shown). FIG. 4D depicts a cover 444 that is configured to be disposed upon the top of reservoir assembly 450. Cover 444 has round cut-outs at the top of retentate reservoirs 452 and permeate/filtrate reservoir 454. Again at the bottom of retentate reservoirs 452 fluid channels 434 can be seen, where fluid channels 434 fluidically couple retentate reservoirs 452 with the retentate ports 428 (not shown). Also shown are three pneumatic ports 430 for each retentate reservoir 452 and permeate/filtrate reservoir 454. FIG. 4E depicts a gasket 445 that is configures to be disposed upon the cover 444 of reservoir assembly 450. Seen are three fluid transfer ports 442 for each retentate reservoir 452 and for permeate/filtrate reservoir 454. Again, three pneumatic ports 430, for each retentate reservoir 452 and for permeate/filtrate reservoir 454, are shown.

The overall work flow for cell growth comprises loading a cell culture to be grown into a first retentate reservoir, optionally bubbling air or an appropriate gas through the cell culture, passing or flowing the cell culture through the first retentate port then tangentially through the TFF channel structure while collecting medium or buffer through one or both of the permeate ports 406, collecting the cell culture through a second retentate port 404 into a second retentate reservoir, optionally adding additional or different medium to the cell culture and optionally bubbling air or gas through the cell culture, then repeating the process, all while measuring, e.g., the optical density of the cell culture in the retentate reservoirs continuously or at desired intervals. Measurements of optical densities (OD) at programmed time intervals are accomplished using a 600 nm Light Emitting Diode (LED) that has been columnated through an optic into the retentate reservoir(s) containing the growing cells. The light continues through a collection optic to the detection system which consists of a (digital) gain-controlled silicone photodiode. Generally, optical density is shown as the absolute value of the logarithm with base 10 of the power transmission factors of an optical attenuator: OD=−log 10 (Power out/Power in). Since OD is the measure of optical attenuation—that is, the sum of absorption, scattering, and reflection—the TFF device OD measurement records the overall power transmission, so as the cells grow and become denser in population, the OD (the loss of signal) increases. The OD system is pre-calibrated against OD standards with these values stored in an on-board memory accessible by the measurement program.

In the channel structure, the membrane bifurcating the flow channels retains the cells on one side of the membrane (the retentate side 422) and allows unwanted medium or buffer to flow across the membrane into a filtrate or permeate side (e.g., permeate member 420) of the device. Bubbling air or other appropriate gas through the cell culture both aerates and mixes the culture to enhance cell growth. During the process, medium that is removed during the flow through the channel structure is removed through the permeate/filtrate ports 406. Alternatively, cells can be grown in one reservoir with bubbling or agitation without passing the cells through the TFF channel from one reservoir to the other.

The overall work flow for cell concentration using the TFF device/module involves flowing a cell culture or cell sample tangentially through the channel structure. As with the cell growth process, the membrane bifurcating the flow channels retains the cells on one side of the membrane and allows unwanted medium or buffer to flow across the membrane into a permeate/filtrate side (e.g., permeate member 420) of the device. In this process, a fixed volume of cells in medium or buffer is driven through the device until the cell sample is collected into one of the retentate ports 404, and the medium/buffer that has passed through the membrane is collected through one or both of the permeate/filtrate ports 406. All types of prokaryotic and eukaryotic cells—both adherent and non-adherent cells—can be grown in the TFF device. Adherent cells may be grown on beads or other cell scaffolds suspended in medium that flow through the TFF device.

The medium or buffer used to suspend the cells in the cell concentration device/module may be any suitable medium or buffer for the type of cells being transformed or transfected, such as LB, SOC, TPD, YPG, YPAD, MEM, DMEM, IMDM, RPMI, Hanks', PBS and Ringer's solution, where the media may be provided in a reagent cartridge as part of a kit. For culture of adherent cells, cells may be disposed on beads, microcarriers, or other type of scaffold suspended in medium. Most normal mammalian tissue-derived cells—except those derived from the hematopoietic system—are anchorage dependent and need a surface or cell culture support for normal proliferation. In the rotating growth vial described herein, microcarrier technology is leveraged. Microcarriers of particular use typically have a diameter of 100-300 µm and have a density slightly greater than that of the culture medium (thus facilitating an easy separation of cells and medium for, e.g., medium exchange) yet the density must also be sufficiently low to allow complete suspension of the carriers at a minimum stirring rate in order to avoid hydrodynamic damage to the cells. Many different types of microcarriers are available, and different microcarriers are optimized for different types of cells. There are positively charged carriers, such as Cytodex 1 (dextran-based, GE Healthcare), DE-52 (cellulose-based, Sigma-Aldrich Labware), DE-53 (cellulose-based, Sigma-Aldrich Labware), and HLX 11-170 (polystyrene-based); collagen- or ECM- (extracellular matrix) coated carriers, such as Cytodex 3 (dextran-based, GE Healthcare) or HyQ-sphere Pro-F 102-4 (polystyrene-based, Thermo Scientific); non-charged carriers, like HyQ-sphere P 102-4 (Thermo Scientific); or macroporous carriers based on gelatin (Culti-sphere, Percell Biolytica) or cellulose (Cytopore, GE Healthcare).

In both the cell growth and concentration processes, passing the cell sample through the TFF device and collecting the cells in one of the retentate ports 404 while collecting the medium in one of the permeate/filtrate ports 406 is considered "one pass" of the cell sample. The transfer between retentate reservoirs "flips" the culture. The retentate and permeatee ports collecting the cells and medium, respectively, for a given pass reside on the same end of TFF device/module with fluidic connections arranged so that there are two distinct flow layers for the retentate and permeate/filtrate sides, but if the retentate port 404 resides on the retentate member of device/module (that is, the cells are driven through the channel above the membrane and the filtrate (medium) passes to the portion of the channel below the membrane), the permeate/filtrate port 406 will reside on the permeate member of device/module and vice versa (that is, if the cell sample is driven through the channel below the membrane, the filtrate (medium) passes to the portion of the channel above the membrane). Due to the high pressures used to transfer the cell culture and fluids through the flow channel of the TFF device, the effect of gravity is negligible.

At the conclusion of a "pass" in either of the growth and concentration processes, the cell sample is collected by passing through the retentate port 404 and into the retentate reservoir (not shown). To initiate another "pass", the cell sample is passed again through the TFF device, this time in a flow direction that is reversed from the first pass. The cell sample is collected by passing through the retentate port 404 and into retentate reservoir (not shown) on the opposite end of the device/module from the retentate port 404 that was used to collect cells during the first pass. Likewise, the medium/buffer that passes through the membrane on the second pass is collected through the permeate port 406 on the opposite end of the device/module from the permeate port 406 that was used to collect the filtrate during the first pass, or through both ports. This alternating process of passing the retentate (the concentrated cell sample) through the device/module is repeated until the cells have been grown to a desired optical density, and/or concentrated to a desired volume, and both permeate ports (i.e., if there are more than one) can be open during the passes to reduce operating time. In addition, buffer exchange may be effected by adding a desired buffer (or fresh medium) to the cell sample in the retentate reservoir, before initiating another "pass", and repeating this process until the old medium or buffer is diluted and filtered out and the cells reside in fresh medium or buffer. Note that buffer exchange and cell growth may (and typically do) take place simultaneously, and buffer exchange and cell concentration may (and typically do) take place simultaneously. For further information and alternative embodiments on TFFs see, e.g., U.S. Ser. No. 16/516,701, filed 5 Sep. 2019.

The Cell Transformation Module

Figure 5A:
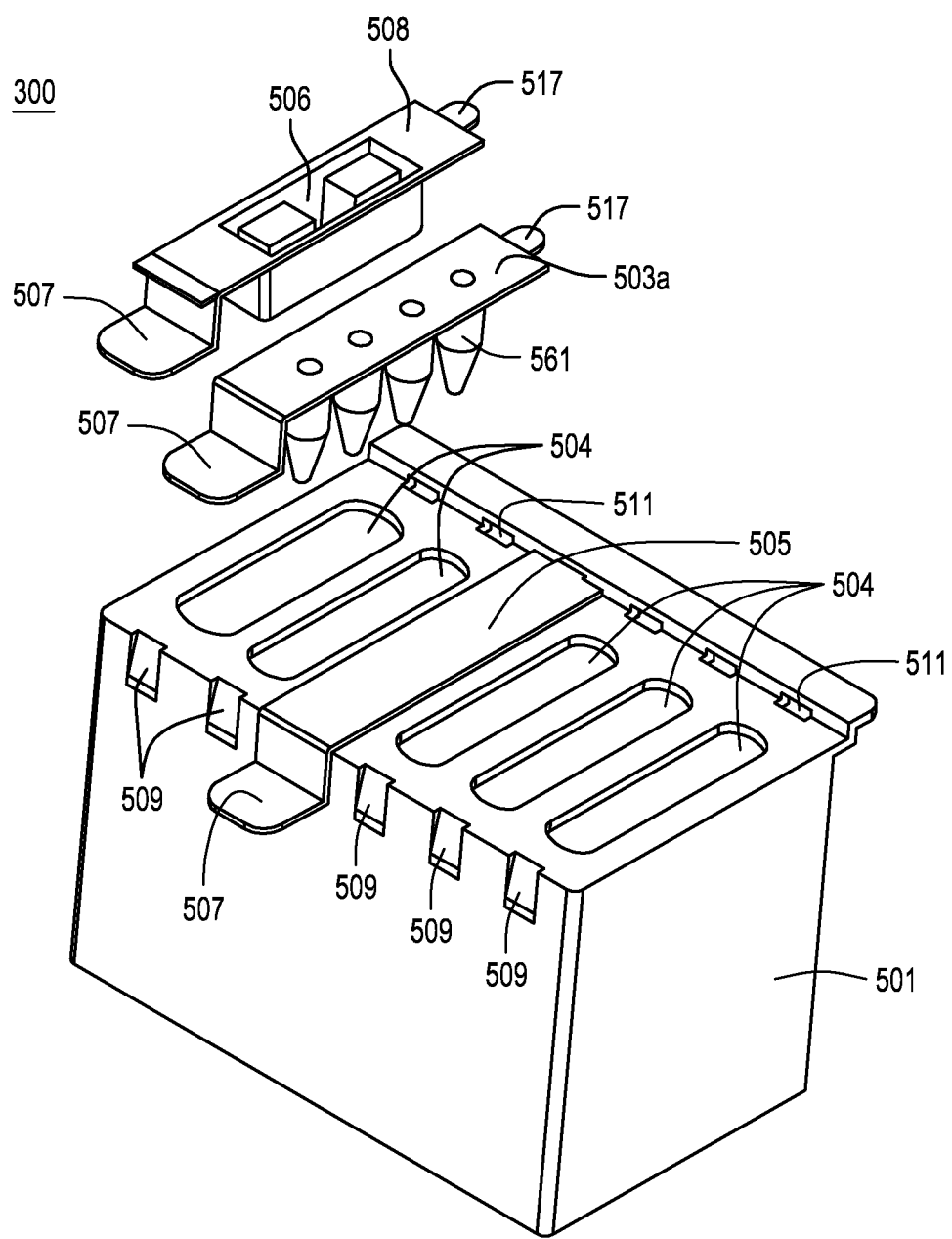
FIG. 5A depicts an exemplary combination reagent cartridge and electroporation device (e.g., transformation module) that may be used in a multi-module cell processing instrument.

FIG. 5A depicts a partially assembled reagent cartridge 500, comprising a cover 501, reservoirs 504, a reservoir cover 505 comprising an outer flange 507 with an inner flange (not shown), that engages with an indentation (indentations 509 seen with uncovered reservoirs 504). Outer flange 507 provides a grip for handling the reservoir cover 505 or other inserts for the reservoirs described below. Reservoirs 504 in reagent cartridge 500 in FIG. 5A accommodate strips of co-joined tubes, including as shown here a strip of co-joined large tubes 503a (with individual tubes 561). The reservoirs 504 in the embodiment of the reagent cartridge 500 shown in FIG. 5A are "slot"—shaped and are configured to be "universal": that is, the slot-shaped reservoirs 504 are configured to accommodate many different types of reservoir inserts. The strip of co-joined large tubes 503a comprises an outer flange 507 with an inner flange (not shown), configured to engage with an indentation 509 in the cover 501 of the reagent cartridge 500, as well as a tab 517 configured to engage with tab engagement member 511 in cover 501. Any or all reservoir inserts may be covered by a protective foil, film or peel-off strip to maintain sterility of the reservoir and the contents thereof (not shown). In addition, in certain embodiments the material used to fabricate the cartridge is thermally-conductive, as in certain embodiments the cartridge 500 contacts a thermal device (not shown), such as a Peltier device or thermoelectric cooler, that heats or cools reagents in the reagent reservoirs or reservoirs 504.

Also shown in FIG. 5A is an insert 508 comprising a flow-through electroporation device 506. The flow-through electroporation device 506 is configured to transform or transfect nucleic acids or other materials into cells and is described in detail in relation to FIGS. 5B-5F. The flow-through electroporation device insert 508 comprises both a tab 517, and an outer flange 507. As with the strip of co-joined large tubes 503a, the outer flange 507 comprises an inner flange (not shown), configured to engage with an indentation 509 in the cover 501 of the reagent cartridge 500, as well as a tab 517 configured to engage with tab engagement member 511 in cover 501.

Reagents such as cell samples, enzymes, buffers, nucleic acid vectors, expression cassettes, proteins or peptides, reaction components (such as, e.g., $MgCl_2$, dNTPs, nucleic acid assembly reagents, gap repair reagents, and the like), wash solutions, ethanol, and magnetic beads for nucleic acid purification and isolation, etc. may be positioned in the reagent cartridge at a known position. In some embodiments of cartridge 500, the cartridge comprises a script (not shown) readable by a processor (not shown) for dispensing the reagents. Also, the cartridge 500 as one component in an automated multi-module cell processing instrument may comprise a script specifying two, three, four, five, ten or more processes to be performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components/modules of the automated multi-module cell processing instrument or system may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing instrument, or, e.g., reagents for protein expression and a script that specifies the process steps for performing protein expression in an automated multi-module cell processing instrument.

For example, the reagent cartridge may comprise a script to pipette competent cells from a reservoir, transfer the cells to a transformation module, pipette a nucleic acid solution comprising a vector with expression cassette from another reservoir in the reagent cartridge, transfer the nucleic acid solution to the transformation module, initiate the transformation process for a specified time, then move the transformed cells to yet another reservoir in the reagent cassette or to another module such as a cell growth module in the automated multi-module cell processing instrument. In another example, the reagent cartridge may comprise a script to transfer a nucleic acid solution comprising a vector from a reservoir in the reagent cassette, nucleic acid solution comprising editing oligonucleotide cassettes in a reservoir in the reagent cassette, and a nucleic acid assembly mix from another reservoir to the nucleic acid assembly/desalting module, if present. The script may also specify process steps performed by other modules in the automated multi-module cell processing instrument. For example, the script may specify that the nucleic acid assembly/desalting reservoir be heated to 50° C. for 30 min to generate an assembled product; and desalting and resuspension of the assembled product via magnetic bead-based nucleic acid purification involving a series of pipette transfers and mixing of magnetic beads, ethanol wash, and buffer.

As described in relation to FIGS. 5B and 5C below, the exemplary reagent cartridges for use in the automated multi-module cell processing instruments may include one or more electroporation devices, preferably flow-through electroporation (FTEP) devices. In yet other embodiments, the reagent cartridge is separate from the transformation module. Electroporation is a widely-used method for permeabilization of cell membranes that works by temporarily generating pores in the cell membranes with electrical stimulation. Applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. In traditional electroporation devices, the cells and material to be electroporated into the cells (collectively "the cell sample") are placed in a cuvette embedded with two flat electrodes for electrical discharge. For example, Bio-Rad (Hercules, Calif.) makes the GENE PULSER XCELL™ line of products to electroporate cells in cuvettes. Traditionally, electroporation requires high field strength; however, the flow-through electroporation devices included in the reagent cartridges achieve high efficiency cell electroporation with low toxicity. The reagent cartridges of the disclosure allow for particularly easy integration with robotic liquid handling instrumentation that is typically used in automated instruments and systems such as air displacement pipettors. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

Figure 5C:
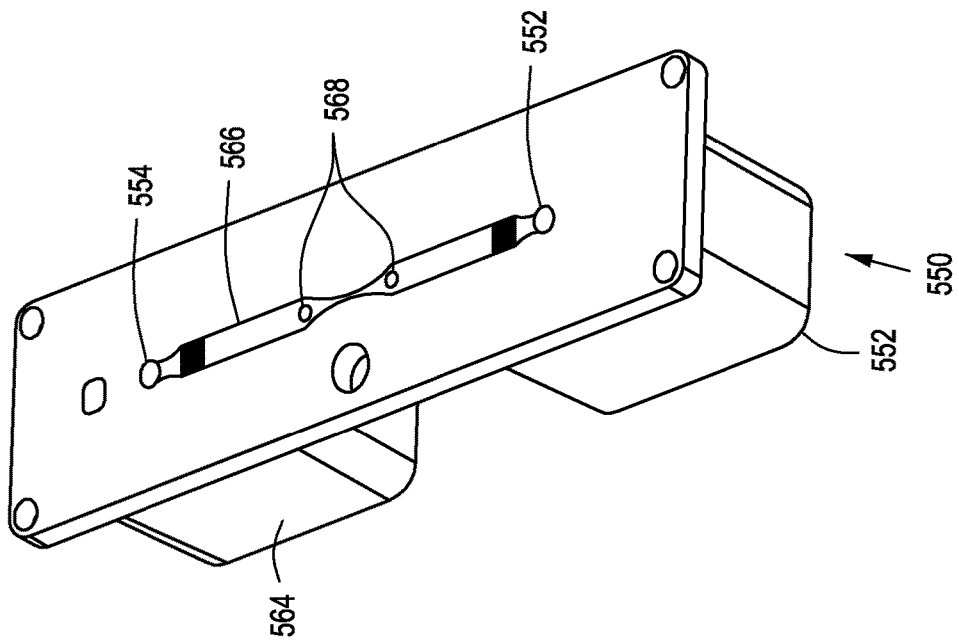
FIG. 5C depicts a bottom perspective view of one embodiment of an exemplary flow-through electroporation device that may be part of a reagent cartridge.
Figure 5B:
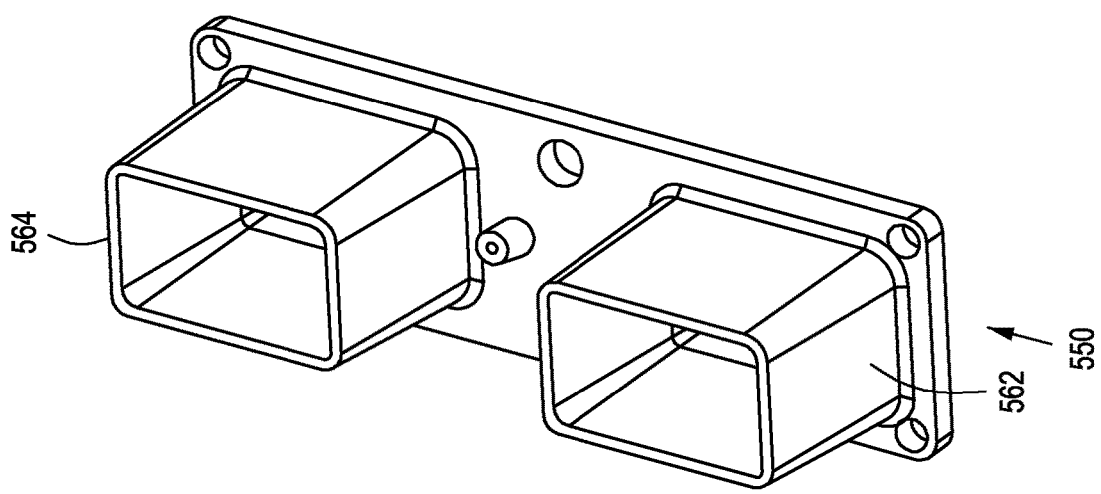
FIG. 5B is a top perspective view of one embodiment of an exemplary flow-through electroporation device that may be part of a reagent cartridge.

FIGS. 5B and 5C are top perspective and bottom perspective views, respectively, of an exemplary FTEP device 550 that may be part of (e.g., a component in) reagent cartridge 500 in FIG. 5A or may be a stand-alone module; that is, not a part of a reagent cartridge or other module. FIG. 5B depicts an FTEP device 550. The FTEP device 550 has wells that define cell sample inlets 552 and cell sample outlets 554. FIG. 5C is a bottom perspective view of the FTEP device 550 of FIG. 5B. An inlet well 552 and an outlet well 554 can be seen in this view. Also seen in FIG. 5C are the bottom of an inlet 562 corresponding to well 552, the bottom of an outlet 564 corresponding to the outlet well 554, the bottom of a defined flow channel 566 and the bottom of two electrodes 568 on either side of flow channel 566. The FTEP devices may comprise push-pull pneumatic means to allow multi-pass electroporation procedures; that is, cells to electroporated may be "pulled" from the inlet toward the outlet for one pass of electroporation, then be "pushed" from the outlet end of the FTEP device toward the inlet end to pass between the electrodes again for another pass of electroporation. Further, this process may be repeated one to many times. For additional information regarding FTEP devices, see, e.g., U.S. Pat. No. 10,435,713, issued 8 Oct. 2019; U.S. Pat. No. 10,443,074, issued 15 Oct. 2019; U.S. Pat. No. 10,323,258, issued 18 Jun. 2019; U.S. Pat. No. 10,568,288, issued 17 Dec. 2019; and U.S. Pat. No. 10,415,058, issued 17 Sep. 2019. Further, other embodiments of the reagent cartridge may provide or accommodate electroporation devices that are not configured as FTEP devices, such as those described in U.S. Ser. No. 16/109,156, filed 22 Aug. 2018. For reagent cartridges useful in the present automated multi-module cell processing instruments, see, e.g., U.S. Pat. No. 10,376,889, issued 13 Aug. 2019; U.S. Pat. No. 10,406,525, issued 10 Sep. 2019; U.S. Pat. No. 10,478,822, issued 19 Nov. 2019; and U.S. Ser. No. 16/596,940, filed 9 Oct. 2019.

Figure 5D:
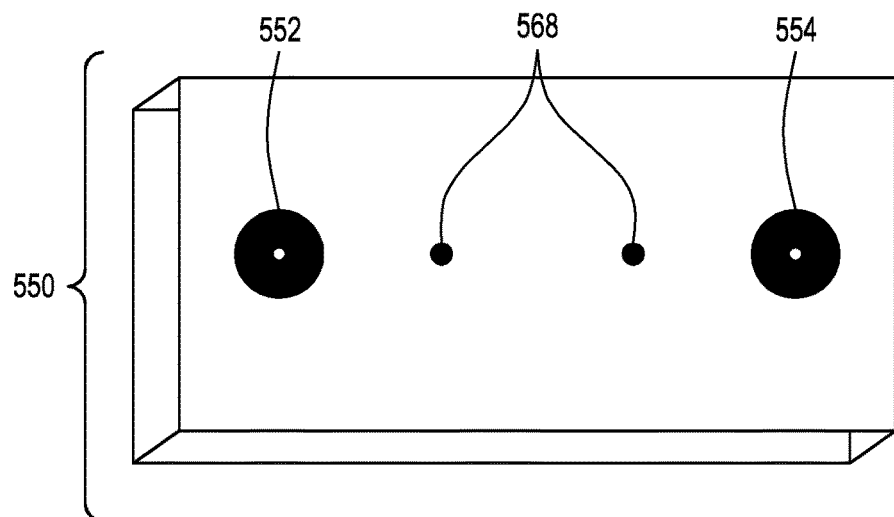
FIGS. 5D-5F depict a top perspective view, a top view of a cross section, and a side perspective view of a cross section of an FTEP device useful in a multi-module automated cell processing instrument such as that shown in FIGS. 2A-2C.
Figure 5E:
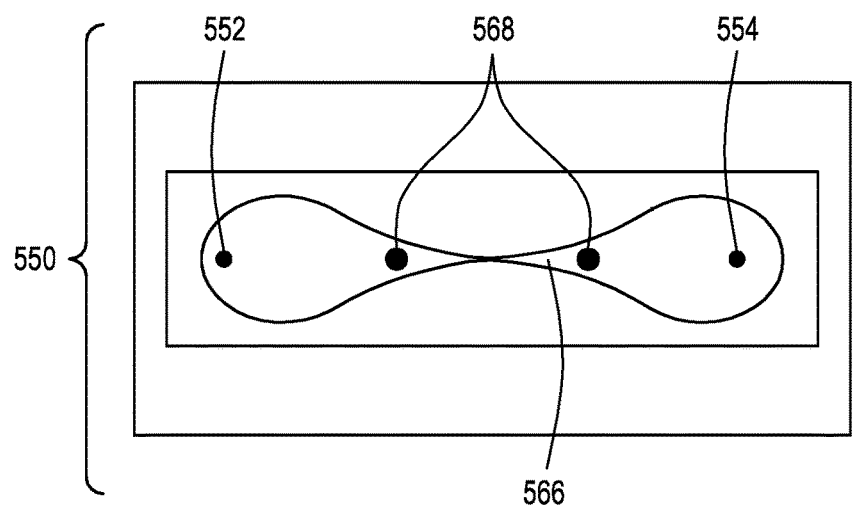
Figure 5F:
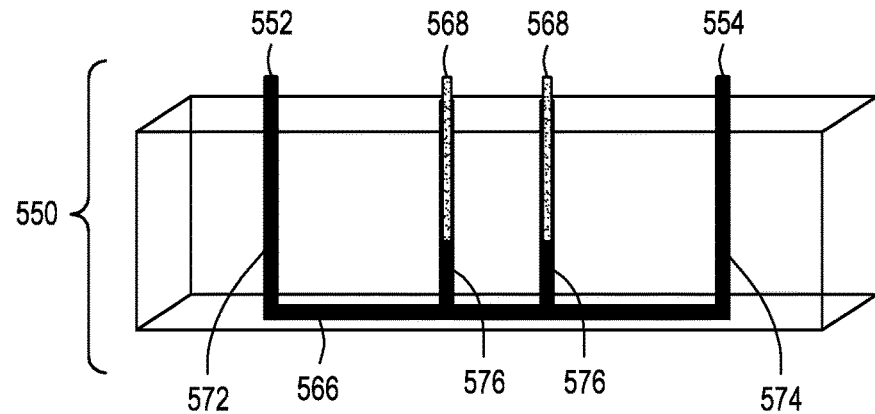

Additional details of the FTEP devices are illustrated in FIGS. 5D-5F. Note that in the FTEP devices in FIGS. 5D-5F the electrodes are placed such that a first electrode is placed between an inlet and a narrowed region of the flow channel, and the second electrode is placed between the narrowed region of the flow channel and an outlet. FIG. 5D shows a top planar view of an FTEP device 550 having an inlet 552 for introducing a fluid containing cells and exogenous material into FTEP device 550 and an outlet 554 for removing the transformed cells from the FTEP following electroporation. The electrodes 568 are introduced through channels (not shown) in the device. FIG. 5E shows a cutaway view from the top of the FTEP device 550, with the inlet 552, outlet 554, and electrodes 568 positioned with respect to a flow channel 566. FIG. 5F shows a side cutaway view of FTEP device 550 with the inlet 552 and inlet channel 572, and outlet 554 and outlet channel 574. The electrodes 568 are positioned in electrode channels 576 so that they are in fluid communication with the flow channel 566, but not directly in the path of the cells traveling through the flow channel 566. Note that the first electrode is placed between the inlet and the narrowed region of the flow channel, and the second electrode is placed between the narrowed region of the flow channel and the outlet. The electrodes 568 in this aspect of the device are positioned in the electrode channels 576 which are generally perpendicular to the flow channel 566 such that the fluid containing the cells and exogenous material flows from the inlet channel 572 through the flow channel 566 to the outlet channel 574, and in the process fluid flows into the electrode channels 376 to be in contact with the electrodes 568. In this aspect, the inlet channel, outlet channel and electrode channels all originate from the same planar side of the device. In certain aspects, however, the electrodes may be introduced from a different planar side of the FTEP device than the inlet and outlet channels.

In the FTEP devices of the disclosure, the toxicity level of the transformation results in greater than 30% viable cells after electroporation, preferably greater than 35%, 40%, 45%, 50%, 55%, 60%, 70%, 75%, 80%, 85%, 90%, 95% or even 99% viable cells following transformation, depending on the cell type and the nucleic acids being introduced into the cells.

The housing of the FTEP device can be made from many materials depending on whether the FTEP device is to be reused, autoclaved, or is disposable, including stainless steel, silicon, glass, resin, polyvinyl chloride, polyethylene, polyamide, polystyrene, polyethylene, polypropylene, acrylonitrile butadiene, polycarbonate, polyetheretheketone (PEEK), polysulfone and polyurethane, co-polymers of these and other polymers. Similarly, the walls of the channels in the device can be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Preferred materials include crystal styrene, cyclo-olefin polymer (COP) and cyclic olephin co-polymers (COC), which allow the device to be formed entirely by injection molding in one piece with the exception of the electrodes and, e.g., a bottom sealing film if present.

The FTEP devices described herein (or portions of the FTEP devices) can be created or fabricated via various techniques, e.g., as entire devices or by creation of structural layers that are fused or otherwise coupled. For example, for metal FTEP devices, fabrication may include precision mechanical machining or laser machining; for silicon FTEP devices, fabrication may include dry or wet etching; for glass FTEP devices, fabrication may include dry or wet etching, powderblasting, sandblasting, or photostructuring; and for plastic FTEP devices fabrication may include thermoforming, injection molding, hot embossing, or laser machining. The components of the FTEP devices may be manufactured separately and then assembled, or certain components of the FTEP devices (or even the entire FTEP device except for the electrodes) may be manufactured (e.g., using 3D printing) or molded (e.g., using injection molding) as a single entity, with other components added after molding. For example, housing and channels may be manufactured or molded as a single entity, with the electrodes later added to form the FTEP unit. Alternatively, the FTEP device may also be formed in two or more parallel layers, e.g., a layer with the horizontal channel and filter, a layer with the vertical channels, and a layer with the inlet and outlet ports, which are manufactured and/or molded individually and assembled following manufacture.

In specific aspects, the FTEP device can be manufactured using a circuit board as a base, with the electrodes, filter and/or the flow channel formed in the desired configuration on the circuit board, and the remaining housing of the device containing, e.g., the one or more inlet and outlet channels and/or the flow channel formed as a separate layer that is then sealed onto the circuit board. The sealing of the top of the housing onto the circuit board provides the desired configuration of the different elements of the FTEP devices of the disclosure. Also, two to many FTEP devices may be manufactured on a single substrate, then separated from one another thereafter or used in parallel. In certain embodiments, the FTEP devices are reusable and, in some embodiments, the FTEP devices are disposable. In additional embodiments, the FTEP devices may be autoclavable.

The electrodes 408 can be formed from any suitable metal, such as copper, stainless steel, titanium, aluminum, brass, silver, rhodium, gold or platinum, or graphite. One preferred electrode material is alloy 303 (UNS330300) austenitic stainless steel. An applied electric field can destroy electrodes made from of metals like aluminum. If a multiple-use (i.e., non-disposable) flow-through FTEP device is desired-as opposed to a disposable, one-use flow-through FTEP device-the electrode plates can be coated with metals resistant to electrochemical corrosion. Conductive coatings like noble metals, e.g., gold, can be used to protect the electrode plates.

As mentioned, the FTEP devices may comprise push-pull pneumatic means to allow multi-pass electroporation procedures; that is, cells to electroporated may be "pulled" from the inlet toward the outlet for one pass of electroporation, then be "pushed" from the outlet end of the flow-through FTEP device toward the inlet end to pass between the electrodes again for another pass of electroporation. This process may be repeated one to many times.

Depending on the type of cells to be electroporated (e.g., bacterial, yeast, mammalian) and the configuration of the electrodes, the distance between the electrodes in the flow channel can vary widely. For example, where the flow channel decreases in width, the flow channel may narrow to between 10 µm and 5 mm, or between 25 µm and 3 mm, or between 50 µm and 2 mm, or between 75 µm and 1 mm. The distance between the electrodes in the flow channel may be between 1 mm and 10 mm, or between 2 mm and 8 mm, or between 3 mm and 7 mm, or between 4 mm and 6 mm. The overall size of the FTEP device may be from 3 cm to 15 cm in length, or 4 cm to 12 cm in length, or 4.5 cm to 10 cm in length. The overall width of the FTEP device may be from 0.5 cm to 5 cm, or from 0.75 cm to 3 cm, or from 1 cm to 2.5 cm, or from 1 cm to 1.5 cm.

The region of the flow channel that is narrowed is wide enough so that at least two cells can fit in the narrowed portion side-by-side. For example, a typical bacterial cell is 1 µm in diameter; thus, the narrowed portion of the flow channel of the FTEP device used to transform such bacterial cells will be at least 2 µm wide. In another example, if a mammalian cell is approximately 50 µm in diameter, the narrowed portion of the flow channel of the FTEP device used to transform such mammalian cells will be at least 100 µm wide. That is, the narrowed portion of the FTEP device will not physically contort or "squeeze" the cells being transformed.

In embodiments of the FTEP device where reservoirs are used to introduce cells and exogenous material into the FTEP device, the reservoirs range in volume from 100 µL to 10 mL, or from 500 µL to 75 mL, or from 1 mL to 5 mL. The flow rate in the FTEP ranges from 0.1 mL to 5 mL per minute, or from 0.5 mL to 3 mL per minute, or from 1.0 mL to 2.5 mL per minute. The pressure in the FTEP device ranges from 1-30 psi, or from 2-10 psi, or from 3-5 psi.

To avoid different field intensities between the electrodes, the electrodes should be arranged in parallel. Furthermore, the surface of the electrodes should be as smooth as possible without pin holes or peaks. Electrodes having a roughness Rz of 1 to 10 µm are preferred. In another embodiment of the invention, the flow-through electroporation device comprises at least one additional electrode which applies a ground potential to the FTEP device. Flow-through electroporation devices (either as a stand-alone instrument or as a module in an automated multi-module system) are described in, e.g., U.S. Ser. No. 16/147,120, filed 28 Sep. 2018; Ser. No. 16/147,353, filed 28 Sep. 2018; Ser. No. 16/147,865, filed 30 Sep. 2018; and Ser. No. 16/426,310, filed 30 May 2019; and U.S. Pat. No. 10,323,258, issued 18 Jun. 2019.

Cell Singulation and Enrichment Device

Figure 6A:
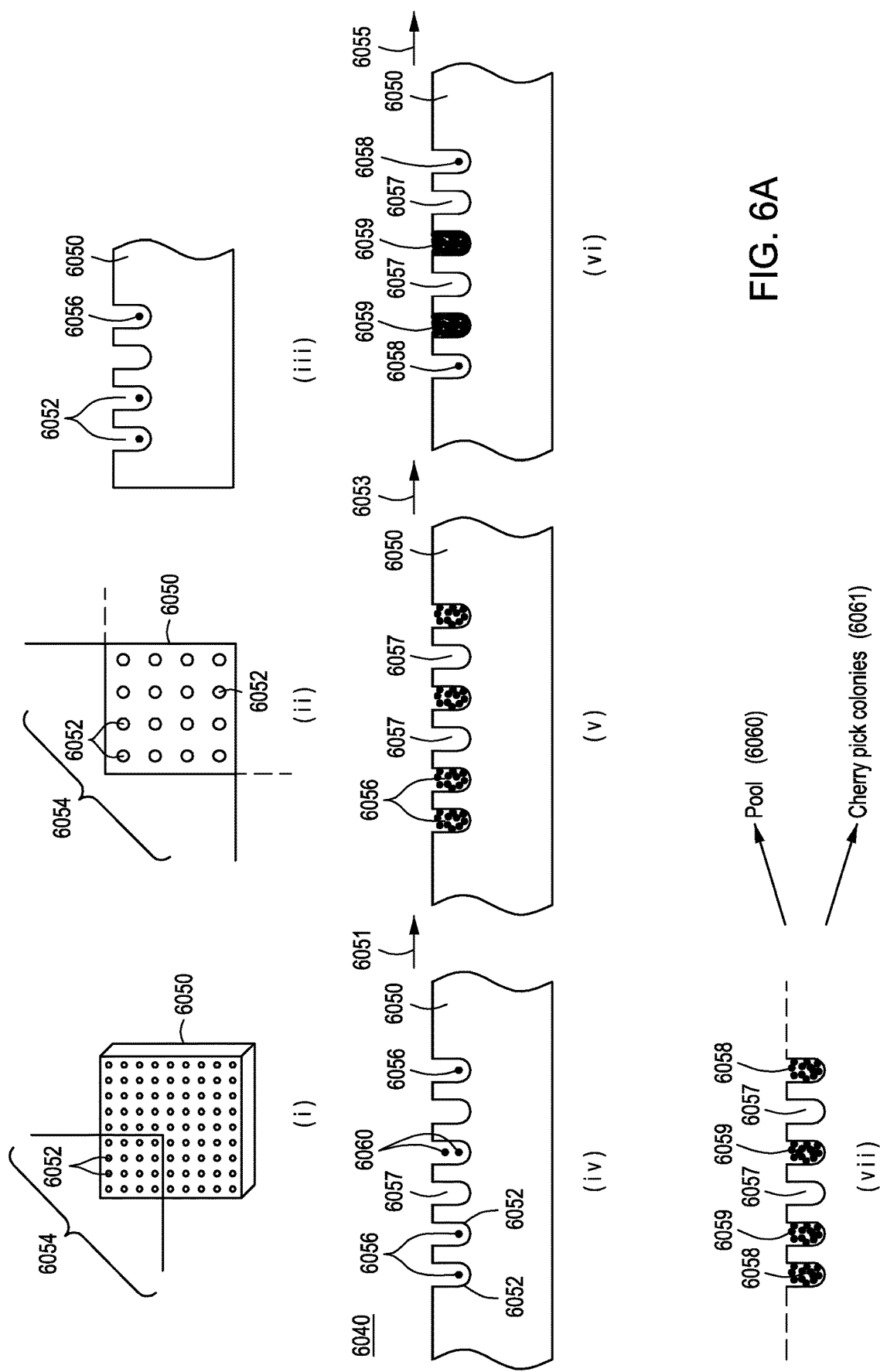
FIG. 6A depicts a simplified graphic of a workflow for singulating, editing and normalizing cells in a solid wall device.

FIG. 6A depicts a solid wall device 6050 and a workflow for singulating cells in microwells in the solid wall device. At the top left of the figure (i), there is depicted solid wall device 6050 with microwells 6052. A section 6054 of substrate 6050 is shown at (ii), also depicting microwells 6052. At (iii), a side cross-section of solid wall device 6050 is shown, and microwells 6052 have been loaded, where, in this embodiment, Poisson or substantial Poisson loading has taken place; that is, each microwell has one or no cells, and the likelihood that any one microwell has more than one cell is low. At (iv), workflow 6040 is illustrated where substrate 6050 having microwells 6052 shows microwells 6056 with one cell per microwell, microwells 6057 with no cells in the microwells, and one microwell 6060 with two cells in the microwell. In step 6051, the cells in the microwells are allowed to double approximately 2-150 times to form clonal colonies (v), then editing is allowed to occur 6053.

After editing 6053, many cells in the colonies of cells that have been edited die as a result of the double-strand cuts caused by active editing and there is a lag in growth for the edited cells that do survive but must repair and recover following editing (microwells 6058), where cells that do not undergo editing thrive (microwells 6059) (vi). All cells are allowed to continue grow to establish colonies and normalize, where the colonies of edited cells in microwells 6058 catch up in size and/or cell number with the cells in microwells 6059 that do not undergo editing (vii). Once the cell colonies are normalized, either pooling 6060 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 6058) are identified and selected 6061 (e.g., "cherry picked") resulting in even greater enrichment of edited cells.

In growing the cells, the medium used will depend, of course, on the type of cells being edited—e.g., bacterial, yeast or mammalian. For example, medium for yeast cell growth includes LB, SOC, TPD, YPG, YPAD, MEM and DMEM.

Figure 6B:
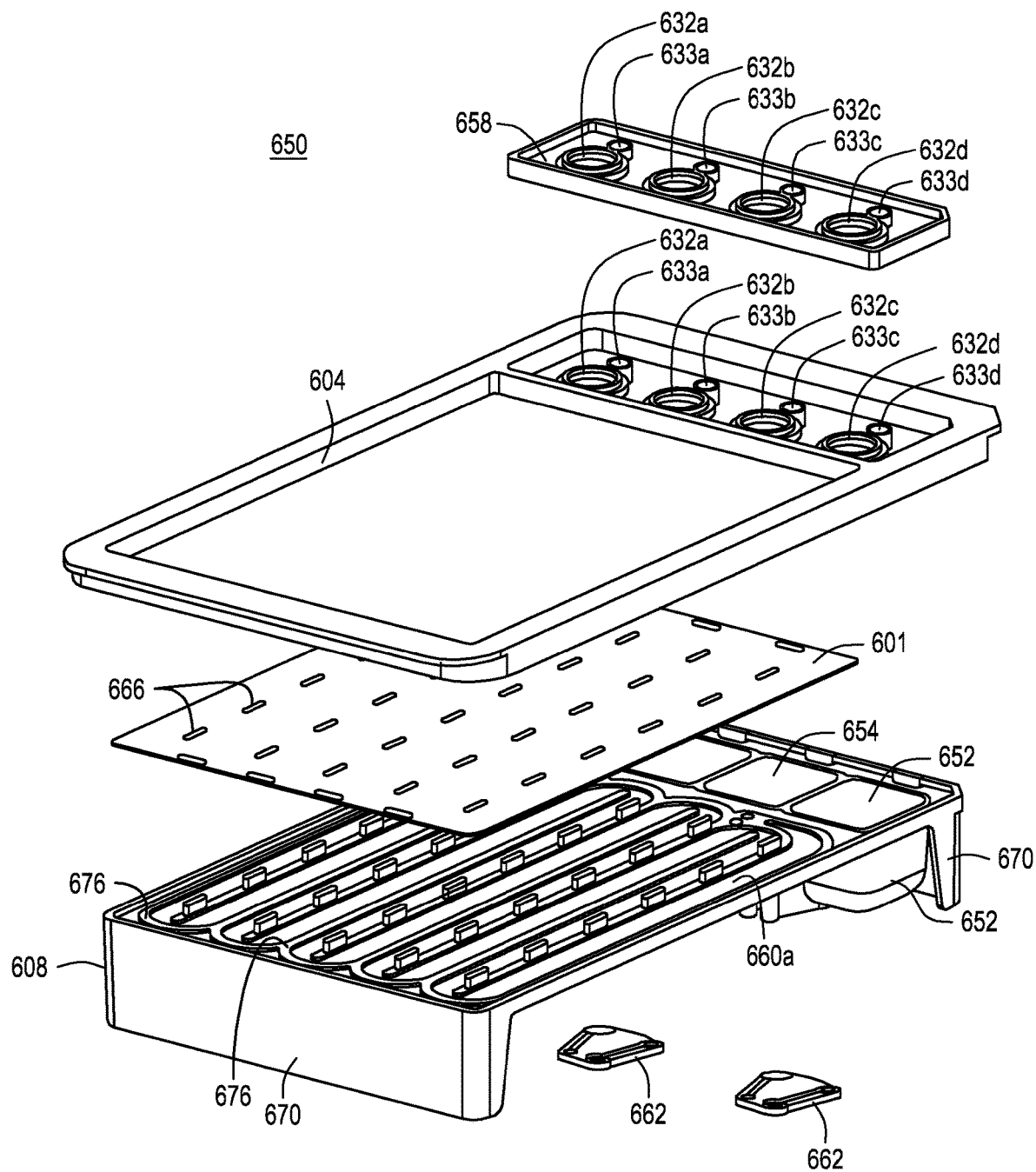
FIGS. 6B-6D depict an embodiment of a solid wall isolation incubation and normalization (SWIIN) module.

FIG. 6B depicts a solid wall device 6050 and a workflow for substantially singulating cells in microwells in a solid wall device. At the top left of the figure (i), there is depicted solid wall device 6050 with microwells 6052. A section 6054 of substrate 6050 is shown at (ii), also depicting microwells 6052. At (iii), a side cross-section of solid wall device 6050 is shown, and microwells 6052 have been loaded, where, in this embodiment, substantial Poisson loading has taken place; that is, some microwells 6057 have no cells, and some microwells 6076, 6078 have a few cells. In FIG. 6B, cells with active gRNAs are shown as solid circles, and cells with inactive gRNAs are shown as open circles. At (iv), workflow 6070 is illustrated where substrate 6050 having microwells 6052 shows three microwells 6076 with several cells all with active gRNAs, microwell 6057 with no cells, and two microwells 6078 with some cells having active gRNAs and some cells having inactive gRNAs. In step 6071, the cells in the microwells are allowed to double approximately 2-150 times to form clonal colonies (v), then editing takes place 6073.

After editing 6073, many cells in the colonies of cells that have been edited die as a result of the double-strand cuts caused by active editing and there is a lag in growth for the edited cells that do survive but must repair and recover following editing (microwells 6076), where cells that do not undergo editing thrive (microwells 6078) (vi). Thus, in microwells 6076 where only cells with active gRNAs reside (cells depicted by solid circles), most cells die off; however, in microwells 6078 containing cells with inactive gRNAs (cells depicted by open circles), cells continue to grow and are not impacted by active editing. The cells in each microwell (6076 and 6078) are allowed to grow to continue to establish colonies and normalize, where the colonies of edited cells in microwells 6076 catch up in size and/or cell number with the unedited cells in microwells 6078 that do not undergo editing (vii). Note that in this workflow 6070, the colonies of cells in the microwells are not clonal; that is, not all cells in a well arise from a single cell. Instead, the cell colonies in the well may be mixed colonies, arising in many wells from two to several different cells. Once the cell colonies are normalized, either pooling 6090 of all cells in the microwells can take place, in which case the cells are enriched for edited cells by eliminating the bias from non-editing cells and fitness effects from editing; alternatively, colony growth in the microwells is monitored after editing, and slow growing colonies (e.g., the cells in microwells 6076) are identified and selected 6091 (e.g., "cherry picked") resulting in even greater enrichment of edited cells.

Figure 6C:
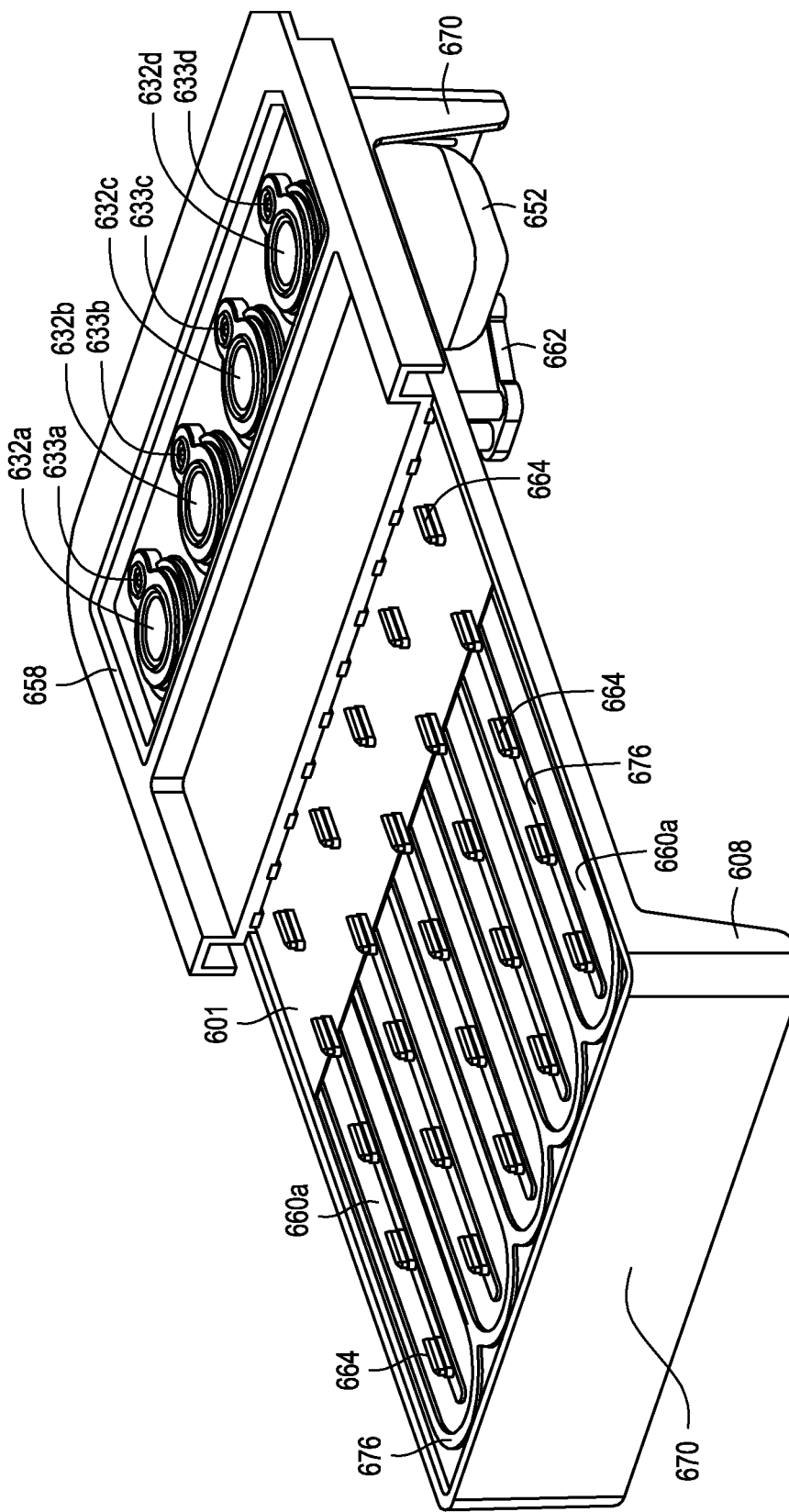

A module useful for performing the methods depicted in FIGS. 6A and 6B is a solid wall isolation, incubation, and normalization (SWIIN) module. FIG. 6C depicts an embodiment of a SWIIN module 650 from an exploded top perspective view. In SWIIN module 650 the retentate member is formed on the bottom of a top of a SWIIN module component and the permeate member is formed on the top of the bottom of a SWIIN module component.

The SWIIN module 650 in FIG. 6C comprises from the top down, a reservoir gasket or cover 658, a retentate member 604 (where a retentate flow channel cannot be seen in this FIG. 6C), a perforated member 601 swaged with a filter (filter not seen in FIG. 6C), a permeate member 608 comprising integrated reservoirs (permeate reservoirs 652 and retentate reservoirs 654), and two reservoir seals 662, which seal the bottom of permeate reservoirs 652 and retentate reservoirs 654. A permeate channel 660a can be seen disposed on the top of permeate member 608, defined by a raised portion 676 of serpentine channel 660a, and ultrasonic tabs 664 can be seen disposed on the top of permeate member 608 as well. The perforations that form the wells on perforated member 601 are not seen in this FIG. 6C; however, through-holes 666 to accommodate the ultrasonic tabs 664 are seen. In addition, supports 670 are disposed at either end of SWIIN module 650 to support SWIIN module 650 and to elevate permeate member 608 and retentate member 604 above reservoirs 652 and 654 to minimize bubbles or air entering the fluid path from the permeate reservoir to serpentine channel 660a or the fluid path from the retentate reservoir to serpentine channel 660b (neither fluid path is seen in this FIG. 6C).

In this FIG. 6C, it can be seen that the serpentine channel 660a that is disposed on the top of permeate member 608 traverses permeate member 608 for most of the length of permeate member 608 except for the portion of permeate member 608 that comprises permeate reservoirs 652 and retentate reservoirs 654 and for most of the width of permeate member 608. As used herein with respect to the distribution channels in the retentate member or permeate member, "most of the length" means about 95% of the length of the retentate member or permeate member, or about 90%, 85%, 80%, 75%, or 70% of the length of the retentate member or permeate member. As used herein with respect to the distribution channels in the retentate member or permeate member, "most of the width" means about 95% of the width of the retentate member or permeate member, or about 90%, 85%, 80%, 75%, or 70% of the width of the retentate member or permeate member.

In this embodiment of a SWIIN module, the perforated member includes through-holes to accommodate ultrasonic tabs disposed on the permeate member. Thus, in this embodiment the perforated member is fabricated from 316 stainless steel, and the perforations form the walls of microwells while a filter or membrane is used to form the bottom of the microwells. Typically, the perforations (microwells) are approximately 150 μm-200 μm in diameter, and the perforated member is approximately 125 μm deep, resulting in microwells having a volume of approximately 2.5 nl, with a total of approximately 200,000 microwells. The distance between the microwells is approximately 279 μm center-to-center. Though here the microwells have a volume of approximately 2.5 nl, the volume of the microwells may be from 1 to 25 nl, or preferably from 2 to 10 nl, and even more preferably from 2 to 4 nl. As for the filter or membrane, like the filter described previously, filters appropriate for use are solvent resistant, contamination free during filtration, and are able to retain the types and sizes of cells of interest. For example, in order to retain small cell types such as bacterial cells, pore sizes can be as low as 0.10 µm, however for other cell types (e.g., such as for mammalian cells), the pore sizes can be as high as 10.0 µm-20.0 µm or more. Indeed, the pore sizes useful in the cell concentration device/module include filters with sizes from 0.10 µm, 0.11 µm, 0.12 µm, 0.13 µm, 0.14 µm, 0.15 µm, 0.16 µm, 0.17 µm, 0.18 µm, 0.19 µm, 0.20 µm, 0.21 µm, 0.22 µm, 0.23 µm, 0.24 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.36 µm, 0.37 µm, 0.38 µm, 0.39 µm, 0.40 µm, 0.41 µm, 0.42 µm, 0.43 µm, 0.44 µm, 0.45 µm, 0.46 µm, 0.47 µm, 0.48 µm, 0.49 µm, 0.50 µm and larger. The filters may be fabricated from any suitable material including cellulose mixed ester (cellulose nitrate and acetate) (CME), polycarbonate (PC), polyvinylidene fluoride (PVDF), polyethersulfone (PES), polytetrafluoroethylene (PTFE), nylon, or glass fiber.

The cross-section configuration of the mated serpentine channel may be round, elliptical, oval, square, rectangular, trapezoidal, or irregular. If square, rectangular, or another shape with generally straight sides, the cross section may be from about 2 mm to 15 mm wide, or from 3 mm to 12 mm wide, or from 5 mm to 10 mm wide. If the cross section of the mated serpentine channel is generally round, oval or elliptical, the radius of the channel may be from about 3 mm to 20 mm in hydraulic radius, or from 5 mm to 15 mm in hydraulic radius, or from 8 mm to 12 mm in hydraulic radius.

Serpentine channels 660a and 660b can have approximately the same volume or a different volume. For example, each "side" or portion 660a, 660b of the serpentine channel may have a volume of, e.g., 2 mL, or serpentine channel 660a of permeate member 608 may have a volume of 2 mL, and the serpentine channel 660b of retentate member 604 may have a volume of, e.g., 3 mL. The volume of fluid in the serpentine channel may range from about 2 mL to about 80 mL, or about 4 mL to 60 mL, or from 5 mL to 40 mL, or from 6 mL to 20 mL (note these volumes apply to a SWIIN module comprising a, e.g., 50-500K perforation member). The volume of the reservoirs may range from 5 mL to 50 mL, or from 7 mL to 40 mL, or from 8 mL to 30 mL or from 10 mL to 20 mL, and the volumes of all reservoirs may be the same or the volumes of the reservoirs may differ (e.g., the volume of the permeate reservoirs is greater than that of the retentate reservoirs).

The serpentine channel portions 660a and 660b of the permeate member 608 and retentate member 604, respectively, are approximately 200 mm long, 130 mm wide, and 4 mm thick, though in other embodiments, the retentate and permeate members can be from 75 mm to 400 mm in length, or from 100 mm to 300 mm in length, or from 150 mm to 250 mm in length; from 50 mm to 250 mm in width, or from 75 mm to 200 mm in width, or from 100 mm to 150 mm in width; and from 2 mm to 15 mm in thickness, or from 4 mm to 10 mm in thickness, or from 5 mm to 8 mm in thickness. Embodiments the retentate (and permeate) members may be fabricated from PMMA (poly(methyl methacrylate) or other materials may be used, including polycarbonate, cyclic olefin co-polymer (COC), glass, polyvinyl chloride, polyethylene, polyamide, polypropylene, polysulfone, polyurethane, and co-polymers of these and other polymers. Preferably at least the retentate member is fabricated from a transparent material so that the cells can be visualized (see, e.g., FIG. 6F and the description thereof). For example, a video camera may be used to monitor cell growth by, e.g., density change measurements based on an image of an empty well, with phase contrast, or if, e.g., a chromogenic marker, such as a chromogenic protein, is used to add a distinguishable color to the cells. Chromogenic markers such as blitzen blue, dreidel teal, virginia violet, vixen purple, prancer purple, tinsel purple, maccabee purple, donner magenta, cupid pink, seraphina pink, scrooge orange, and leor orange (the Chromogenic Protein Paintbox, all available from ATUM (Newark, Calif.)) obviate the need to use fluorescence, although fluorescent cell markers, fluorescent proteins, and chemiluminescent cell markers may also be used.

Because the retentate member preferably is transparent, colony growth in the SWIIN module can be monitored by automated devices such as those sold by JoVE (ScanLag™ system, Cambridge, Mass.) (also see Levin-Reisman, et al., Nature Methods, 7:737-39 (2010)). Cell growth for, e.g., mammalian cells may be monitored by, e.g., the growth monitor sold by IncuCyte (Ann Arbor, Mich.) (see also, Choudhry, PLos One, 11(2):e0148469 (2016)). Further, automated colony pickers may be employed, such as those sold by, e.g., TECAN (Pickolo™ system, Mannedorf, Switzerland); Hudson Inc. (RapidPick™, Springfield, N.J.); Molecular Devices (QPix 400™ system, San Jose, Calif.); and Singer Instruments (PIXL™ system, Somerset, UK).

Due to the heating and cooling of the SWIIN module, condensation may accumulate on the retentate member which may interfere with accurate visualization of the growing cell colonies. Condensation of the SWIIN module 650 may be controlled by, e.g., moving heated air over the top of (e.g., retentate member) of the SWIIN module 650, or by applying a transparent heated lid over at least the serpentine channel portion 660b of the retentate member 604. See, e.g., FIG. 6F and the description thereof infra.

In SWIIN module 650 cells and medium—at a dilution appropriate for Poisson or substantial Poisson distribution of the cells in the microwells of the perforated member—are flowed into serpentine channel 660b from ports in retentate member 604, and the cells settle in the microwells while the medium passes through the filter into serpentine channel 660a in permeate member 608. The cells are retained in the microwells of perforated member 601 as the cells cannot travel through filter 603. Appropriate medium may be introduced onto permeate member 608 through permeate ports 611. The medium flows upward through filter 603 to nourish the cells in the microwells (perforations) of perforated member 601. Additionally, buffer exchange can be effected by cycling medium through the retentate and permeate members. In operation, the cells are deposited into the microwells, are grown for an initial, e.g., 2-100 doublings, editing is induced by, e.g., raising the temperature of the SWIIN to 42° C. to induce a temperature inducible promoter or by removing growth medium from the permeate member and replacing the growth medium with a medium comprising a chemical component that induces an inducible promoter.

Once editing has taken place, the temperature of the SWIIN may be decreased, or the inducing medium may be removed and replaced with fresh medium lacking the chemical component thereby de-activating the inducible promoter. The cells then continue to grow in the SWIIN module 650 until the growth of the cell colonies in the microwells is normalized. For the normalization protocol, once the colonies are normalized, the colonies are flushed from the microwells by applying fluid or air pressure (or both) to the permeate member serpentine channel 660a and thus to filter 603 and pooled. Alternatively, if cherry picking is desired, the growth of the cell colonies in the microwells is monitored, and slow-growing colonies are directly selected; or, fast-growing colonies are eliminated.

Figure 6D:
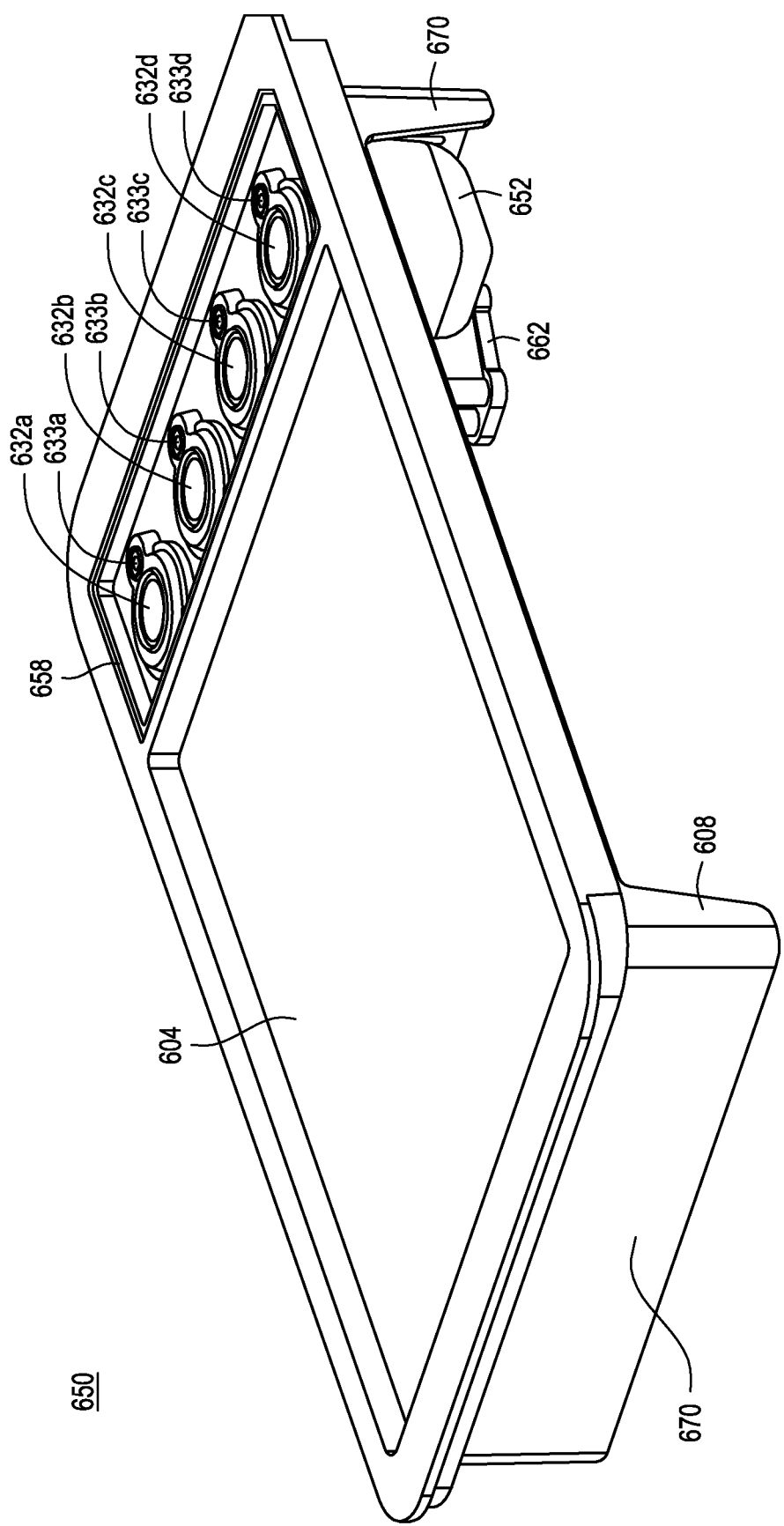

FIG. 6D is a top perspective view of a SWIIN module with the retentate and perforated members in partial cross section. In this FIG. 6D, it can be seen that serpentine channel 660a is disposed on the top of permeate member 608 is defined by raised portions 676 and traverses permeate member 608 for most of the length and width of permeate member 608 except for the portion of permeate member 608 that comprises the permeate and retentate reservoirs (note only one retentate reservoir 652 can be seen). Moving from left to right, reservoir gasket 658 is disposed upon the integrated reservoir cover 678 (cover not seen in this FIG. 6D) of retentate member 604. Gasket 658 comprises reservoir access apertures 632a, 632b, 632c, and 632d, as well as pneumatic ports 633a, 633b, 633c and 633d. Also at the far left end is support 670. Disposed under permeate reservoir 652 can be seen one of two reservoir seals 662. In addition to the retentate member being in cross section, the perforated member 601 and filter 603 (filter 603 is not seen in this FIG. 6D) are in cross section. Note that there are a number of ultrasonic tabs 664 disposed at the right end of SWIIN module 650 and on raised portion 676 which defines the channel turns of serpentine channel 660a, including ultrasonic tabs 664 extending through through-holes 666 of perforated member 601. There is also a support 670 at the end distal reservoirs 652, 654 of permeate member 608.

Figure 6E:
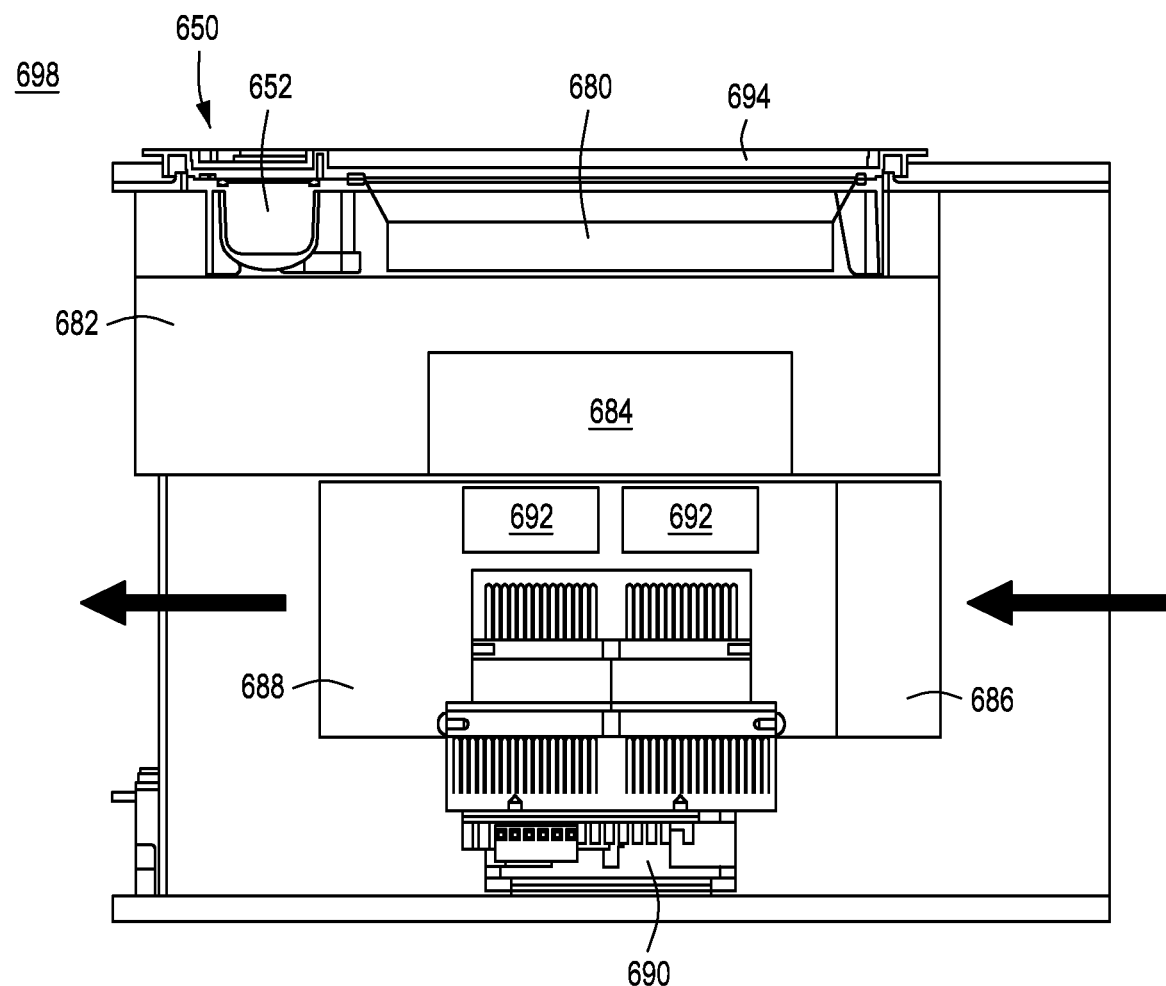
FIG. 6E depicts the embodiment of the SWIIN module in FIGS. 6B-6D further comprising a heater and a heated cover.

FIG. 6E is a side perspective view of an assembled SWIIN module 650, including, from right to left, reservoir gasket 658 disposed upon integrated reservoir cover 678 (not seen) of retentate member 604. Gasket 658 may be fabricated from rubber, silicone, nitrile rubber, polytetrafluoroethylene, a plastic polymer such as polychlorotrifluoroethylene, or other flexible, compressible material. Gasket 658 comprises reservoir access apertures 632a, 632b, 632c, and 632d, as well as pneumatic ports 633a, 633b, 633c and 633d. Also at the far-left end is support 670 of permeate member 608. In addition, permeate reservoir 652 can be seen, as well as one reservoir seal 662. At the far-right end is a second support 670.

Imaging of cell colonies growing in the wells of the SWIIN is desired in most implementations for, e.g., monitoring both cell growth and device performance and imaging is necessary for cherry-picking implementations. Real-time monitoring of cell growth in the SWIIN requires backlighting, retentate plate (top plate) condensation management and a system-level approach to temperature control, air flow, and thermal management. In some implementations, imaging employs a camera or CCD device with sufficient resolution to be able to image individual wells. For example, in some configurations a camera with a 9-pixel pitch is used (that is, there are 9 pixels center-to-center for each well). Processing the images may, in some implementations, utilize reading the images in grayscale, rating each pixel from low to high, where wells with no cells will be brightest (due to full or nearly-full light transmission from the backlight) and wells with cells will be dim (due to cells blocking light transmission from the backlight). After processing the images, thresholding is performed to determine which pixels will be called "bright" or "dim", spot finding is performed to find bright pixels and arrange them into blocks, and then the spots are arranged on a hexagonal grid of pixels that correspond to the spots. Once arranged, the measure of intensity of each well is extracted, by, e.g., looking at one or more pixels in the middle of the spot, looking at several to many pixels at random or pre-set positions, or averaging X number of pixels in the spot. In addition, background intensity may be subtracted. Thresholding is again used to call each well positive (e.g., containing cells) or negative (e.g., no cells in the well). The imaging information may be used in several ways, including taking images at time points for monitoring cell growth. Monitoring cell growth can be used to, e.g., remove the "muffin tops" of fast-growing cells followed by removal of all cells or removal of cells in "rounds" as described above, or recover cells from specific wells (e.g., slow-growing cell colonies); alternatively, wells containing fast-growing cells can be identified and areas of UV light covering the fast-growing cell colonies can be projected (or rastered with shutters) onto the SWIIN to irradiate or inhibit growth of those cells. Imaging may also be used to assure proper fluid flow in the serpentine channel 660.

FIG. 6F depicts the embodiment of the SWIIN module in FIGS. 6A-6E further comprising a heat management system including a heater and a heated cover. The heater cover facilitates the condensation management that is required for imaging. Assembly 698 comprises a SWIIN module 650 seen lengthwise in cross section, where one permeate reservoir 652 is seen. Disposed immediately upon SWIIN module 650 is cover 694 and disposed immediately below SWIIN module 650 is backlight 680, which allows for imaging. Beneath and adjacent to the backlight and SWIIN module is insulation 682, which is disposed over a heatsink 684. In this FIG. 6F, the fins of the heatsink would be in-out of the page. In addition there is also axial fan 686 and heat sink 688, as well as two thermoelectric coolers 692, and a controller 690 to control the pneumatics, thermoelectric coolers, fan, solenoid valves, etc. The arrows denote cool air coming into the unit and hot air being removed from the unit. It should be noted that control of heating allows for growth of many different types of cells (prokaryotic and eukaryotic) as well as strains of cells that are, e.g., temperature sensitive, etc., and allows use of temperature-sensitive promoters. Temperature control allows for protocols to be adjusted to account for differences in transformation efficiency, cell growth and viability. For more details regarding solid wall isolation incubation and normalization devices see U.S. Pat. No. 10,533,152, issued 14 Jan. 2020; and U.S. Pat. No. 10,550,363, issued 4 Feb. 2020; and U.S. Ser. No. 16/597,826, filed 19 Oct. 2019; Ser. No. 16/597,831, filed 9 Oct. 2019; and Ser. No. 16/693,630, filed 25 Nov. 2019. For alternative isolation, incubation and normalization modules, see U.S. Pat. No. 10,532,324, issued 14 Jan. 2020; and U.S. Ser. No. 16/687,640, filed 18 Nov. 2019; and Ser. No. 16/686,066, filed 15 Nov. 2019.

Use of the Automated Multi-Module Cell Processing Instrument

Figure 7:
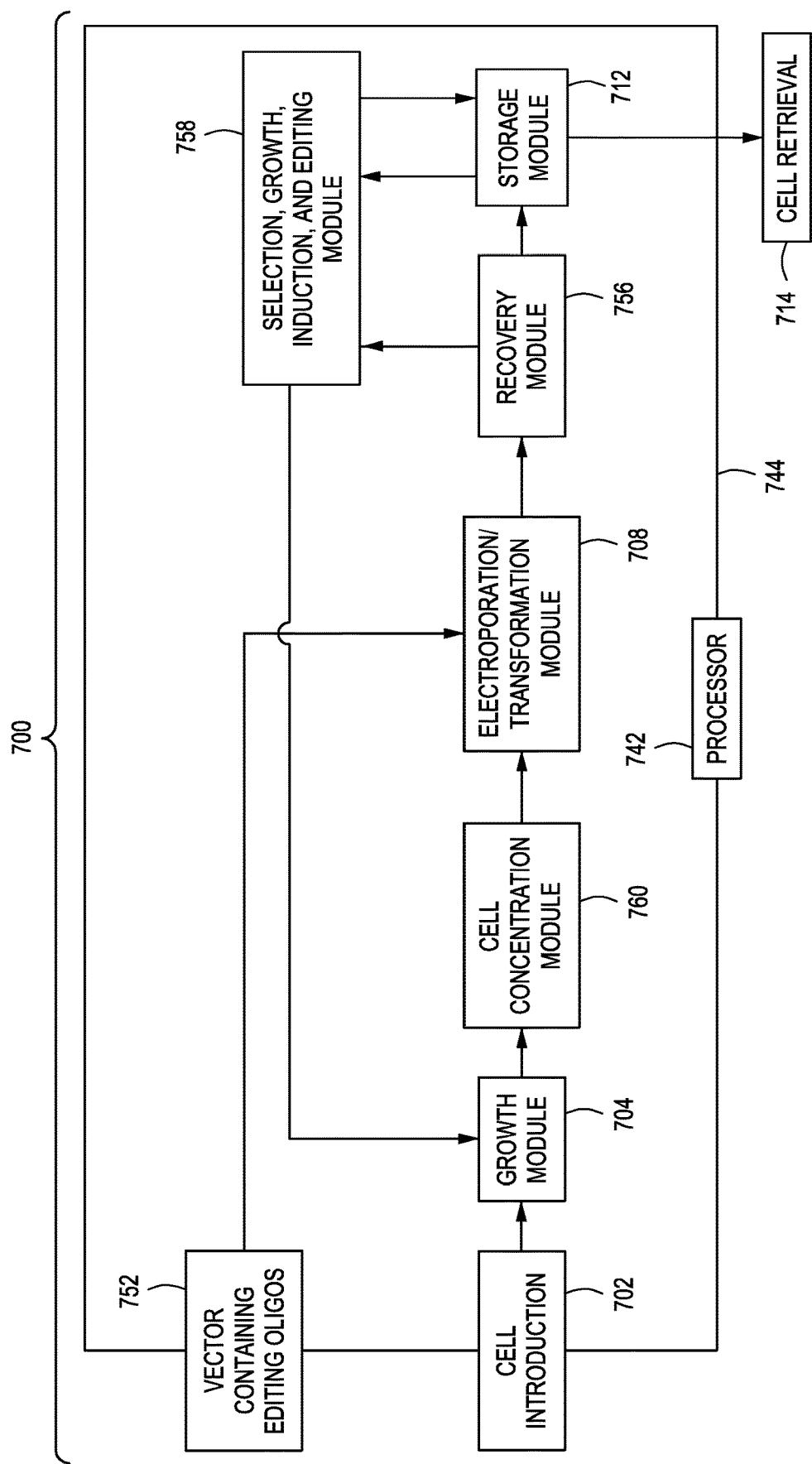
FIG. 7 is a simplified block diagram of an embodiment of an exemplary automated multi-module cell processing instrument comprising a solid wall singulation/growth/editing/normalization module, in this case, used for recursive editing.

One embodiment of an automated multi-module cell processing instrument capable of performing the methods described herein is shown in FIG. 7. FIG. 7 illustrates another embodiment of a multi-module cell processing instrument 700. This embodiment depicts an exemplary system that performs recursive gene editing on a cell population. The cell processing instrument 700 may include a housing 744, a reservoir for storing cells to be transformed or transfected 702, and a cell growth module (comprising, e.g., a rotating growth vial) 704. The cells to be transformed are transferred from a reservoir to the cell growth module 704 to be cultured until the cells hit a target OD. Once the cells hit the target OD, the growth module may cool or freeze the cells for later processing or transfer the cells to a cell concentration module 760 where the cells are subjected to buffer exchange and rendered electrocompetent, and the volume of the cells may be reduced substantially. Once the cells have been concentrated to an appropriate volume, the cells are transferred to electroporation device or module 708. In addition to the reservoir for storing cells, the multi-module cell processing instrument 700 includes a reservoir for storing the vector pre-assembled with editing oligonucleotide cassettes 752. The pre-assembled nucleic acid vectors are transferred to the electroporation device 708, which already contains the cell culture grown to a target OD. In the electroporation device 708, the nucleic acids are electroporated into the cells. Following electroporation, the cells are transferred into an optional recovery (and optionally, dilution) module 756, where the cells are allowed to recover briefly post-transformation.

After recovery, the cells may be transferred to a storage module 712, where the cells can be stored at, e.g., 4° C. for later processing, or the cells may be diluted and transferred to a selection/growth/induction/editing module 758. The cells are allowed to grow and editing is then induced by providing conditions (e.g., temperature, addition of an inducing or repressing chemical) to induce editing. Note that the selection/growth/induction and editing modules may be the same module or device, where all processes are performed in, e.g., a solid wall singulation device, or selection and/or dilution may take place in a separate vessel before the cells are transferred to an induction/editing module. As an alternative to singulation in, e.g., a solid wall device, the transformed cells may be grown in—and editing can be induced in—bulk liquid (see, e.g., U.S. Ser. No. 16/545,097, filed 20 Aug. 2019. Once the putatively-edited cells are pooled, they may be subjected to another round of editing, beginning with growth, cell concentration and treatment to render electrocompetent, and transformation by yet another donor nucleic acid in another editing cassette via the electroporation device/module 708.

In electroporation device 708, the cells selected from the first round of editing are transformed by a second set of editing oligos (or other type of oligos) and the cycle is repeated until the cells have been transformed and edited by a desired number of, e.g., editing cassettes. The multi-module cell processing instrument 700 exemplified in FIG. 7 is controlled by a processor 742 configured to operate the instrument based on user input or is controlled by one or more scripts including at least one script associated with the reagent cartridge. The processor 742 may control the timing, duration, and temperature of various processes, the dispensing of reagents, and other operations of the various modules of the instrument 700. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 7, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries. In any recursive process, it is advantageous to "cure" the previous engine and editing vectors (or single engine+editing vector in a single vector system). "Curing" is a process in which one or more vectors used in the prior round of editing is eliminated from the transformed cells. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine plasmid.

Figure 8:
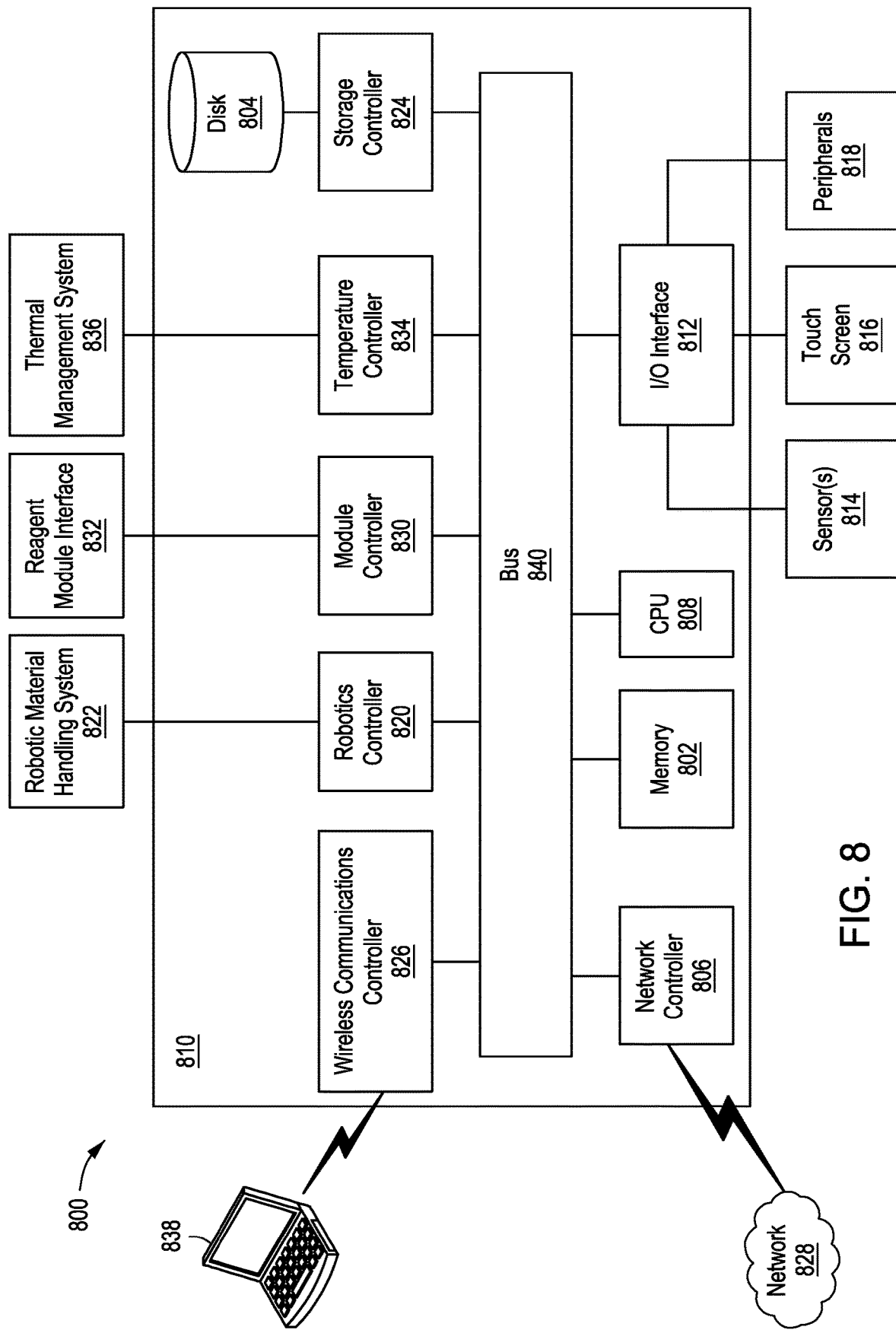
FIG. 8 is an example control system for use in an automated multi-module cell editing instrument.

The automated modules and reagent dispensing of the automated multi-module cell editing instruments are controlled by a processing system and processing environment, such as described with reference to FIG. 8. In FIG. 8, the processing system 810 includes a CPU 808 which performs a portion of the processes described above. For example, the CPU 808 may manage the processing stages of the method 100 of FIG. 1 and/or the workflow of FIG. 7. The process data and, scripts, instructions, and/or user settings may be stored in memory 802. These process data and, scripts, instructions, and/or user settings may also be stored on a storage medium disk 804 such as a portable storage medium (e.g., USB drive, optical disk drive, etc.) or may be stored remotely. For example, the process data and, scripts, instructions, and/or user settings may be stored in a location accessible to the processing system 810 via a network 828. Further, the claimed advancements are not limited by the form of the computer-readable media on which the instructions of the inventive process are stored. For example, the instructions may be stored in FLASH memory, RAM, ROM, or any other information processing device with which the processing system 810 communicates, such as a server, computer, smart phone, or other hand-held computing device.

Further, components of the claimed advancements may be provided as a utility application, background daemon, or component of an operating system, or combination thereof, executing in conjunction with CPU 808 and an operating system such as with other computing systems known to those skilled in the art.

CPU 808 may be an ARM processor, system-on-a-chip (SOC), microprocessor, microcontroller, digital signal processor (DSP), or may be other processor types that would be recognized by one of ordinary skill in the art. Further, CPU 808 may be implemented as multiple processors cooperatively working in parallel to perform the instructions of the inventive processes described above.

The processing system 810 is part of a processing environment 800. The processing system 810 in FIG. 8 also includes a network controller 806 for interfacing with the network 828 to access additional elements within the processing environment 800. As can be appreciated, the network 828 can be a public network, such as the Internet, or a private network such as an LAN or WAN network, or any combination thereof and can also include PSTN or ISDN sub-networks. The network 828 can be wireless such as a cellular network including EDGE, 3G and 4G wireless cellular systems. The wireless network can also be Wi-Fi, Bluetooth, or any other wireless form of communication that is known.

The processing system 810 further includes a general purpose I/O interface 812 interfacing with a user interface (e.g., touch screen) 816, one or more sensors 814, and one or more peripheral devices 818. The peripheral I/O devices 818 may include, in some examples, a video recording system, an audio recording system, microphone, external storage devices, and/or external speaker systems. The one or more sensors 814 may include one or more of a gyroscope, an accelerometer, a gravity sensor, a linear accelerometer, a global positioning system, a bar code scanner, a QR code scanner, an RFID scanner, a temperature monitor, and a lighting system or lighting element.

The general purpose storage controller 824 connects the storage medium disk 1804 with communication bus 840, such as a parallel bus or a serial bus such as a Universal Serial Bus (USB), or similar, for interconnecting all of the components of the processing system. A description of the general features and functionality of the storage controller 824, network controller 806, and general purpose I/O interface 812 is omitted herein for brevity as these features are known.

The processing system 810, in some embodiments, includes one or more onboard and/or peripheral sensors 814. The sensors 814, for example, can be incorporated directly into the internal electronics and/or a housing of the automated multi-module processing instrument. A portion of the sensors 814 can be in direct physical contact with the I/O interface 812, e.g., via a wire; or in wireless contact e.g., via a Bluetooth, Wi-Fi or NFC connection. For example, a wireless communications controller 826 may enable communications between one or more wireless sensors 1814 and the I/O interface 812. Furthermore, one or more sensors 814 may be in indirect contact e.g., via intermediary servers or storage devices that are based in the network 828; or in (wired, wireless or indirect) contact with a signal accumulator somewhere within the automated multi-module cell editing instrument, which in turn is in (wired or wireless or indirect) contact with the I/O interface 812.

A group of sensors 814 communicating with the I/O interface 812 may be used in combination to gather a given signal type from multiple places in order to generate a more complete map of signals. One or more sensors 814 communicating with the I/O interface 812 can be used as a comparator or verification element, for example to filter, cancel, or reject other signals.

In some embodiments, the processing environment 800 includes a computing device 838 communicating with the processing system 810 via the wireless communications controller 826. For example, the wireless communications controller 826 may enable the exchange of email messages, text messages, and/or software application alerts designated to a smart phone or other personal computing device of a user.

The processing environment 800, in some implementations, includes a robotic material handling system 822. The processing system 810 may include a robotics controller 820 for issuing control signals to actuate elements of the robotic material handling system, such as manipulating a position of a gantry, lowering or raising a sipper or pipettor element, and/or actuating pumps and valves to cause liquid transfer between a sipper/pipettor and various vessels (e.g., chambers, vials, etc.) in the automated multi-module cell editing instrument. The robotics controller 820, in some examples, may include a hardware driver, firmware element, and/or one or more algorithms or software packages for interfacing the processing system 810 with the robotics material handling system 822.

In some implementations, the processing environment 810 includes one or more module interfaces 832, such as, in some examples, one or more sensor interfaces, power control interfaces, valve and pump interfaces, and/or actuator interfaces for activating and controlling processing of each module of the automated multi-module processing system. For example, the module interfaces 832 may include an actuator interface for the drive motor of rotating cell growth device 200 (FIG. 3A) and a sensor interface for a detector board that senses optical density of cell growth within the rotating growth vial. A module controller 830, in some embodiments, is configured to interface with the module interfaces 832. The module controller 830 may include one or many controllers (e.g., possibly one controller per module, although some modules may share a single controller). The module controller 830, in some examples, may include a hardware driver, firmware element, and/or one or more algorithms or software packages for interfacing the processing system 810 with the module interfaces 832.

The processing environment 810, in some implementations, includes a thermal management system 836 for controlling climate conditions within the housing of the automated multi-module processing system. The thermal management system 836 may additional control climate conditions within one or more modules of the automated multi-module cell editing instrument. The processing system 810, in some embodiments, includes a temperature controller 834 for interfacing with the thermal management system 836. The temperature controller 834, in some examples, may include a hardware driver, firmware element, and/or one or more algorithms or software packages for interfacing the processing system 810 with the thermal management system 836.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example #1

Cloning Target Polynucleotide The FtsY gene from *Bacillus subtilis* was amplified by PCR from a source plasmid template pJet1.2 FtsY (Addgene catalog #117130) and cloned into the polylinker sequence of the pDG1662, a *Bacillus subtilis* integration vector, by restriction enzyme digest and conventional sticky end cloning. pDG1662 contains the cat gene which confers resistance to chloramphenicol; the bla gene which confers ampicillin resistance for selection in *E. coli*; the spc gene which confers spectinomycin resistance for selection in *E. coli* or *B. subtilis*; two regions of homology to the *B. subtilis* amyE locus, upstream and downstream, respectively, which mediate ectopic integration of the cloned target polynucleotide into the *B. subtilis* genome as a double-crossover recombination at the amyE locus; and a replication origin active in *E. coli* but not in *B. subtilis*, to guarantee that only *B. subtilis* clones with successful chromosomal integrations propagate after transformation and selection.

Ligation of the amplified target nucleotide was performed in NEB 5-alpha competent *E. coli* cells according to standard conditions and transformants were grown on ampicillin plates (100 µg/mL). Positive clones were isolated and successful insertion of the FtsY gene was confirmed by diagnostic restriction enzyme digest and colony PCR across the insert junctions. The resulting *E. coli* strain carrying the FtsY shuttle vector was designated "FtsY shuttle vector" cells.

Editing Cassette and Backbone Amplification and Assembly

Editing Cassette Preparation: 5 nM of oligonucleotides directed toward saturation mutagenesis of the FtsY gene synthesized on a chip were amplified using Q5 polymerase in 50 µL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 30 µL SPRI mix was added to the 50 µL PCR reactions and incubated for 2 minutes. The tubes were subjected to a magnetic field for 2 minutes, the liquid was removed, and the beads were washed 2x with 80% ethanol, allowing 1 minute between washes. After the final wash, the beads were allowed to dry for 2 minutes, 50 µL 0.5xTE pH 8.0 was added to the tubes, and the beads were vortexed to mix. The slurry was incubated at room temperature for 2 minutes, then subjected to the magnetic field for 2 minutes. The eluate was removed, and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation: A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 µL ddH$_2$O and quantified before Gibson Assembly®.

Isothermal Assembly: 150 ng backbone DNA was combined with 100 ng cassette DNA. An equal volume of 2x Master Mix was added, and the reaction was incubated for 45 minutes at 50° C. After assembly, the assembled backbone and cassettes were subjected to SPRI cleanup, as described above.

Transformation with Engine Vector: 1 µL of the engine vector DNA (comprising a coding sequence for MAD7 nuclease under the control of the pL inducible promoter, a chloramphenicol resistance gene, and the λ Red recombineering system) was added to 50 µL "FtsY shuttle vector" *E. coli* cells. The transformed cells were plated on LB plates with 25 µg/mL chloramphenicol (chlor) and 100 µg/mL carbenicillin and incubated overnight to accumulate clonal isolates. The next day, a colony was picked, grown overnight in LB+25 µg/mL chlor+100 µg/mL carb, and glycerol stocks were prepared from the saturated overnight culture by adding 500 µL 50% glycerol to 1000 µL culture. The stocks of "FtsY shuttle vector" *E. coli* cells comprising the engine vector were frozen at −80° C.

Transformation with Editing Library: The assembled editing vector and electrocompetent "FtsY shuttle vector" *E. coli* cells (that carry both the target polynucleotide on a shuttle vector and the engine vector) were transferred into a transformation module for electroporation. The transformation module comprised an ADP-EPC cuvette. See, e.g., U.S. Pat No. 62/551,069. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing kanamycin. Carbenicillin and chloramphenicol were added to the medium after 1 hour, and the cells were allowed to recover for another 2 hours. After recovery, the cells were held at 4° C. until recovered by the user. An aliquot of cells was plated on LB agar supplemented with chloramphenicol, carbenicillin, and kanamycin.

Hundreds of colonies were picked on a high-throughput robotic colony-picking apparatus, grown in LB+ampicillin (100 µg/mL) in 96-well format, and edited shuttle vector DNA was prepared by 96-well format miniprep. Isolated shuttle vector DNA was sequenced to identify edits.

For identified mutations, the integrating segment of the edited shuttle vector was liberated from the pDG1662 backbone by restriction enzyme digestion of approximately 1 µg of shuttle vector DNA with AatII and BstXI. Restriction enzymes were heat-inactivated prior to *B. subtilis* transformation.

A single colony of *B. subtilis* was inoculated into 4.5 mL of Medium A (81 mL sterile water; 10 mL 10x Medium A base; 10x *Bacillus* salts; see Yasbin et al. Transformation and Transfection in Lysogenic Strains of *Bacillus subtilis*: Evidence for Selective Induction of Prophage in Competent Cells. Journal of Bacteriology. 121:1 296-304. 1975.) and adjusted with additional inoculants to reach an OD$_{650}$ of 0.1-0.2. Culture was incubated at 37° C. with vigorous shaking from 60-90 minutes and OD$_{650}$ was recorded every 20 minutes. Culture was grown for 90 minutes after the cessation of logarithmic growth. 0.05 mL of this culture was transferred into 0.45 mL of pre-warmed Medium B, one tube for each transformation, incubated at 37° C. with vigorous shaking for 90 minutes, after which cultures were highly competent. 1 µg of digested edited shuttle vector DNA was added to each transformation tube, one for each edit, and incubated at 37° C. with shaking for 30 minutes. Aliquots of transformed *B. subtilis* cells were plated onto agar plates containing chloramphenicol (5 µg/mL).

Individual *B. subtilis* transformants carrying the integrated edited shuttle vector were picked, propagated in culture, and impact of edits of the FtsY gene were evaluated in a high-throughput functional assay.

Example #2

Cloning human genetic locus into TAR shuttle vector in yeast: *Saccharomyces cerevisiae* strain VL6-48 (MAT alpha, his3-Δ 200, trp1-Δ 1, ura3-Δ 1, lys2, ade2-101, met14) that has HIS3, TRP1, and URA3 deleted was used as a host for TAR cloning of human gene LMNA (ATCC Number MYA-3666™).

The TAR cloning vector pVC-604 (ATCC® MBA-212™) contains a yeast selectable marker (HIS3) and a yeast centromeric sequence (CEN6). Before use, the TAR vector was "activated" by insertion of the targeting sequences (hooks) specific for LMNA (5' and 3' ends of the gene) into the polylinker. Such shuttle vector should be constructed before TAR cloning experiments. Hooks were unique sequences; no repeated sequences were present in the hooks. The uniqueness of hooks was checked by BLASTing against the human genome. The minimal size of the targeting hooks was 60 bp. Before TAR cloning, the vector was linearized by cutting between the targeting hooks with a restriction enzyme. Concentration of the linearized TAR vector was 0.5-1 µg/µl. Vector DNA was isolated by DNA Maxi kit (Qiagen).

A yeast-bacteria-mammalian cell shuttle vector for retrofitting circular YAC/TAR isolates into a BAC form ("retrofitting vector") contained a 3' HPRT-loxP-eGFP cassette, allowing gene loading into a unique loxP site within the HAC-based shuttle vector. An F' factor origin of replication allows YAC propagation as a single copy BAC molecule.

The Cre recombinase expression vector was derived from the pCpGfree-vitroHLacZ plasmid (InvivoGen). It contained a hygromycin resistance gene that allows selection of the plasmid in both bacteria and vertebrate cells. The optimized Cre gene is under the EF1 promoter and flanked by Matrix Attachment Region (MAR) elements. The MAR elements together with the absence of CpG sites in promoter or vector sequences greatly improve the transcription efficiency of the Cre gene. The iCre plasmid also contains a conditional R6K bacterial origin, which requires a pir+ expressing *E. coli* strain to propagate.

Highly competent yeast spheroplasts were prepared by pelleting an overnight culture of *Saccharomyces cerevisiae* strain VL6-48, resuspending in 20 mL of 1 M Sorbitol, pelleting again, resuspending in 20 mL of SPE solution (1 M Sorbitol, 10 mM Na$_2$ EDTA, 0.01 M Na phosphate, pH 7.5), adding 20 µL zymolyase solution (10 mg/ml of zymolyase 20T in 20% glycerol), 40 µL of ME (14.3 M beta-mercaptoethanol), mixing, and incubating at 30° C. for 20 minutes. Spheroplasts were centrifuged for 10 min at 570×g at 5° C. Supernatant was decanted, cells gently resuspended in 50 ml of 1.0 M Sorbitol, and the spheroplasts were pelleted again by centrifugation for 10 min at 300-600×g at 5° C. The 50 ml of 1 M Sorbitol wash was repeated one more time, and the final pellet was gently resuspended in 2.0 ml of STC solution (1 M Sorbitol, 10 mM CaCl$_2$, 10 mM Tris-HCl, pH 7.5).

200 µL of competent spheroplast suspension was mixed gently with 1-2 µg of human genomic DNA and 1.0 µg of linearized shuttle vector pVC-604 and incubated for 10 minutes at room temperature. 800 µL of PEG 8000 solution was added and gently mixed by inverting and incubated at room temperature for 10 minutes. Spheroplasts were pelleted by centrifugation for 5 min at 300-500×g at 5° C. Supernatant was removed and spheroplasts were gently resuspended in 800 µl of SOS solution (1 M Sorbitol, 6.5 mM CaCl$_2$), 0.25% yeast extract, 0.5% Bacto Peptone) by pipetting. Spheroplasts were incubated for 40 minutes at 30° C. without shaking.

Spheroplasts were transferred to a 15-ml Falcon conical tube containing 7.0 ml of melted TOP agar-His (1 M Sorbitol, 2% D-glucose, 0.17% Yeast Nitrogen Base, 0.5% (NH$_4$)$_2$SO$_4$, 3% agar containing the following supplements: 0.006% adenine sulfate, 0.006% uracil, 0.005% L-arginine.HCl, 0.008% L-aspartic acid, 0.01% L-GLUTAMIC acid, 0.005% L-isoleucine, 0.01% L-leucine, 0.012% L-lysine.HCl, 0.002% L-methionine, 0.005% L-phenylalanine, 0.0375% L-serine, 0.01% L-threonine, 0.005% L-tryptophan, 0.005% L-tyrosine, 0.015% L-valine equilibrated at 50° C.) by pipetting, gently mixed, and agar mix was quickly poured onto a SORB-His plate (1 M Sorbitol, 2% D-glucose, 0.17% Yeast Nitrogen Base 0.5% (NH$_4$)$_2$SO$_4$, 2% agar supplemented as described above) with selective medium containing 1 M Sorbitol. Plates were incubated at 30° C. for 5-7 days until transformants became visible.

Positive clones were identified and confirmed by isolating shuttle vector DNA by standard techniques, amplifying across the insert junctions with PCR primers designed complementary to the shuttle vector sequence flanking the target polynucleotide insert, and sequencing the junctions.

Editing Target Polynucleotide in Yeast: A positive clone carrying the YAC shuttle vector described above was rendered electrocompetent and co-transformed with a library of editing cassettes directed toward saturation mutagenesis of the target polynucleotide and an editing vector backbone by electroporation. In vivo recombination after transformation results in a complete editing vector carrying the components necessary for nucleic acid-guided nuclease editing described herein. Growth on selective medium allows for propagation only of cells that carry a complete editing vector and have successfully received an edit of the target polynucleotide.

Retrofitting Edited YAC Shuttle Vector Into BAC: 5 ml of SD-His synthetic liquid medium without histidine was inoculated with one individual colony containing the edited TAR/YAC shuttle vector and grown overnight at 30° C. with vigorous shaking. The culture was transferred into 50-mL liquid YPD and grown for an additional 4-5 hours at 30° C. with vigorous shaking. The culture was pelleted by centrifugation for 5 minutes at 1,000×g at 5° C. in a 50-mL Falcon tube, and supernatant was discarded. Pellet was resuspended in 10 mL of sterile water by vortexing, transferred into an Eppendorf tube, and pelleted again. Cells were resuspended in 10 mL of LiAc solution (100 mM lithium acetate, 10 mM Tris-HCl, 0.1 mM EDTA, pH 7.5), incubated at 30° C. for 1 hour with slow shaking, and collected by centrifugation. Supernatant was discarded and cells were resuspended in 100 µL LiAc solution by pipetting. 1 µg of BamHI linearized "retrofitting vector" DNA and 5 µL of carrier salmon DNA (10 mg/ml sonicated salmon sperm DNA (Stratagene) denatured by boiling for 10 min every time before the experiment) were added to cells and mixed well. 0.45 mL of fresh PEG 4000 solution was added to cells, mixed by vortexing, and incubated for 1 hour at 30° C. Cells were heat-shocked in a 42° C. heating block for 15 minutes. Cells were rinsed with sterile water, collected by centrifugation at high speed for 1 minutes, and supernatant was discarded. Cells were rinsed one more time with sterile water, supernatant was discarded, cells were resuspended in sterile water and the suspension was plated on SD-Ura plates. Plates were incubated for 2-3 days at 30° C. until Ura$^+$ colonies were observed. Ura$^+$ transformants now contained the retrofitted YAC/BAC shuttle vector carrying the edited target polynucleotide.

Transferring Retrofitted Shuttle Vector from Yeast to *E. coli*: Two to three His$^+$Ura$^+$ transformants carrying the edited shuttle vector were inoculated separately in 5 ml of YPD medium each in 50-ml Falcon conical tubes and grown overnight at 30° C. with a vigorous shaking. Cells were pelleted and resuspended in 100 µl EDTA mix (0.05 M EDTA, 0.01 M Tris-HCl, pH 7.5) and transferred to 1.5 mL Eppendorf tubes. 100 µl of zymolyase solution was added, mixed by vortexing, and incubated for 30 minutes at 37° C. Cell suspension and equal volumes low melting point agarose (LMP: 1% of agarose gel prepared in 0.125 M EDTA, pH 7.5) were equilibrated in a heat block at 42° C. Agarose plugs of the cell suspension were made by mixing cell suspension and LMP 1:1 and using pipette tips as molds. Solidified agarose plugs were suspended in LET solution (0.5 M EDTA, 0.01 M Tris-HCl, pH 7.5) in Eppendorf tubes and incubated for 1 hour at 37° C. LET solution was removed, plugs were covered in NDS cell lysis buffer (0.39 M EDTA, 0.01 M Tris-HCl, pH 7.5, 1% N-lauroyl sarcosine, 2 mg/ml proteinase K), and incubated for 1 hour at 55° C. NDS buffer was removed and plugs were washed three times with EDTA mix. To electroporate the edited YAC/BAC shuttle vector into *E. coli*, the plugs were melted at 68° C. for 15 min, cooled to 42° C. for 10 min, treated with 1.5 units of β-agarase for 1 h at 42° C., and chilled on ice for 10 minutes. The plugs were diluted twofold with sterile water, and 1 µl of the mixture was used to electroporate 20 µl of electrocompetent *E. coli* cells. After electroporation cells were recovered in SOC medium for 1 hour at 37° C. Cells were plated on LB-Chlor plates and incubated at 37° C. overnight.

Insertion of Edited Target Nucleotide from Shuttle Vector into HAC: To insert the edited target nucleotide into the HAC, the retrofitted YAC/BAC shuttle vector was co-transfected with a Cre-recombinase expression vector into a hprt-minus hamster CHO cells carrying the HAC and HPRT-plus colonies were selected on Hypoxanthine-Aminopterin-Thymidine (HAT) medium. YAC/BAC shuttle vector DNA was prepared by Large-Construct Kit (Qiagen) and Cre-recombinase expression plasmid by Spin Miniprep Kit (Qiagen), respectively. One day before transfection, CHO cells were plated in a six-well plate of 2 ml of growth medium (F12+10% FBS+1% PenStrep+8 µg/ml blasticidin). 20-30 µg of prepared YAC/BAC shuttle vector DNA and 1 µg of Cre-recombinase expression vector DNA were diluted in 100 µL Opti-MEM medium without serum. 10 µL of Lipofectamine 2000 was diluted in 90 µL of Opti-MEM. Diluted DNAs and diluted Lipofectaimine were combined for a total volume of 200 µL and incubated at room temperature for 20-30 minutes. At the same time CHO cells were washed in six-well plate one time by PBS, rinsed with 2 ml of Opti-MEM medium, aspirated and washed with 2 ml Opti-MEM medium again (three washes in total), and incubated at 37° C. for 20-30 minutes. After incubation cells the Opti-MEM wash was aspirated from cells, 800 µL of Opti-MEM was added to the DNA mixture (total volume now 1 mL), the diluted DNA mixture was applied to cells, and incubated for 12 hours at 37° C. Cells were washed with growth media one to two times and incubated for 12-16 h at 37° C. in 2 ml of growth media. Cells were seeded in 10-cm plates and F12-HAT media was added (F12+10% FBS+1% PenStrep+8 µg/ml blasticidin+1×HAT). Colonies were grown in HAT selection for 2-3 weeks and picked using cloning cylinders at 0.25% Trypsin. Colonies were transferred to a six-well plate and later to 10-cm plates for further colony expansion. For each positive colony, cells were collected from confluent 10-cm plates to make frozen stocks and prepare HAC DNA using standard genomic DNA purification protocols. Positive clones were confirmed by PCR and sequencing across the insert junction to verify that the edited target polynucleotide was successfully transferred to the HAC.

HAC DNA carrying the edited target polynucleotide was transfected into human cells lines for functional studies and further characterization.

Example #3

Producing a *Drosophila melanogaster* Genomic BAC Library

*Drosophila melanogaster* genomic DNA was prepared from adult flies by standard techniques. DNA was partially digested with EcoRI and EcoRI methylase, size fractionated, and cloned into the pBACe3.6 vector (BACPAC Resources Center, Children's Hospital Oakland Research Institute, Oakland, Calif.) by ligation with T4 DNA ligase and transformation into *E. coli*. Digested genomic DNA was ligated with linearized vector at an approximately 1:10 molar ratio of insert:vector. Average insert size was approximately 160 kb. Individual colonies were picked and arrayed in 96-well plates and grown in 25 µg/mL chloramphenicol (chlor) to yield a genomic library of 17,620 recombinant clones representing approximately 25× coverage of the *Drosophila* genome. BAC DNA was prepared by high-throughput 96-well format miniprep and pair-end sequenced to identify inserts. Collection of inserts was reduced to represent approximately 1× overlapping coverage of the *Drosophila melanogaster* genome.

Editing Cassette Preparation: 5 nM of oligonucleotides directed toward saturation mutagenesis of the *Drosophila melanogaster* genome synthesized on a chip were amplified using Q5 polymerase in 50 µL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 30 µL SPRI mix was added to the 50 µL PCR reactions and incubated for 2 minutes. The tubes were subjected to a magnetic field for 2 minutes, the liquid was removed, and the beads were washed 2× with 80% ethanol, allowing 1 minute between washes. After the final wash, the beads were allowed to dry for 2 minutes, 50 µL 0.5×TE pH 8.0 was added to the tubes, and the beads were vortexed to mix. The slurry was incubated at room temperature for 2 minutes, then subjected to the magnetic field for 2 minutes. The eluate was removed, and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation: A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 µL ddH$_2$O and quantified before Gibson Assembly®.

Isothermal Assembly: 150 ng backbone DNA was combined with 100 ng cassette DNA. An equal volume of 2× Master Mix was added, and the reaction was incubated for 45 minutes at 50° C. After assembly, the assembled backbone and cassettes were subjected to SPRI cleanup, as described above.

Transformation with Engine Vector: 1 µL of the engine vector DNA (comprising a coding sequence for MAD7 nuclease under the control of the pL inducible promoter, an ampicillin resistance gene, and the λ Red recombineering system) was added to 50 µL E. coli cells in each well of an array of 384-well plates representing the genomic library described above by liquid handling automation. The transformed cells were plated on LB plates with 25 µg/mL chloramphenicol (chlor) and 100 µg/mL carbenicillin and incubated overnight to accumulate clonal isolates. The next day, a colony was picked, grown overnight in LB+25 µg/mL chlor+100 µg/mL carb, and glycerol stocks were prepared from the saturated overnight culture by adding 500 µL 50% glycerol to 1000 µL culture. The collection of stocks of E. coli cells comprising the Drosophila genomic BAC library and engine vector were frozen at −80° C.

Transformation with Editing Library: The assembled editing vector and electrocompetent collection of E. coli cells carrying the Drosophila genomic BAC library (that carry both the target polynucleotide on a shuttle vector and the engine vector) were transferred into a transformation module for electroporation. The transformation module comprised an ADP-EPC cuvette. See, e.g., U.S. Pat No. 62/551,069. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing kanamycin. Carbenicillin and chloramphenicol were added to the medium after 1 hour, and the cells were allowed to recover for another 2 hours. After recovery, the cells were held at 4° C. until recovered by the user. An aliquot of cells was plated on LB agar supplemented with chloramphenicol, carbenicillin, and kanamycin.

Preparation of Edited Shuttle Vector DNA: Edited BAC DNA was prepared by high-throughput 96-well format miniprep. For each clone, edited target polynucleotide was liberated from the BAC backbone and subcloned in an insect expression vector for downstream functional studies in Drosophila cells. Alternatively, BAC DNA may be isolated from the editing E. coli population in bulk and transfected into Drosophila cells in bulk.

Example #4

Targeted Insertion of Heterologous DNA in the *Saccharomyces cerevisiae* Genome

Figure 10:
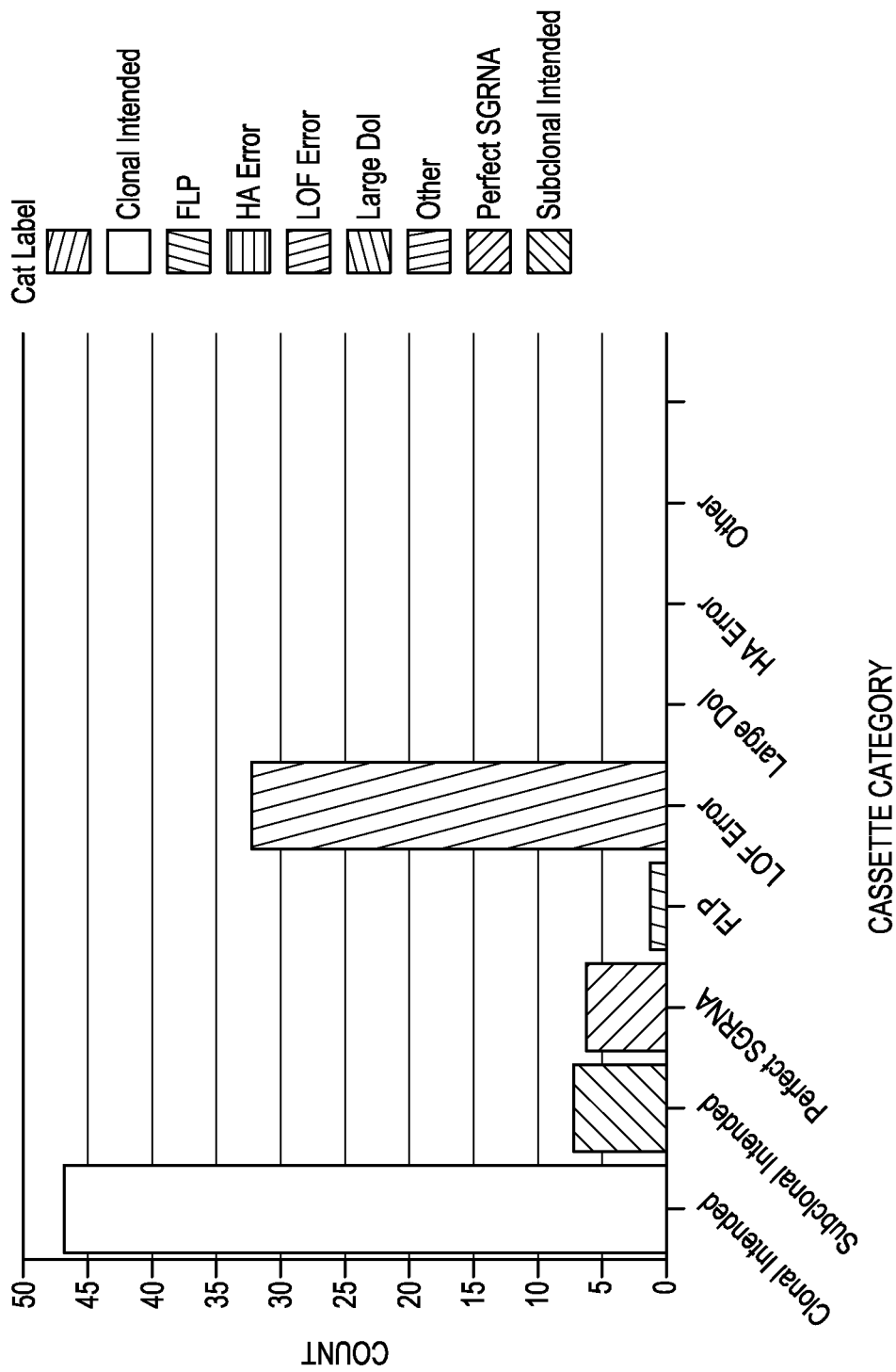
FIG. 10 is a bar graph showing edit categories obtained for the experiment described in Example 4.

Targeted insertion of a single-copy of a heterologous DNA sequence (gene or pathway) into the genome of yeast was achieved by taking advantage of the endogenous homology-directed repair machinery of *Saccharomyces cerevisiae* to precisely integrate said DNA into the desired location on the target chromosome. One system for precise integration of heterologous DNA employs addition to the 5' and 3' ends of the heterologous DNA sequence homology regions of identical sequence to the targeted location of the yeast genome. Additionally, a recyclable counter-selectable marker gene such as URA3 was also included in the targeting DNA sequence. By flanking the counter-selectable marker with a short direct repeat sequence, the marker can be removed from the final integrated DNA construct, leaving behind in the genome only the desired heterologous DNA sequence for further editing with the automated multi-module cell processing system. Transforming DNA was constructed fully intact by gene synthesis though alternatively the DNA may be assembled from two or more fragments using strand overlap extension (SOE) PCR or other assembly methods. Assembled DNA was then transformed into S. cerevisiae and integrated into the yeast chromosome by homologous recombination and candidate strains were obtained by plating on selective growth media, uracil dropout media in this example. Once the correct genomic integration of the heterologous DNA construct was confirmed, the URA3 marker was removed by plating colonies onto growth medium containing 5-fluoroorotic acid (5-FOA) and screening for clones in which the URA3 marker cassette has looped out between the flanking direct repeats. The markerless strain is now ready for genome editing on the heterologous DNA. The outcome of one such editing experiment was evaluated and the data is shown in FIGS. 9 and 10. FIG. 9 is a table showing the edit category and the number of wells that were in each edit category. Note that there were 44 wells comprising clonal complete intended edits, and 6 wells with subclonal complete intended edits. FIG. 10 is a bar graph showing the edit categories.

Example #5

Fully-Automated Singleplex RGN-Directed Editing Run

Singleplex automated genomic editing using MAD7 nuclease was successfully performed with an automated multi-module instrument of the disclosure. See U.S. Pat. No. 9,982,279; and U.S. Ser. No. 16/024,831 filed 30 Jun. 2018; Ser. No. 16/024,816 filed 30 Jun. 2018; Ser. No. 16/147,353 filed 28 Sep. 2018; Ser. No. 16/147,865 filed 30 Sep. 2018; and Ser. No. 16/147,871 filed 30 Jun. 2018.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. *Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20;

polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example #6

Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. Coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in an isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product nonfunctional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A method of nucleic acid-guided nuclease editing of five hundred or more exogenous polynucleotides from source cells within heterologous editing cells in a single multiplexed automated operation, comprising:
    inserting five hundred or more different target polynucleotides from the source cells into shuttle vector backbones to form a library of shuttle vectors;
    transferring the library of shuttle vectors into a first receptacle;
    providing heterologous editing cells in a second receptacle;
    growing the heterologous editing cells in a growth module;
    transferring the heterologous editing cells from the growth module to a transformation module;
    transferring the library of shuttle vectors from the first receptacle to the transformation module;

providing one or more editing vectors wherein the editing vectors comprise a coding sequence for a nuclease, a guide nucleic acid and a DNA donor sequence in a third receptacle;

transferring the editing vectors from the third receptacle to the transformation module;

introducing the library of shuttle vectors and the one or more editing vectors into the heterologous editing cells in the transformation module;

transferring the heterologous editing cells from the transformation module to an editing module;

allowing editing to take place in the editing module under conditions that allow the editing vectors to edit the one or more target polynucleotides in the shuttle vectors thereby forming edited shuttle vectors; and isolating the living edited cells comprising the edited shuttle vectors; and isolating the edited shuttle vectors; wherein the first receptacle, second receptacle, third receptacle, growth module, transformation module and editing module are all part of a stand-alone automated multi-module cell processing instrument, and wherein a liquid handling system moves the library of shuttle vectors and editing vectors from the first and third receptacles, respectively, to the transformation module, and moves the heterologous editing cells from the second receptacle to the growth module, from the growth module to the transformation module and from the transformation module to the editing module all without human intervention.

2. The method of claim 1, wherein one or more of the five hundred or more different target polynucleotides are selected from a full-length gene; an open reading frame coding sequence; or a genomic locus of size 1000-10,000 nucleotides, 50-500 nucleotides, 10-100 nucleotides, or 10,000-100,000 nucleotides.

3. The method of claim 2, wherein one or more of the five hundred or more different target polynucleotides are single open reading frame coding sequences.

4. The method of claim 2, wherein one or more of the five hundred or more different target polynucleotides are genomic loci of size 1000-10,000 nucleotides.

5. The method of claim 2, wherein one or more of the five hundred or more different target polynucleotides are genetic loci of size 10,000-100,000 nucleotides.

6. The method of claim 1, wherein the source cells are selected from bacterial cells, fungal cells, plant cells, mammalian cells and human cells.

7. The method of claim 6, wherein the source cells are bacterial cells.

8. The method of claim 6, wherein the source cells are fungal cells.

9. The method of claim 6, wherein the source cells are plant cells.

10. The method of claim 6, wherein the source cells are mammalian cells.

11. The method of claim 1, shuttle vector backbones are selected from bacterial plasmids, yeast centromeric plasmids, bacterial artificial chromosomes, yeast artificial chromosomes, BAC/YAC hybrids and mammalian artificial chromosomes.

12. The method of claim 11, wherein the shuttle vector backbone is a bacterial plasmid.

13. The method of claim 11, wherein the shuttle vector backbone is a yeast centromeric plasmid.

14. The method of claim 11, wherein the shuttle vector backbone is a bacterial artificial chromosome.

15. The method of claim 11, wherein the shuttle vector backbone is a yeast artificial chromosome.

16. The method of claim 11, wherein the shuttle vector backbone is a BAC/YAC hybrid.

17. The method of claim 11, wherein the shuttle vector is a mammalian artificial chromosome.

18. The method of claim 1, wherein the editing cells are selected from bacterial cells, fungal cells, plant cells, mammalian cells and human cells.

19. The method of claim 1, wherein the editing vectors confer edits comprising saturation mutagenesis edits, knockout edits, loss of function edits, gain of function edits, coding sequence edits and noncoding sequence edits.

20. The method of claim 19, wherein the editing vectors confer edits comprising saturation mutagenesis edits.

21. The method of claim 19, wherein the editing vectors confer knockout edits.

22. The method of claim 19, wherein the editing vectors confer loss of function edits.

23. The method of claim 19, wherein the editing vectors confer coding sequence edits.

24. The method of claim 1, wherein the editing vectors confer noncoding sequence edits.

25. The method of claim 1, wherein the stand-alone automated multi-module cell processing instrument further comprises a cell concentration module, and further comprising the step of after growing the heterologous editing cells in the growth module; and before transferring the heterologous editing cells from the growth module to the transformation module, the heterologous editing cells are concentrated in the cell concentration module.

26. The method of claim 25, wherein the cell concentration module performs tangential flow filtration.

27. The method of claim 1, wherein the step of introducing the library of shuttle vectors and the one or more editing vectors into the heterologous editing cells is performed using a flow-through electroporation (FTEP) device.

28. The method of claim 1, wherein the growth module comprises a rotating growth module.

29. The method of claim 1, wherein the stand-alone automated multi-module cell processing instrument further comprises a recovery module.

30. The method of claim 1, wherein the stand-alone automated multi-module cell processing instrument is controlled by a processor.

* * * * *